US005639782A

United States Patent [19]
Shen et al.

[11] Patent Number: 5,639,782
[45] Date of Patent: *Jun. 17, 1997

[54] NEOLIGNAN DERIVATIVES AS PLATELET ACTIVATING FACTOR RECEPTOR ANTAGONISTS AND 5-LIPOXYGENASE INHIBITORS

[75] Inventors: T. Y. Shen, Charlottesville, Va.; David Goldstein, Pittsburgh, Pa.; Diane M. Gingrich, Tempe, Ariz.

[73] Assignee: Center for Innovative Technology, Herndon, Va.

[*] Notice: The term of this patent shall not extend beyond the expiration date of Pat. No. 5,530,141.

[21] Appl. No.: 117,024

[22] PCT Filed: Mar. 4, 1992

[86] PCT No.: PCT/US92/01830

§ 371 Date: Sep. 3, 1993

§ 102(e) Date: Jan. 3, 1994

[87] PCT Pub. No.: WO92/15294

PCT Pub. Date: Sep. 17, 1992

[51] Int. Cl.⁶ ............ A61K 31/385; C07D 339/06
[52] U.S. Cl. .............. 514/440; 549/35; 549/39
[58] Field of Search ............ 514/440; 549/35, 549/39

[56] References Cited

U.S. PATENT DOCUMENTS

| | | | |
|---|---|---|---|
| 2,690,988 | 10/1954 | Jones et al. | 549/35 |
| 4,166,452 | 9/1979 | Generales, Jr. | 128/741 |
| 4,256,108 | 3/1981 | Theeuwes | 128/260 |
| 4,265,874 | 5/1981 | Bonsen et al. | 424/15 |
| 4,522,811 | 6/1985 | Eppstein et al. | 514/2 |
| 4,539,332 | 9/1985 | Biftu et al. | 514/461 |
| 4,595,693 | 6/1986 | Biftu et al. | 514/461 |
| 4,604,407 | 8/1986 | Haslanger et al. | 514/575 |
| 4,656,190 | 4/1987 | Shen et al. | 514/529 |
| 4,757,084 | 7/1988 | Biftu et al. | 514/438 |
| 4,841,968 | 6/1989 | Dunn et al. | 128/335.5 |
| 4,845,129 | 7/1989 | Anderson et al. | 514/600 |
| 4,871,756 | 10/1989 | Gillard et al. | 514/381 |
| 4,873,259 | 10/1989 | Summers, Jr., et al. | 514/443 |
| 4,876,346 | 10/1989 | Musser et al. | 546/172 |
| 4,891,363 | 1/1990 | Nakamura et al. | 514/94 |
| 4,910,206 | 3/1990 | Houlihan | 514/292 |
| 4,916,145 | 4/1990 | Tilley et al. | 514/357 |
| 4,959,361 | 9/1990 | Walser | 514/220 |
| 4,987,132 | 1/1991 | Mase et al. | 514/252 |
| 4,992,428 | 2/1991 | Houlihan et al. | 514/63 |
| 4,996,203 | 2/1991 | Biftu et al. | 514/231.5 |
| 5,001,123 | 3/1991 | Biftu et al. | 514/235.2 |
| 5,037,853 | 8/1991 | Brooks et al. | 514/595 |
| 5,110,831 | 5/1992 | Magolda et al. | 514/645 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 514/231.5 |
| 5,187,192 | 2/1993 | Brooks et al. | 514/445 |
| 5,234,950 | 8/1993 | Edwards et al. | 514/473 |
| 5,244,896 | 9/1993 | Borcherding et al. | 514/258 |
| 5,288,751 | 2/1994 | Brooks et al. | 514/438 |
| 5,326,787 | 7/1994 | Brooks et al. | 514/507 |
| 5,334,616 | 8/1994 | Brooks et al. | 514/438 |
| 5,358,938 | 10/1994 | Cai et al. | 514/231.5 |
| 5,420,164 | 5/1995 | Mishina et al. | 514/596 |
| 5,434,151 | 7/1995 | Cai et al. | 514/231.5 |

FOREIGN PATENT DOCUMENTS

| | | |
|---|---|---|
| 0144804 | 6/1985 | European Pat. Off. |
| 0199324 | 10/1986 | European Pat. Off. |
| 0217204 | 4/1987 | European Pat. Off. |
| 0252823A1 | 1/1988 | European Pat. Off. |
| 0319947A2 | 6/1989 | European Pat. Off. |
| 0322033 | 6/1989 | European Pat. Off. |
| 0338339A1 | 10/1989 | European Pat. Off. |
| 0365089A2 | 4/1990 | European Pat. Off. |
| 0367110A1 | 5/1990 | European Pat. Off. |
| 0388309A2 | 9/1990 | European Pat. Off. |
| 0402150A1 | 12/1990 | European Pat. Off. |
| 0402151A1 | 12/1990 | European Pat. Off. |
| 0402155 | 12/1990 | European Pat. Off. |
| 0402156 | 12/1990 | European Pat. Off. |
| 0416609A2 | 3/1991 | European Pat. Off. |
| 0617032A1 | 9/1994 | European Pat. Off. |
| 3701344A1 | 7/1987 | Germany . |
| 3724031A1 | 1/1988 | Germany . |
| 3724164A1 | 1/1988 | Germany . |
| 3936828A1 | 5/1990 | Germany . |
| 4000647.1A1 | 9/1990 | Germany . |
| 2197650 | 5/1988 | United Kingdom . |
| 2233974 | 1/1991 | United Kingdom . |
| 90/12015 | 10/1990 | WIPO . |
| WO92/09566 | 6/1992 | WIPO . |
| 92/13848 | 8/1992 | WIPO . |
| WO94/01430 | 1/1994 | WIPO . |
| WO94/04537 | 3/1994 | WIPO . |

OTHER PUBLICATIONS

Bartroli, J., "Design of Potent Linear PAF Antagonist," *J. Med. Chem.*, vol. 34 (1991) pp. 3328–3334.

Biftu, T., et al., "Conformation and Activity of Tetrahydrofuran Lignans and Analogues as Specific Platelet Activating Factor Antagonists," *J. Med. Chem.* vol. 29, No. 10 (1986) pp. 1917–1921.

Carlcellar, E., et al., "4–Substituted 2–Alkoxytetrahydrofurans as Potent and Long–Lasting PAF Antagonists," *J. Med. Chem.*, vol. 35 (1992) pp. 676–683.

Corey, F.J. et al., "Dual Binding Modes to the Receptor for Platelet Activating Factor (PAF) of Anti–PAF Trans–2, 5–Diarylfurans," *Tetrahedron Letters*, vol. 29, No. 24 (1988) pp. 2899–2902.

(List continued on next page.)

Primary Examiner—Shailendra Kumar
Assistant Examiner—Mary C. Cebulak
Attorney, Agent, or Firm—Sherry M. Knowles; Kilpatrick & Cody L.L.P.

[57] ABSTRACT

Neolignan derivative compounds of the 2,4-diaryl-1,3-dithiolane and futoenone variety exhibit both PAF and 5-lipoxygenase antagonist activity.

30 Claims, 29 Drawing Sheets

OTHER PUBLICATIONS

Crawley, G.C., "Methoxytetrahydropyrans. A New Series of Selective and Orally Potent 5–Lipoxygenase Inhibitors," *J. Med. Chem.*, vol. 35, No. 14 (1992) pp. 2600–2609.

Feinmark, S. J., "Leukotriene $C_4$ Biosynthesis during Polymorphonuclear Leukocyte–Vascular Cell Interactions," *Methods in Enzmology*, vol. 187, pp. 559–560 1992.

Guthrie, R.W., et al., "Propenyl Carboxamide Derivatives As Antagonists of Platelet Activating Factor," *J. Med. Chem.*, vol. 33 (1990) pp. 2856–2864.

Graham, D.W., et al., "1,3–Diarylcyclopentanes: A New Class of Potent PAF Receptor Antagonists," MEDI 1990.

Hwang, S., "Specific Receptors of Platelet–Activating Factor, Receptor Heterogeneity, and Signal Transduction Mechanisms," *J. Lipid Mediators*, vol. 2 (1990) pp. 123–158.

Lave, D., et al., "Pyrrolo[1,2–c]Thiazole Derivatives: Potent PAF Receptor Antagonists," *Drugs of the Future*, vol. 14, No. 9 (1989) pp. 891–898.

McColl, S.R., "Determination of 5–Lipoxygenase Activity in Human Polymorphonuclear Leukocytes Using High–Performance Liquid Chromatography," *J. Chromatography*, vol. 378 (1986) pp. 44–449.

Musser, J.H., et al., "5–Lipoxygenase: Properties, Pharmacology, and the Quinolinyl(bridge)aryl Class of Inhibitors," *J. Med. Chem.*, vol. 35, No. 14 (1992) pp. 2502–2524.

Goldstein, D., et al., "Dual Inhibitors of Platelet Activating Factor and 5–Lipoxygenase II . . . " *Chemical Abstracts* vol. 118, No. 19, May 1993, Abstract No. 185258m.

Goldstein, D., et al., "Dual Inhibitors of Platelet Activating Factor and 5–Lipoxygenase I.," *Chemical Abstracts*, vol. 118, No. 19, May 1993, Abstract No. 182990h.

O'Donnell, M., et al., "Comparison of the Pulmonary Pharmacology of Leukotrienes and PAF: Effects of their Antagonists," *Therapeutic Approaches to Inflammatory Diseases* Proceedings of the Fourth International Conference of the Inflammatory Research Association, Oct. 23–27, 1988, White Haven, Pennsylvania, p. 169.

Ogiso, A., et al., "The Structure of Futoenone, A Novel Spiro–Cyclohexdienone Derivative," *Tetrahedron Letters*, No. 16, (1968) pp. 2003–2008.

Ogiso, A., et al., "The Structure and Total Synthesis of Futoenone, a Constitute of *Piper futokadzura* SIEB, et ZUCC.," *Chem. Pharm. Bull.*, vol. 18, No. 1, (1970) pp. 105–114.

Page, C., et al., "PAF: New Antagonists, New Roles in Diseases and a Major Role in Reproductive Biology," *3rd International Conference on Platelet–Activating Factor and Structurally Related Alkyl Ether Lipids*, Tokyo, Japan, May 8–12, 1989.

Ponpipom, M.M., et al., "Structure–Activity Relationships of Kadsurenone Analogues," *J. Med. Chem.*, vol. 30 (1987) pp. 136–142.

Ponpipom, M.M., et al., "(±)–*TRANS*–2–(3–Methylsulfonyl–4–Propoxyphenyl)–5–(3,4,5–Trimethoxypenyl)Tetrahydrofuran (L–659,989), A Novel, Potent PAF Receptor Antagonist," *Biochemical and Biophysical Research Communications*, vol. 150, No. 3 (1988) pp. 1213–1220.

Shen, T.Y., "Characterization of a Platelet–Activating Factor Receptor Antagonist Isolated from Halifenteng (*Piper futokadsura*): Specific Inhibition of in vitro and in vivo Platelet–Activiting Factor–Induced Effects," *Proc. Natl. Acad. Sci. USA*, vol. 82, (Feb. 1985) pp. 672–676.

Shen, .Y., et al., "The Chemical and Biological Properties of PAF Agonists, Antagonists, and Biosynthetic Inhibitors," *Platelet–Activating Factor and Related Lipid Mediators*, Plenum Press, New York, NY, pp. 153–190 1987.

Weber, K.H., et al., "Hetrazepines as Antagonists of Platelet Activating Factor," *Medicinal Research Reviews*, vol. 9, No. 1 (Jan.–Mar. 1989) pp. 181–218.

Biftu, T., et al., *Abstr. of 6th Int. Conf. on Prostaglandins and Related Compounds*, Florence, Italy, p. 302 (Jun. 3–6, 1986).

Backvall, et al., "A Stereocontrolled Organopalladium Route to 2,5–Disubstituted Pyrrolidine Derivatives. Application to the Synthesis of a Venom Alkaloid of the Ant Species *Monomorium latinode*," *J. Org. Chem.*, 55:826–831 (1990).

Bowles, et al., "A Convenient Preparation of Cyclic Ether Acetals Mediated by Trifluoroacetic Anhydride", *Synlett*, pp. 111–112 (1993).

Carter, et al., "5–Lipoxygenase Inhibitory Activity of Zileuton," *J. Pharmacol. and Exp. Therap.*, 256(3):929–937 (1991).

Danyoshi et al., "Pyrrolidine Derivatives as Inhibitors of Platelet Aggregation Induced by Platelet Activating Factor," *Chem. Pharm. Bull.*, 37(7):1969–1970 (1989).

Erez, et al., "Narcotic Antagonistic Potency of Bivalent Ligands Which Contain Beta–Naltrexamine. Evidence for Bridging between Proximal Recognition Sites," *J. Med. Chem.*, 25(7):847–849 (1982).

Foye, "Bioisosterism," *Principles of Medicinal Chemistry*, Second Edition, (Publisher, Lea & Febiger, Philadelphia, 1981), pp. 80–81.

Hwang, S., et al., "*Trans*–2, 5–bis–(3,4,5–trimethoxyphenyl)tetrahydorfuran," *Journal of Biological Chemistry*, 260(29):15639–15645 (1985).

Hwang, S., et al., "Biochemical and Pharmacological Charactgerization of L–659, 989: An Extremely Potent, Selective and Competitive Receptor Antagonist of Platelet–Activating Factor," *J. Pharmacol. Ther.*, 246(2):534–541 (1988).

Ikeda et al., "Preparation of Hydroxamic Acid and N–Hydroxyurea Derivatives and Their Use as Lipoxygenase Inhibitors," *Chemical Abstracts*, vol. 118, Abstract No. 59426 (1993).

Page, C. et al., "PAF: New Antagonists, New Roles in Diseases and Major Role in Reproductive Biology," *Trends in Pharm. Sci.*, 10:1, 256–257 (Elsevier Science Publishers, 1989).

Sahoo, et al., "Synthesis and Biological Activity of MK 287 (L–680,573): A Potent Specific and Orally Active PAF Receptor Antagonist," *Bioorg. Med. Chem. Let.*, 1:327–332 (1991).

Schwenk, et al., "Identification of 5–Oxo–15–hydroxy–6,8, 11,13–eicosatetraenoic Acid as a Novel and Potent human Eosinophil Chemotactic Eicosanoid," *J. Biol. Chem.*, 267(18):12482–12488 (1992).

Seminario and Gleich, "The role of eosinophils in the pathogenesis of asthma," *Curr. Opin. in Immunol.*, 6:860–864 (1994).

Shen and Hussaini, "Kadsurenone and Other Related Lignans as Antagonists of Platelet–Activating Factor Receptor," *Methods of Enzymol.*, 187:446–454 (1990).

Shizuri, et al., "Synthesis of some physiologcally active substances using anodic oxidation of phenols as a key–step," *Chemical Abstracts*, 100:565, No. 209492q (1984).

Talapatra, et al., "Maglifloenone, a novel spirocyclohexadienone neolignan and other constituents from Magnolia liliflora," *Chemical Abstracts*, 97:346, No. 52493k (1982).

Terashita, et al., "CV–3988—A Specific Antagonist of Platelet Ativating Factor (PAF)," *Life Sciences*, 32(17):1975–1982 (1983).

Wood et al., "Cyclic Ether Acetal Platelet Activating Factor (PAF) Receptor Antagonists II: Imidazo[4,5-c]Pyridyl Derivatives," *Bioorg. Med. Chem. Letters*, 3(8):1499–1504 (1993).

Yeadon, et al., "Effect of BW B70C, a novel inhibitor of arachidonic acid 5-lipoxygenase, on allergen-induced bronchoconstriction and late-phase lung eosinophil accumulation in sensitised guinea-pigs," *Agents and Actions*, 38:1–18 (1993).

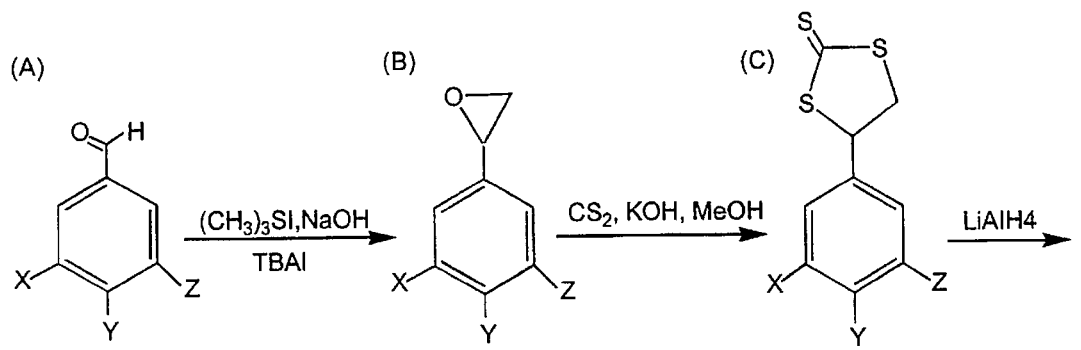
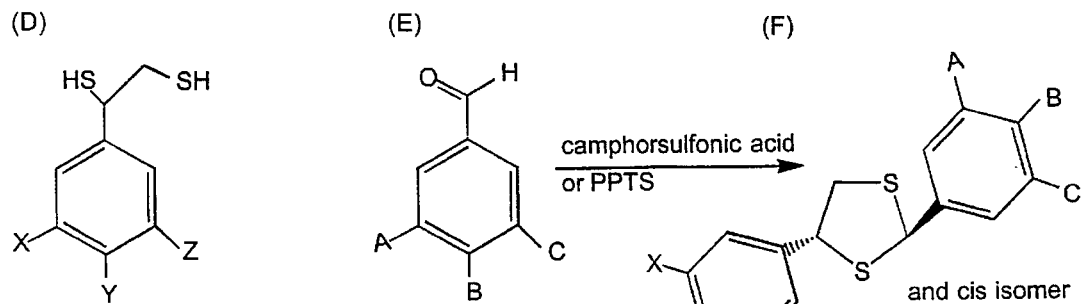
(A)
24 X,Y,Z = OCH3
25 X,Z = OCH3, Y=OCH2OCH3
26 X,Z = SCH3, Y=OCH3
27 X,Z = SCH3, Y=OCH2OCH3
(B)
28 X,Y,Z = OCH3
29 X,Z = OCH3, Y=OCH2OCH3
30 X,Z = SCH3, Y=OCH3
31 X,Z = SCH3, Y=OCH2OCH3
(C)
32 X,Y,Z = OCH3
33 X,Z = OCH3, Y=OCH2OCH3
34 X,Z=OCH3, Y=OH
35 X,Z = SCH3, Y=OCH3
36 X,Z = SCH3, Y=OCH2OCH3
37 X,Z = SCH3, Y=OH
(D)
38 X,Y,Z = OCH3
39 X,Z = OCH3, Y=OCH2OCH3
40 X,Z = OCH3, Y=OH
41 X,Z = SCH3, Y=OCH3
42 X,Z = SCH3, Y=OCH2OCH3
43 X,Z = SCH3, Y=OH
(E)
(F)
1-21
FIGURE 1

Synthesizer Component and Inhibition of PAF Induced Platelet Aggregation and Inhibition of the Biosynthesis of LTB4

| COM # | X | Y | Z | A | B | C | PAF $IC_{50}$ | PMN $IC_{50}$ | MONO $IC_{50}$ |
|---|---|---|---|---|---|---|---|---|---|
| 1 | $OCH_3$ | $OCH_3$ | $OCH_3$ | $OCH_3$ | $OCH_3$ | $OCH_3$ | 0.8 | | |
| 2 | $OCH_3$ | $OCH_3$ | $OCH_3$ | OH | $OCH_3$ | $OCH_3$ | | | |
| 3 | $OCH_3$ | $OCH_3$ | $OCH_3$ | OCOPh | $OCH_3$ | $OCH_3$ | | | |
| 4 | $OCH_3$ | $OCH_3$ | $OCH_3$ | $OCH_2OCH_3$ | $OCH_3$ | $OCH_3$ | | | |
| 5 | $OCH_3$ | $OCH_3$ | $OCH_3$ | $OCH_3$ | OH | $OCH_3$ | 2.0 | | 8.0 |
| 6 | $OCH_3$ | $OCH_3$ | $OCH_3$ | $NO_2$ | OH | $OCH_3$ | 25.0 | | |
| 7 | $OCH_3$ | $OCH_3$ | $OCH_3$ | I | OH | $OCH_3$ | | | 30.0 |
| 8 | $OCH_3$ | $OCH_3$ | $OCH_3$ | I | $OCH_3$ | $OCH_3$ | | | |
| 9 | $OCH_3$ | $OCH_3$ | $OCH_3$ | $CH_3$ | OH | $CH_3$ | | | |
| 10 | $OCH_3$ | $OCH_3$ | $OCH_3$ | t-butyl | OH | t-butyl | | | |
| 11 | $OCH_3$ | OH | $OCH_3$ | $OCH_3$ | OH | $OCH_3$ | 15.0 | | 13.0 |
| 12 | $OCH_3$ | OH | $OCH_3$ | $OCH_3$ | $OCH_3$ | $OCH_3$ | 6.0 | | 12.0 |
| 13A | $OCH_3$ | $OCH_3$ | $OCH_3$ | $SCH_3$ | OH | $SCH_3$ | | 1.0 | 1.0 |
| 13B | $SCH_3$ | OH | $SCH_3$ | $SCH_3$ | OH | $SCH_3$ | | | |
| 13C | $SCH_3$ | $OCH_3$ | $SCH_3$ | $SCH_3$ | $OCH_3$ | $SCH_3$ | | | |
| 13D | $SCH_3$ | $OCH_3$ | $SCH_3$ | $SCH_3$ | OH | $SCH_3$ | | | |
| 13E | $SCH_3$ | OH | $SCH_3$ | $SCH_3$ | $OCH_3$ | $SCH_3$ | | | |
| 14 | $OCH_3$ | $OCH_3$ | $OCH_3$ | $SO_2CH_2CH_2OH$ | $OCH_2CH_2CH_3$ | $OCH_3$ | | | |
| 15 | $OCH_3$ | $OCH_3$ | $OCH_3$ | $SO_2CH_3$ | $OCH_2CH_2CH_3$ | $OCH_3$ | 4.0 | | |
| 16 | $OCH_3$ | $OCH_3$ | $OCH_3$ | $SO_2CH_2CH_2OH$ | $OCH_3$ | $OCH_3$ | | | |
| 17 | $OCH_3$ | $OCH_3$ | $OCH_3$ | $SO_2CH_2CH_2OC_6H_4NO_2$ | $OCH_3$ | $OCH_3$ | | | |
| 18 | $OCH_3$ | $OCH_3$ | $OCH_3$ | $OCH_3$ | $OCH_2CH_2OH$ | $OCH_3$ | | | |
| 19 | $OCH_3$ | $OCH_3$ | $OCH_3$ | $OCH_3$ | $OCH_2CH_2CH_2Br$ | $OCH_3$ | | | |
| 20 | $OCH_3$ | $OCH_3$ | $OCH_3$ | $OCH_2CH_2OH$ | $OCH_3$ | $OCH_3$ | | | |
| 21 | $OCH_3$ | $OCH_3$ | $OCH_3$ | $OCH_2CH_2CH_2OH$ | $OCH_3$ | $OCH_3$ | | | |

Figure 2

|  | X | Y | (X)$_n$ |
|---|---|---|---|
| 22a | OCH$_3$ | OCH$_3$ | (CH$_2$O)$_3$CH$_2$CH$_2$ |
| 22b | OCH$_3$ | OCH$_3$ | (CH$_2$O)$_2$CH$_2$CH$_2$ |
| 22c | OCH$_3$ | OCH$_3$ | CH$_2$CH$_2$OCH$_2$CH$_2$ |

FIGURE 6A

|  | X | Y | (X)$_n$ | IC$_{50}$ (μM) |
|---|---|---|---|---|
| 22d | OCH$_3$ | OCH$_3$ | (CH$_2$)$_8$ | 9.0 |
| 22e | OCH$_3$ | OCH$_3$ | (CH$_2$O)$_3$CH$_2$CH$_2$ | |
| 2+2f | OCH$_3$ | OCH$_3$ | (CH$_2$O)$_4$CH$_2$CH$_2$ | |
| 22g | OCH$_3$ | OCH$_3$ | (CH$_2$O)$_5$CH$_2$CH$_2$ | |

FIGURE 6B

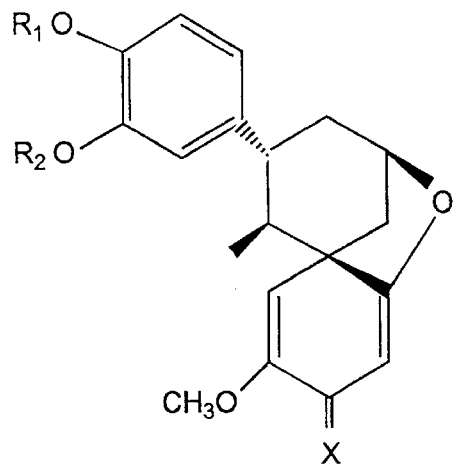
| Compound | IC$_{50}$, uM |
|---|---|
| (101) X = O, R$_1$, R$_2$ = -CH$_2$- (Futoenone) | 13.6 |
| (116) X = O, R$_1$, R$_2$ = H | 0.54 |
| (117) X = O, R$_1$, R$_2$ = CH$_3$ | 21.7 |
| (102) X = S, R$_1$, R$_2$ = CH$_2$- | ~15 |
FIGURE 14A     FIGURE 14B
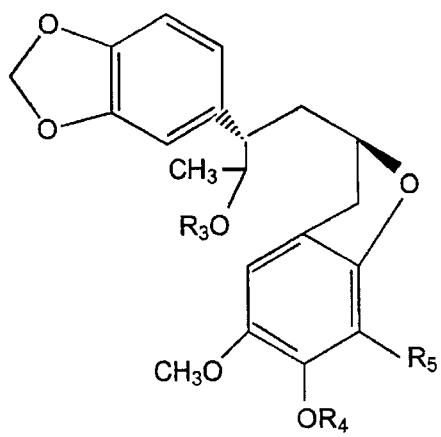
| Compound | IC$_{50}$, uM |
|---|---|
| (105) R$_3$ = H, R$_4$ = H, R$_5$ = H | 10.8 |
| (103) R$_3$ = COCH$_3$, R$_4$ = COCH$_3$, R$_5$ = H | 13.0 |
| (107) R$_3$ = H, R$_4$ = CH$_2$CH=CH$_2$, R$_5$ = H | 21.4 |
| (108a) R$_3$ = H, R$_4$ = H, R$_5$ = CH$_2$CH=CH$_2$ | 15.8 |
| (108c) R$_3$ = H, R$_4$ = COCH$_3$, R$_5$ = CH$_2$CH=CH$_2$ | 4.47 |
FIGURE 15A     FIGURE 15B

| Compound | IC$_{50}$, uM |
|---|---|
| (105) R = H | 0.78 |
| (108a) R =CH$_2$CH=CH$_2$ | 1.04 |
| NDGA | 0.76 |
| (Nordihydrogyauarectic acid) | |
| (Reference compound known to inhibit 5-lipoxygenase) | |

Synthesis of Substituted Aryl or Heteroaryl Derivatives of Futoenone 3,4,5-Trimethoxyphenyl magnesium bromide can be replaced by other substituted aryl or heteroaryl Grignard reagents to prepare the corresponding aryl substituted futoenone derivatives. The R group can be replaced by alkoxy or alkylthio groups

24 : R = CH₃
25 : R = (CH₂)₂O(CH₂)₂
26 : R = CH₂CH₃

| Compound # | n |
|---|---|
| 33a | 3 |
| 33b | 5 |
| 33c | 7 |

NEOLIGNAN DERIVATIVES AS PLATELET ACTIVATING FACTOR RECEPTOR ANTAGONISTS AND 5-LIPOXYGENASE INHIBITORS

BACKGROUND OF THE INVENTION

This application is a 371 of PCT/US92/01830 filed Mar. 4, 1992.

1. Field of the Invention

The present invention is generally related to neolignan derivatives which inhibit both platelet activating factor and 5-lipoxygenase for the treatment of inflammatory and allergic disorders.

2. Description of the Prior Art

Platelet activating factor (PAF) is a highly potent ether linked phospholipid (1-O-alkyl-2-acetyl-sn-glycerol-3-phosphorylcholine) which activates platelets as well as modulates the function of leukocytes and other target cells. PAF has been shown to be a mediator of a variety of pathophysiological conditions including arthritis, acute inflamation, asthma, endotoxic shock, pain, psoriasis, ophthalmic inflammation, ischemia, and gastrointestinal ulceration. Interaction with a specific membrane recognition site coupled to phosphatidylinositol metabolism produces the biological activity of PAF. Hence, blocking the PAF receptor can provide beneficial medical results in human beings and mammals suffering from diseases or disorders mediated by PAF.

Several PAF antagonists have recently been synthesized or isolated from natural sources. For example, Shen et al. in Proc. Natl. Acad. Sci. (U.S.A.), 82. 672–678 (1985), reported that kadsurenone, a neolignan derivative isolated from Piper fotukadsura Sieb et Zucc (a Chinese herbal plant), was a potent, specific and competitive inhibitor of PAF at the receptor level. Biftu et al., in J. Med. Chem. 29, 1917 (1986), and Ponpipom et al., in Biochem. Bioshys. Res. Comm. 150, 1213 (1988), have shown that 2,5-diaryltetrahydrofurans L-652,731 and L-659,989 (both of which are synthetic analogs of neolignan), respectively, are potent PAF receptor antagonists. U.S. Pat. No. 4,539,332 to Biftu et al. and U.S. Pat. No. 4,595,693 to Biftu et al. are both related to the use of 2,5-diaryltetrahydrofurans and their analogs as PAF antagonists. Graham et al., in 197th Amer. Chem. Soc. National Meeting Abstracts, 1989, MEDI, 25, 20, Corey, et al. in Tet. Lett., Vol. 29, 2899–2902 (1988), and U.S. Pat. No. 4,656,190 to Shen et al. respectively show that 1,3-diarylcyclopentanes, 2,4-diaryldioxolanes, and indene derivatives are also potent PAF receptor antagonists.

Leukotrienes, lke PAF, are potent lipid mediators of a variety of topical and systemic diseases and disorders. 5-lipoxygenase catalyzes the conversion of arachidonic acid to leukotriene A4 which is the precursor of leukotrienes B4 and C4. Leukotrienes B4 and C4 are oxygenated metabolites that contribute to the pathogenesis of such inflammatory disorders as arthritis, asthma, psoriasis, and thrombotic disease. Leukotrienes are released concomitantly from leukocytes with PAF from a common phospholipid precursor upon cellular activation and act synergistically with PAF in many biological models. It has been demonstrated that a physical combination of a PAF antagonist and a leukotriene inhibitor is significantly more effective than either agent alone in treating asthma in an animal model (see, O'Donnell et al. in Therapeutic Approaches to inflammatory Diseases, Lewis et al., Elsevier, New York, 1989, pp.169–193).

Shen et al., in PAF and Related Lipid Mediators, Plenum Pub., New York, 164 (1987) and Page et al., in Trends in Pharmacol. Sci. 10, 1 (1989), pointed out that single compounds which posess the dual inhibitory capability of PAF and leukotriene inhibition would have greater antiinflammatory activities than a physical combination of a PAF and a leukotriene inhibitor. Moreover, the chemical combination of PAF and 5-lipoxygenase inhibitory activities in one molecule has advantages over drug combinations in terms of optimal pharmacokinetics, clinical applications and developmental costs. However, few compounds are known which posess this dual inhibitory activity. Shen et al., in PAF and Related Lipid Mediators, Plenum Pub: New York, 153–190 (1987), reported that a tetrahydrothiophene analog of lignan, L-653,150, is both a potent PAF antagonists and a moderate inhibitor of 5-lipoxygenase. European Pat. No. Application 0,365,089 to Biftu, filed Oct. 13, 1989, is also directed the use of tetrahydrothiophene analoqs as leukotriene inhibitors and specific PAF antagonists.

Because of the large number of diseases and disorders which are mediated by leukotrienes and PAF, synthesis of new compounds which posess leukotriene or PAF inhibitory activity, and preferably compounds which possess both inhibitory activities, as well as the identification of existing compounds which possess either or both inhibitory activities, will provide a great benefit to society in the treatment of those diseases and disorders.

SUMMARY OF THE INVENTION

It is therefore an object of this invention to provide neolignan derivatives which both act as PAF antagonists and inhibit biosynthetic production of leukotrienes via the 5-lipoxygenase pathway.

It is another object of this invention to provide novel 2,4-diaryl-1,3-dithiolanes as a new class of potent PAF receptor antagonists which also inhibit 5-lipoxygenase.

It is another object of this invention to provide a method of using 2,4-diaryl-1,3-dithiolanes as PAF antagonists and 5-lipoxygenase inhibitors.

It is another object of this invention to provide stereoselective processes for the preparation of optical isomers of 2,4-diaryl-1,3-dithiolanes.

It is yet another object of this invention to provide a method of using futoenone and futoenone derivatives as dual acting PAF antagonists and 5-lipoxygenase inhibitors.

It is yet another object of this invention to provide novel futoenone derivatives as potent PAF receptor antagonists which also inhibit 5-lipoxygenase.

It is a further object of this invention to provide a method of treating PAF and leukotriene mediated diseases by using neolignan derivatives such as 2,4-diaryl-1,3-dithiolanes and futoenone derivatives as dual acting PAF antagonists and 5-lipoxygenase inhibitors.

According to the invention, many new 2,4-diaryl-1,3-dithiolane compounds and futoenone derivative compounds have been synthesized. Many of the compounds have been examined in vitro, and have been shown to possess both PAF and 5-lipoxygenase inhibition activity.

The compounds of the present invention may be employed as pharmaceuticals which include the compound and an acceptable pharmaceutical carrier. Such pharmaceutical compositions may be administered orally, topically (eg., as an ointment or by means of a transdermal patch), parentally, intranasally (eg., by inhalation spray), or rectally. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharamceutical compositions and such compositions may contain one or more agents selected from the group consisting of sweetening agents, flavoring agents, coloring agents and preserving agents in order to provide pharamceutically elegant and palatable preparations. Tablets contain the active ingredient in admixture with non-toxic pharamceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, clacium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharamceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds are employed.

Dosage levels of the order of from about 0.01 mg to about 150 mg per kilogram of body weight per day are useful in the treatment of the above-indicated conditions (about 0.7 mg to about 10 gms. per patient per day, for patients having an average body weight of 70 kg). For example, inflammation may be effectively treated by the administration of from about 0.015 to about 50 mg of the compound per kilogram of body weight per day (about 1.0 mg to about 3.5 gms per patient per day). Preferably a dosage of from about 3 mg to about 20 mg per kilogram of body weight per day may produce good results (about 20 mg to about 1.5 gm per patient per day).

The amount of active ingredient that may be combined with the carrier materials to produce a single dosage form will vary depending upon the host treated and the particular mode of administration. For example, a formulation intended for the oral administration to humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a schematic drawing showing a synthetic pathway for producing 2,4-diaryl-1,3-dithiolane compounds;

FIG. 2 is a table showing the substituent groups of many 2,4-diaryl-1,3-dithiolane compounds which may be produced according to FIG. 1 and the PAF and 5-lipoxygenase antagonist activities observed for several of the compounds;

FIGS. 6a and 6b are tables which respectively show the chemical substituents of the dimeric compounds shown in FIGS. 5a and 5b as well as data on PAF antagonistic activity;

FIGS. 14a and 14b are respectively a chemical structure of a substituted futoenone compound and a table showing the PAF antagonist activity of particular futoenone derivative compounds;

FIGS. 15a and 15b are respectively a chemical structure of a substituted futoenone derivative compound and a table showing the PAF antagonist activity of particular futoenone derivative compounds;

Figure 3:
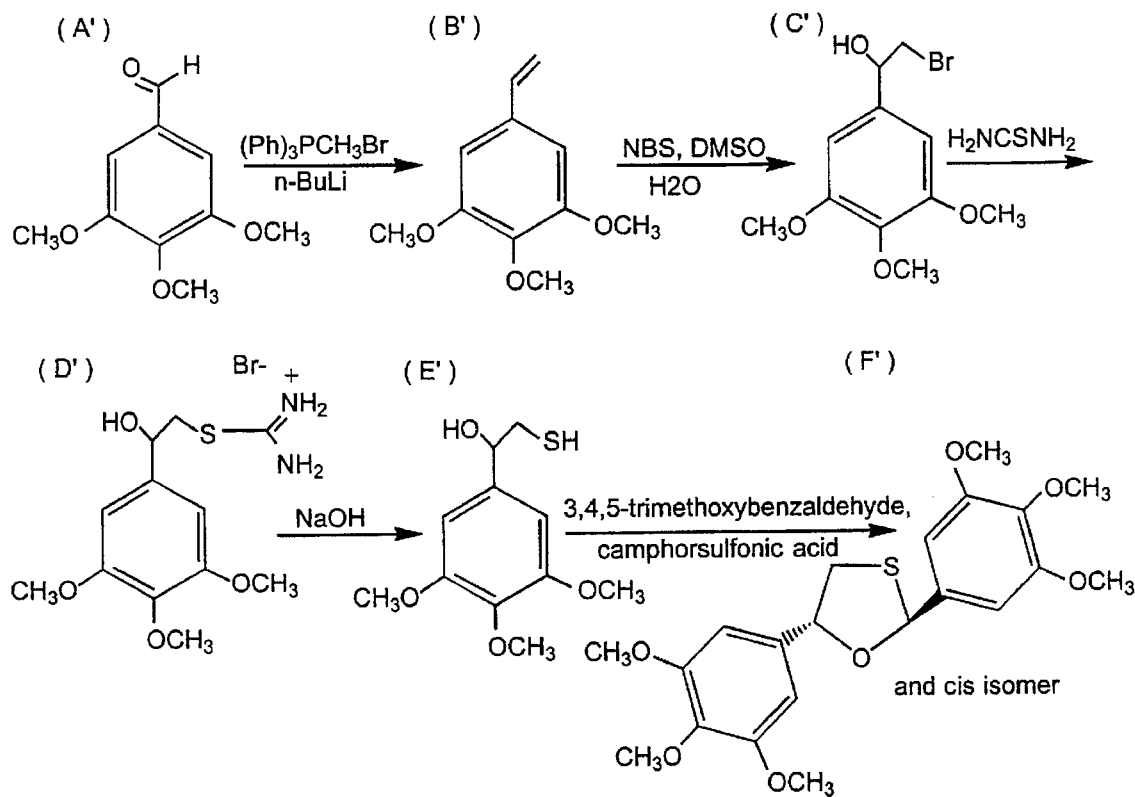
FIG. 3 is a schematic drawing showing a synthetic pathway for producing the oxathiolane analog of the diaryltetrahydrofuran L-652,731.

The invention is also described herein with respect to the following tables wherein:

Table 1 illustrates inhibition of PAF induced platelet aggregation and inhibition of $LTB_4$ biosynthesis by dual-acting 2,4-diaryl-1,3-dithiolane having the following structural formula:

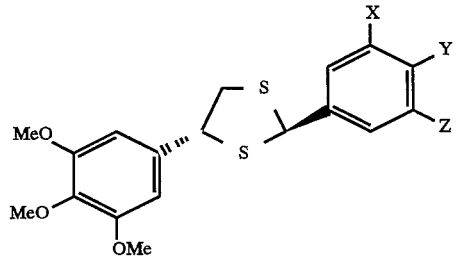

(X, Y, and Z are described in Table 1) and their cis-isomers;

Table 2 illustrates inhibition of PAF induced platelet aggregation and inhibition of $LTB_4$ biosynthesis by dual-acting 2,4-diaryl-1,3-dithiolanes with picolylamine side chain, and having the structural formula:

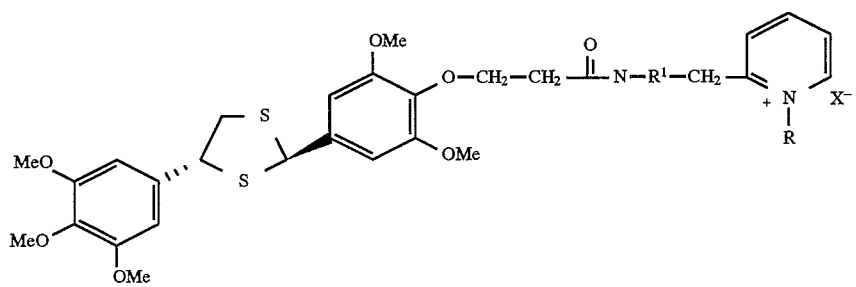

(R¹, R², and X are described in Table 2), and their cis-isomers;

Table 3 illustrates inhibition of PAF induced platelet aggregation by dimeric 2,4-diaryl-1,3-dithiolanes having the following formula:

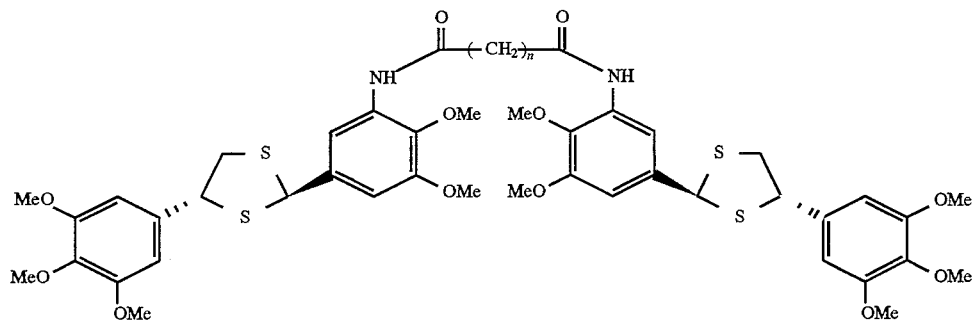

(n is described in Table 3).

DETAILED DESCRIPTION OF THE PREFERRED EMBODIMENTS OF THE INVENTION

In vitro experiments have been conducted to determine the PAF and 5-lipoxygenase inhibitory activity of a variety of synthesized, neolignan derivative compounds. In particular, the novel compounds are either 2,4-diaryl-1,3-dithiolanes or futoenone derivatives. PAF antagonist activity was determined according to the method of Shen et al., in *Methods of Ezymology*, Vol. 187, 447–449 (1990), and that article is herein incorporated by reference. The 5-lipoxygenase inhibitory activity was determined according to an assay discussed below.

The following outlines a platelet aggregation assay procedure. Blood is obtained from human volunteers who have not ingested aspirin or steroid drugs for ten days and is stored with a 3.8% trisodium citrate anticoagulant. Heparin is not used as the anticoagulant since it interferes with platelet aggregation. Citrated blood is centrifuged at 220 g for 10 min. at room temperature to obtain platelet-rich plasma (PRP). The platelet count is determined and is adjusted to $2.5 \times 10^7$ platelets/ml. Platelet-poor plasma (PPP) is prepared by centrifuging PRP at 1000 g for 20 min. to pelletize the platelets. PPP is used to calibrate the aggregometer. Washed platelet suspension (WPS) is prepared from PRP by underlayering the latter with Ficoll-Paque (9:2, v/v) and centrifuging at 750 g for 15 min. at room temperature. The platelets form a band between the plasma and the separation medium and are carefully collected and suspended in Tyrode's solution (in mM: NaCl, 137; KCl, 2.7; NaHCO₃, 11.9; NaH₂-PO₄, 0.42; MgCl₂, 1.0; CaCl₂, 1.0; HEPES, 5.0; and dextrose, 1 g/liter, with 0.25% BSA, w/v, pH 7.4). Prostacyclin (PGI₂) (1 ng/ml) can be added to the suspension to prevent platelet activation; however, it should be understood that the inhibitory activity of PGI₂ disappears completely 10 min. from the time of addition at room temperature. The suspension is then spun at 1000 g for 10 min. and the pellet is resuspended in Tyrode's buffer for platelet aggregation. The suspensions are maintained at 37° C. and stirred constantly at 1000 revolutions per min (rpm). A known amount of PAF, such as 0.11 μM PAF, is added to the suspension three to five minutes after the addition of the potential PAF antagonists (the synthesized compounds). The effect of the PAF antagonist can be expressed as a percentage inhibition of the observed control maximum platelet aggregation (the aggregation observed for a suspension to which only PAF has been added) or as the concentration of the antagonist which reduces the maximum response of the platelets by 50% (commonly called the IC₅₀ value). To obtain the IC₅₀ value, varying concentrations of a potential antagonist need to be added to the test suspensions with the percentage inhibition being determined for each concentration of the antagonist, and the IC₅₀ value is obtained from a plot of the percentage inhibition versus concentration of the antagonist.

The 5-lipoxygenase assay can be determined according to the following procedure. Human blood is obtained from volunteers who have not taken drugs for the previous ten days. Human polymorphonuclear (PMN) leukocytes and monocytes are isolated according to the procedure by Steven Feinmark, in *Methods in Enzymology*, Vol. 187, 559 (1990), this article being incorporated herein by reference. Using an adapted procedure of McColl et al., *J. Chromatography*, Vol. 378, 444 (1986), this article being herein incorporated by reference, the isolated PMN and/or monocyte pellets are suspended in Hank's balanced salt solution (HBSS) and cooled in an ice bath. Varying concentrations of potential antagonists (i.e., the synthesized compounds) are added to tubes containing the suspension, except for four control tubes. The suspension and potential 5-lipoxygenase inhibitors are mixed thoroughly. Arachidonic acid is added to two of the controls (0° C.) followed immediately by quenching with ethyl acetate. Arachidonic acid (10 µl of a 10 mM solution) is then added to and mixed thoroughly with the suspension (1 ml) in the remaining tubes followed by the addition of a calcium ionophore A23187 (5 µl of 1 mM solution) to all tubes except the 0° C. controls (those already being quenched with ethyl acetate) and incubation of the tubes at 37° C. proceeds for two minutes. The reaction in each tube was quenched and the metabolites extracted by adding ethyl acetate (1 ml) to each tube followed by centrifugation of the entire tube at 1000 g for five minutes. This extraction produces two layers where the top layer is ethyl acetate that is separated and subsequently removed by drying under a stream of nitrogen. The residues are redissolved in methanol. Leukotriene $B_4$ ($LTB_4$) is monitored using an HPLC set to absorb at 280 nm. The retention time for $LTB_4$ is determined using a pure standard, such as that which can be purchased from Sigma Chemical. Care should be taken to maintain the samples at low temperature prior to injection in the HPLC. The peak areas associated with $LTB_4$ formation are determined (preferably in duplicate and averaged) for each sample and the percent inhibition for each concentration level of inhibitor was calculated according to Equation 1:

$$\frac{(\text{Avg. Peak Area} - \text{Avg. Peak Area})(37° \text{C. Control} \quad \text{Antagonist})}{(\text{Avg. Peak Area} - \text{Avg. Peak Area})(37° \text{C. Control} \quad 0° \text{C. Control})} \quad \text{Eq. 1}$$

Referring now to the drawings and, more particularly to FIG. 1, the novel 2,4-diaryl-1,3- dithiolanes are synthesized by first converting an arylaldehyde (A) to an epoxide (B) using tert-butylammonium iodide (TBAI), trimethylsulfonium iodide, and sodium hydroxide. The epoxide (B) is then reacted with carbon disulfide, potassium hydroxide and methanol to produce a 4-aryl-1,3-dithiolane-2-thione (C) which is then reduced with lithium aluminum hydride to produce a 1-aryl-1,2- ethanedithiol (D). The 1-aryl-1,2-ethanedithiol is then reacted with an arylaldehyde (E), which can be the same as the starting reactant, by cyclizing with pyridinium para-toluene sulfonate (PPTS) or camphor sulfonic acid. The cyclizing reaction produces 2,4- diaryl-1,3- dithiolane compounds (F) in a mixture of 1:1 to 3:1 cis:trans isomers depending on the respective catalyst. The cis and trans isomers can be obtained by successive recrystallizations in methanol, hexane/ethyl acetate, or dichloromethane/hexane.

The following examples describe the synthesis of a number of compounds which have been produced and relate particularly to FIG. 1 where the intermediate compounds are identified by numbers 24–43 and the 2,4-diaryl-1,3- dithiolane compounds produced are identified by numbers 1–21. Details on particular compounds that may also be synthesized according to the scheme of FIG. 1 are also provided; however, it should be understood that compounds within the scope of this invention can be synthesized by routes other than those outlined in the following examples and that compounds with different combinations of substituents on the aryl rings are within the scope of this invention, and further that the dithiolane ring can be substituted with moieties other than hydrogen, e.g., halogens, haloloweralkyls, —$CONR^2R^3$ wherein $R^2$ and $R^3$ independently represent $C_{1-10}$ alkyl and hydrogen, loweralkenyl, —$COR^2$, $CH_2OR^2$, lower alkynyl —$CH_2NR^2R^3$ or —$CH_2SR^2$, in a manner similar to that described in U.S. Pat. No. 4,539,332 which is herein incorporated by reference.

EXAMPLE 1

Cis and trans-2,4-bis-(3,4,5-trimethoxyphenyl)-1,3-dithiolane (compound 1)

Step A: Preparation of 1-(3,4,5-trimethoxyphenyl)oxirane (28)

3,4,5-trimethoxybenzaldehyde (24) (9.80g, 50.0 mmole) is dissolved in 20 ml $CH_2Cl_2$ along with tetrabutylammonium iodide (0.396 g, 1.00 mmole). To this solution is added a cooled 50% NaOH solution (10 g NaOH in 10 ml $H_2O$). To this mixture is added trimethysulfonium iodide (10.20 g, 50.0 mmole). The reaction is refluxed with vigorous stirring for 15 hours. The reaction is quenched with $H_2O$, extracted with $CH_2Cl_2$, washed with brine, dried over $MgSO_4$ and evaporated to an oil (9.69 g, 84%) which solidifies to a white solid after 24 hours in vacuo.

NMR: ($CDCl_3$) 2.75,dd,1H;3.11,dd,1H;3.81,d,1H; 3.82,s,3H;3.85,s,6H;6.50,s,2H M.S. (CI) :211 (100%). Melting Point: 54.5°–56° C. C,H Analysis: (theoretical, actual) C (62.85,62.63); H (6.71,6.76).

Step B: Preparation of 4-(3,4,5-trimethoxyphenyl)-1,3-dithiolane-2-thione (32)

Powdered potassium hydroxide (2.40 g, 42.85 mmole) is dissolved in 10.0 ml methanol and carbon disulfide (3.10 ml, 51.43 mmole) is added at 0° C. under an $N_2$ atmosphere. The reaction mixture is shaken vigorously and 1-(3,4,5-trimethoxyphenyl) oxirane (28) (3.50 g, 16.66 mmole) is added. The reaction is allowed to warm to room temperature at which point the reaction starts to reflux for twenty minutes. Subsequently, the reaction is stirred at room temperature overnight. A yellow precipitate is isolated by suction filtration and is washed with $H_2O$ and diethylether to yield 3.82 g (76%).

NMR: ($CDCl_3$) 3.85,s,3H;3.88,s,6H;3.99,dd,1H; 4.17,t,1H;5.57,dd,1H;6.70,s,2H. M.S.: (IBu) 303 (100%). Melting Point: 152°–154° C. C,H,S Analysis: (theoretical, actual) C (47.66,47.90); H (4.67,4.70); S (31.80,31.71).

Step C: Preparation of 1-(3,4,5-trimethoxyphenyl)-1,2-ethanedithiol (38)

Lithium aluminum hydride (0.20 g, 5.27 mmole) is added to 15 ml dry diethylether. To this slurry is added 4-(3,4,5-trimethoxyphenyl)-1,3-dithiolane-2-thione (32) (1.0 g, 3.31 mmole) predissolved in 20 ml dry THF. The reaction is refluxed under an $N_2$ atmosphere for 12 hours. The reaction is cooled to 0° C. and the excess hydride destroyed with $H_2O$. The reaction mixture is acidified with 10% HCl and immediately extracted with diethyl ether. The organic layer is washed with $H_2O$, dried over $MgSO_4$, filtered and evaporated to a white solid (9.836 g, 97%). NMR: ($DCDl_3$) 2.34,d,1H;2.95,m,1H;3.09,m,1H; 3.84,s,3H;3.87,s,6H;4.03,m,1H;6.53,s,2H. M.S. (IBu) 261 (100%). Melting Point: 72.5°–73.5° C. C,H,S Analysis: (theoretical, actual) C (50.74,50.85); H (6.19,6.20); S (24.63,24.53).

Step D: Preparation of cis and trans-2,4-bis-(3,4,5-trimethoxyphenyl)-1,3-dithiolane (new compound 1)

1-(3,4,5-trimethoxyphenyl)-1,2-ethanedithiol (38) (0.56 g, 2.15 mmole), 3,4,5-trimethoxybenzaldehyde (24) (0.35 g, 1.78 mmole) and 0.178 g of pyridinium paratoluene sulfonate are added to 40 ml dry benzene and refluxed with Dean-Stark removal of the benzene-water azeotrope for 24 hours. The benzene is removed in vacuo, and the remaining oil redissolved in ethyl acetate. The organic layer is washed with $H_2O$ and was dried over $MgSO_4$, filtered, and evaporated in vacuo to a white foam which is purified by flash column chromatography using 1:1 hexane/ethyl acetate as eluent (0.630 g, 81%). The trans isomer is isolated from the 1:1 mixture of diastereomers after three recrystallizations from methanol (25 mg). If the above reaction is performed under reduced pressure (aspirator) at 45° C. for 2.5 hours using camphor sulfonic acid as the catalyst, the product mixture contains a 3:1 cis/trans ratio of diastereomers. The cis diastereomer is isolated from this product mixture by recrystallization from either methanol or hexane/ethyl acetate.

Trans epimer:

NMR: (CDCl$_3$): 3.48,dd,1H;3.65,dd,1H;3.84,s,6H; 3.88, s,12H;5.06,dd,1H;5.83,s,1H;6.72,s,2H;6.83,s,2H. M.S. (CI): 439 (100%) Melting Point: 111° C. C,H,S Analysis: (theoretical, actual) C (57.51,57.57); H (5.97,5.98); S (14.62,14.52).

Cis epimer:

NMR: (CDCl$_3$): 3.55–3.58,d,2H;3.84–3.87,3s,18H; 4.84, t,1H;5.75,s,1H;6.75,s,2H;6.86,s,2H. M.S. (CI): 439 (100%) Melting Point: 100°–101° C. C,H,S Analysis: (theoretical, actual) C (57.51,57.40); H (5.97,6.00); S (14.62,14.68).

EXAMPLE 2

2-(3-hydroxy-4,5-dimethoxyphenyl )-4-(3,4,5-trimethoxyphenyl)-1,3-dithiolane (compound 2) (M.S. (CI): 425,195 (100%);

2-(3-benzoyloxy-4,5-dimethoxyphenyl)-4-(3,4,5-trimethoxyphenyl)-1,3-dithiolane (compound 3) (M.S. (CI): 529,195 (100%);

2-(3-methoxymethoxy-4,5-dimethoxyphenyl)-4-(3,4,5-trimethoxyphenyl)-1,3-dithiolane (compound 4) (M.S. (CI) :469,195 (100%);

Trans 2-(4-hydroxy-3,5-dimethoxyphenyl)-4-(3,4,5-trimethoxyphenyl)-1,3-dithiolane (compound 5) (C.H.S. Analysis (theoretical, actual) C (56.58,56.68), H (5.70, 5.71), S (15.10,15.04);

Trans 2-(4-hydroxy-3-nitro-5-methoxyphenyl)-4-(3,4,5-trimethoxyphenyl)-1,3-dithiolane (compound 6) (C.H.S. Analysis (theoretical, actual) C (51.92,52.03), H (4.82, 4.86), S (14.59,14.51);

Trans 2-(4-hydroxy-3-iodo-5-methoxyphenyl)-4-(3,4,5-trimethoxyphenyl)-1,3-dithiolane (compound 7) (C.H.S Analysis (theoretical, actual) C (43.85,43.93), H (4.07, 4.09), S (12.32,12.42));

Trans 2-(4,5-dimethoxy-3-iodophenyl)-4-(3,4,5-trimethoxyphenyl)-1,3-dithiolane (compound 8) (M.S. (CI):535,195 (100%));

Trans 2-(4-hydroxy-3,5-dimethoxyphenyl)-4-(3,4,5-trimethoxyphenyl)-1,3-dithiolane (compound 9) (C.H.S. Analysis (theoretical, actual) C (61.20,61.08), H (6.16, 6.20), S(16.34,16.44)); and Trans 2-(4-hydroxy-3,5-dimethylphenyl)-4-(3,4,5-trimethoxyphenyl)-1,3-dithiolane (compound 10) (C.H.S. Analysis (theoretical, actual) C(65.51,65.50), H(7.61, 7.64), S(13.45,13.55)) are prepared following substantially the same procedures as described in Example 1; however, the constituents of the arylaldehyde (E) are different for each of the new compounds 2–10. Specifically, the 2,4-diaryl-1,3-dithiolanes (F) have the following constituents:

| Compound | A | B | C |
|---|---|---|---|
| 2 | OH | OCH$_3$ | OCH$_3$ |
| 3 | OCOPh | OCH$_3$ | OCH$_3$ |
| 4 | OCH$_3$OCH$_3$ | OCH$_3$ | OCH$_3$ |
| 5 | OCH$_3$ | OH | OCH$_3$ |
| 6 | NO$_2$ | OH | OCH$_3$ |
| 7 | I | OH | OCH$_3$ |
| 8 | I | OCH$_3$ | OCH$_3$ |
| 9 | CH$_3$ | OH | CH$_3$ |
| 10 | t-butyl | OH | t-butyl |

The aryladehydes (E) utilized are either commercially available or synthesizable by well known procedures.

EXAMPLE 3

Trans 2,4-bis-(3,5-dimethoxy-4-hydroxyphenyl)-1,3-dithiolane (compound 11) and Trans 2-(3,4,5-trimethoxyphenyl)-4-(3,5-dimethoxy-4-hydroxyphenyl)-1, 3-dithiolane (compound 12) are prepared according to the scheme shown in FIG. 1.

Step A: Preparation of 1-(3,5-dimethoxy-4-methoxymethoxyphenyl) oxirane (29)

3,5-dimethoxy-4-methoxymethoxybenzaldehyde (25) [55211-66-0] (10.85 g, 48.0 mmole) is dissolved in 20 ml CH$_2$Cl$_2$ along with tetrabutylammonium iodide (0.40 g, 1.00 mmole). To this solution is added a cooled 50% NaOH solution (10 g NaOH in 10 ml H$_2$O). To this mixture is added trimethylsulfonium iodide (10.77 g, 52.81 mmole). The reaction is refluxed with vigorous stirring for 48 hours. The reaction is quenched with H$_2$O, extracted with CH$_2$Cl$_2$, washed with brine, dried over MgSO$_4$ and evaporated to an oil (9.69 g, 84%). The oil can be crystallized from hexane/ethyl acetate. NMR: (CDCl$_3$) 2.70,m,1H; 3.10,m,1H;3.60, s,3H;3.90,s,6H;5.09,s,2H;6.50,s,2H.

Step B: Preparation of 4-(3,5-dimethoxy-4-methoxymethoxyphenyl)-1,3-dithiolane-2-thione (33)

Powdered potassium hydroxide (1.75 g, 31.25 mmole) is dissolved in 3.0 ml methanol and carbon disulfide (2.85 g, 37.5 mmole) was added at 0° C. The reaction mixture is shaken vigorously and 3,5-dimethoxy-4-methoxymethoxyphenyloxirane (29) (3.0 g, 12.5 mmole) is added. The reaction is allowed to warm to room temperature at which point the reaction starts to reflux. The reaction is stirred at room temperature for 24 hours, and is quenched with ethyl acetate and 10% NaOH. The organic layer is washed with 3×40 ml 10% NaOH, 1×30 ml H$_2$O, 2×30 ml ss NaCl, dried over MgSO$_4$, and evaporated in vacuo to a yellow oil which is purified by flash column chromatography using 2:1 hexane/ethyl acetate. The product was recrystallized from hexane/ethyl acetate (4.52 g, 63% yield).

NMR: (CDCl$_3$) 3.59,s,3H;3.86,s,6H;3.98,dd,1H; 4.16,dd, 1H;5.12,s,2H;5.58,dd,1H;6.70,s,2H. M.S.: (IBu) 333 (100%) Melting Point: 97.5°–99° C. C,H,S Analysis: (theoretical, actual) C (46.97,47.06); H (4.85,4.88); s (28.93, 28.83).

Step B2: Preparation of 4-(3,5-dimethoxy-4-hydroxyphenyl)-1,3-dithiolane-2-thione (34)

Powdered potassium hydroxide (3.50 g, 62.50 mmole) is dissolved in 6.0 ml methanol and carbon disulfide (5.70 g, 75.0 mmole) is added at 0° C. The reaction mixture is shaken vigorously and 3,5-dimethoxy-4-methoxymethoxyphenylxirane (29) (6.0 g, 25.0 mmole) is added. The reaction is allowed to warm to room temperature at which point the reaction starts to reflux. The reaction is stirred at room temperature for 24 hours, and is quenched with ethyl acetate and 10% NaOH. The organic layer is washed with 3×40 ml 10% NaOH, 1×30 ml H$_2$O, and 2×30 ml ss NaCl. The ethyl acetate is reduced to 10 ml and 30 ml methanol along with 10 ml 5.0M methanolic HCl. The reaction is stirred for three hours, quenched with 100 ml H$_2$O, extracted with ethyl acetate, dried over MgSO$_4$, and evaporated in vacuo to a yellow oil which is purified by flash column chromatography using 2:1 hexane/ethyl acetate. The product is recrystallized from hexane/ethyl acetate (4.52 g, 63% yield).

NMR: (CDCl$_3$) 3.91,s,6H;3.97,t,1H; 4.16,t,1H;5.58,dd, 1H;5.60,s,1H;6.71,s,2H. M.S.: (CI) 289 (100%). Melting Point: 96°–97° C. C,H,S Analysis: (theoretical, actual) C (45.81,45.91); H (4.19,4.22); S(33.35,33.25).

Step C1: Preparation of 1-(3,5-dimethoxy-4-methoxymethoxyphenyl)-1,2-ethanedithiol (39).

Lithium aluminum hydride (0.622 g, 16.38 mmole) is added to 60 ml dry diethyl ether. To this slurry is added dropwise 4-(3,5-dimethoxy-4-methoxymethoxyphenyl)-1,3-dithiolane-2-thione (33) (3.40 g, 10.24 mmole) predissolved in 35 ml dry THF. The reaction is stirred under an N$_2$ atmosphere until the solution becomes colorless (4 hours). The reaction is cooled to 0° C. and the excess hydride destroyed with H$_2$O. The reaction mixture is acidified with 10% HCl and immediately extracted with diethyl ether. The organic layer is washed with H$_2$O, dried over MgSO$_4$, filtered and evaporated to a white solid (2.47 g, 84%). NMR: (CDCl$_3$) 2.33,d,1H;2.90,m,1H;3.10,m,1H; 3.59,s,3H;3.85,s, 6H;4.03,m,1H;5.10,s,2H;6.53,s,2H Melting Point: 84°–85° C. C,H,S analysis: (theoretical, actual) C (49.63,49.52); H (6.25,6.28); S (22.08,22.16).

Step C2: Preparation of 1-(3,5-dimethoxy-4-hydroxyphenyl)-1,2-ethanedithiol (40)

Lithium aluminum hydride (0.553 g, 14.58 mmole) is added to 10 ml dry diethyl ether and 10 ml dry THF. To this slurry is added dropwise 4-(3,5-dimethoxy-4-hydroxyphenyl)-1,3-dithiolane-2-thione (34) (2.00 g, 6.94 mmole) predissolved in 40 ml dry THF. The reaction is stirred under a nitrogen (N$_2$) atmosphere until the solution becomes colorless (1 hour). The reaction is cooled to 0° C. and the excess hydride destroyed with H$_2$O. The reaction mixture is acidified with 10% HCl and immediately extracted with diethyl ether. The organic layer was washed with H$_2$O, dried over MgSO$_4$, filtered and evaporated to a white solid (1.64 g, 96%).

NMR: (CDCl$_3$) 2.33,d,1H;2.93,m,1H;3.10,m,1H; 3.90,s, 9M;4.03,m,1H;5.50,s,1H;6.54,s,2H. M.S. (CI): 247,213 (100%)

Step D1: Preparation of trans-2,4-bis-(3,5-dimethoxy-4-hydroxyphenyl)-1,3-dithiolane (compound 11)

1-(3,5-dimethoxy-4-hydroxyphenyl)-1,2-ethanedithiol (40) (2.46 g, 10.0 mmole), 3,5-dimethoxy-4-hydroxybenzaldehyde (indicated as arylaldehyde E in FIG. 1) (1.32 g, 7.20 mmole) and 1.00 g of pyridinium paratoluene sulfonate are added to 50 ml dry benzene and refluxed with Dean-Stark removal of the benzene-water azeotrope overnight. The benzene is removed in vacuo, and the remaining oil redissolved in dichloromethane. The organic layer is washed with 10% NaHCO$_3$ and H$_2$O. The organic layer is dried over MgSO$_4$, filtered, and evaporated in vacuo to a white solid which is recrystallized from methanol (2.510 g, 85%). The trans isomer (0.683 g) is isolated by recrystallization from methanol. NMR: (CDCl$_3$) 3.45,dd,1H;3.61, dd,1H; 3.91,s,6H;3.92,s,6H;5.07,dd,1H;5.50,d,2H;5.83,s, 1H; 6.73,s,2H;6.84,s,2H. M.S.: (CI) 411 (100%). Melting Point: 169°–170° C. C,H,S Analysis: (theoretical, actual) C (55.59,55.58); H (5.40,5.44); S (15.62,15.56).

Step D2: Preparation of 2-(3,4,5-trimethoxyphenyl)-4-(3,5-dimethoxy-4-hydroxyphenyl)-1,3-dithiolane (compound 12)

1-(3,5-dimethoxy-4-hydroxyphenyl)-1,2-ethanedithiol (40) (2.10 g, 8.54 mmole), 3,4,5-trimethoxybenzaldehyde (24) (1.28 g, 6.57 mmole) and 0.857 g of pyridinium paratoluene sulfonate are added to 60 ml dry benzene and refluxed with Dean-Stark removal of the benzene-water azeotrope overnight. The benzene is removed in vacuo, and the remaining oil is extracted into 10% NaOH which was washed with diethylether. The basic layer is reacidified with 10% HCl and the desired product is extracted into ethyl acetate. The organic layer is dried over MgSO$_4$, filtered, and evaporated in vacuo to an oil which is purified by flash column chromatography with 2:1 hex/ethyl acetate as eluent. The product mixture contains a 1.0/1.2 cis/trans ratio after the first recrystallization (1.287 g, 59%). The trans isomer is isolated after six additional recrystallizations from methanol.

NMR: (CDCl$_3$) 3.50,dd,1H;3.61,dd,1H;3.84.,s,3H; 3.89, s,6H;3.91,s,6H;5.06,dd,1H;5.51,s,1H;5.82,s,1H; 6.73,s, 2H;6.83,s,2H. M.S.: (CI) 425 (100%) 212. Melting Point: 129°–130° C. C,S Analysis: (theoretical, actual) C (56.58, 56.52); H (5.70,5.74).

EXAMPLE 4

Trans-2-(3,5-dithiomethyl-4-hydroxyphenyl)-1,3-dithiolane (Compound 13A (FIGS. 1 and 2))

3,5-dithiomethyl-4-hydroxybenzaldehyde (26) (0.822 g, 3.84 mole), which is described in European Pat. No. Application 0,319,947, Jul. 12, 1988, to the Green Cross Corporation and which is herein incorporated by reference, 1-(3, 4,5-trimethoxyphenyl)-1,2-ethane dithiol (38) (1.20 g, 4.61 mmole) and 0.460 g of pyridinium paratoluene sulfonate are added to 45 ml dry benzene and refluxed with Dean-Stark removal of the benzene-water azeotrope overnight. The benzene is removed in vacuo, and the remaining oil redissolved in ethyl acetate. The organic layer is washed with 10% NaHCO$_3$ and H$_2$O. The organic layer is dried over MgSO$_4$, filtered, and evaporated in vacuo to an oil which is purified by flash column chromatography with 2:1 hex/ethyl acetate as eluent. 621 mg of product crystallize out of the column fractions as a 1.4/1.0 trans/cis mixture. (Total yield= 1.428 g, 82%). The trans epimer is isolated as a 6/1 trans/cis mixture.

Trans epimer: NMR: (CDCl$_3$) 2.42,s,6H;3.47,dd,2H; 3.65,dd,2H;3.84,s,3H;3.88,s,6H;5.06,dd,1H;5.79,s,1H; 6.72,s, 2H;7.08,s,1H;7.48,s,2H. M.S. (CI): 457 (100%) Melting Point: 144°–145° C. C,H,S Analysis: (theoretical, actual) C (52.60,52.59); H (5.30,5.34); S (28.08,27.98).

2,4-bis-(3,5-dithiomethyl-4-hydroxyphenyl)-1,3-dithiolane (compound 13b in FIG. 2), 2,4-bis-(3,5-dithiomethyl-4-methoxyphenyl)-1,3-dithiolane (compound 13c in FIG. 2), and 2-(3,5-dithiomethyl-4-methoxyphenyl)-4-(3,5-dithiomethyl-4-hydroxyphenyl)-1,3-dithiolane (compound 13e of FIG. 2) have not yet been prepared but could be prepared as described above using 3,5-dithiomethyl-4-methoxymethoxybenzaldehyde (27) as the starting material. Similarly, 2-(3,5-dithiomethyl-4-hydroxyphenyl)-4-(3,5-dithiomethyl-4-methoxyphenyl)-1, 3-dithiolane (compound 13d of FIG. 2) has not yet been prepared but could be prepared as described above using 3,5-dithiomethyl-4-hydroxybenzaldehyde as a starting material.

EXAMPLE 5

Trans-2-(3-(2-hydroxyethylsufonyl)-5-methoxy-4-propoxyphenyl)-4-(3,4,5-trimethoxyphenyl)-1,3-dithiolane (compound 14)

Step A: Preparation of 3-(2-hydroxyethylthio)-5-methoxy-4-propoxybenzaldehyde 5-iodo-3-methoxy-4-propoxybenzaldehyde (6.166 g, 19.27 mmole), copper powder (10.41 g, 163.78 mmole), and 45 ml dimethylformamide (DMF) are stirred vigorously under a $N_2$ atmosphere at 140° C. for 3 hours. To this slurry is added 2-hydroxy ethyldisulfide (4.75 g, 30.8 mmole) predissolved in 10 ml DMF. The reaction is stirred at 140° C. overnight. The copper is removed by suction filtration through celite, and is washed thoroughly with ethyl acetate. The filtrate is concentrated to an oil in vacuo and then redissolved in dichloromethane. The organic layer is washed with $H_2O$, dried over magnesium sulfate, and concentrated to an oil in vacuo which is purified by flash column chromatography using 1:1 hex/ethyl acetate as eluent to yield a light yellow oil (4.00 g, 77%).

NMR: ($CDCl_3$) 1.06,t,3H;1.85,m,2H;3.13,t,2H;3.74,t,2H; 3.91,s,3H;4.08,t,2H;7.31,d,1H;7.46,d,1H;9.86,s,1H. M.S. (CI): 271 (100%).

Step B: Preparation of 2-(3-(2-hydroxyethylthio)-5-methoxy-4-propoxyphenyl)-1,3-dioxalane 3-(2-hydroxyethylthio-3-methoxy-4-propoxybenzaldehyde (0.738 g, 2.73 mmole), ethylene glycol (0.678 g, 10.92 mmole), PPTS (0.274 g, 1.09 mmole) and 40 ml dry benzene are refluxed with Dean-Stark removal of the benzene-water azeotrope for five hours. The benzene is removed in vacuo and the remaining oil redissolved in $CH_2Cl_2$ which is washed with 10% $NaHCO_3$, $H_2O$ and dried over sodium sulfate. The solvent is removed in vacuo and the oil purified by flash column chromatography using 2:1 hex/ethyl acetate as eluent to yield a light tan oil (0.616 g, 71%). NMR: ($CDCl_3$) 1.03,t,3H;1.84,m,2H;3.05, t,2H; 3.66,t,2H;3.85,s,3H;3.95,t,2H;4.07,m,4H;5.71,s,1H; 6.93,d,1H;7.08,d,1H.

Step C: Preparation of 3-(2-hydroxyethylsulfonyl)-5-methoxy-4-propoxybenzaldehyde 2-(3-(2-hydroxyethylthio)-5-methoxy-4-propoxyphenyl)-1,3-dioxalane (2.11 g, 6.70 mole) is dissolved in 15 ml $CH_2Cl_2$ and is cooled to 0° C. under an $N_2$ atmosphere. To this solution is slowly added 80% metachloroperoxybenzoic acid (MCPBA) (3.32 g, 15.41 mmole) along with an additional 10 ml $CH_2Cl_2$. The reaction is allowed to warm to room temperature over a six hour period. The m-chlorobenzoic acid precipitate is removed by suction filtration and the filtrate is washed with 10% $NaHCO_3$ and $H_2O$. The organic layer is then added to 20 ml 10% HCl and the mixture is stirred vigorously overnight. The organic layer is separated, dried over $MgSO_4$, and evaporated to an impure white solid which is purified by flash column chromatography using 2:1 hexane/ethyl acetate as eluent no yield a white solid (1.20 g, 60%).

NMR: ($CDCl_3$) 1.03,t,3H;1.88,m,2H;2.70,brs,1H;3.65,t, 2H;3.96,s,3H;3.98,t,2H;4.24,t,2H;7.68,d,1H;7.80, d,1H;9.93,s,1H. M.S. (IBu) 302 (100%). Melting Point: 111°–112° C. C,H,S Analysis: (theoretical, actual) C (51.64, 51.67); H (6.00,5.99); S (10.60,10.52).

Step D: Preparation of 2-(3-(2-hydroxyethylsulfonyl)-5-methoxy-4-propoxyphenyl)-4-(3,4,5-trimethoxyphenyl)-1, 3-dithiolane (Compound 14 on FIG. 2)

1-(3-(2-hydroxyethylsulfonyl)-5-methoxy-4-propoxybenzaldehyde (0.409 g, 1.35 mmole), 1-(3,4,5-trimethoxyphenyl)-1,2-ethane dithiol (0.50 g, 2.03 mmole) and 0.203 g of pyridinium paratoluene sulfonate is added to 45 ml dry benzene and refluxed with Dean-Stark removal of the benzene-water azeotrope overnight. The benzene is removed in vacuo, and the remaining oil redissolved in dichloromethane. The organic layer is washed with 10% $NaHCO_3$ and $H_2O$. The organic layer is dried over $MgSO_4$, filtered, and evaporated in vacuo to an oil which is purified by flash column chromatography with 2:1 hex/ethyl acetate as eluent. The product mixture (white foam) contains a 1.0/1.2 cis/trans ratio (0.370 g, 52%). Trans/cis epimers:

NMR: ($CDCl_3$) 1.04,t,6H;1.87,m,4H;3.45–3.60,m, 4H; 3.64,t,4H;3.92,s,12H;3.95,s,6H;3.97,t,4H;4.12,t,4H; 4.88, dd,1H;5.07,dd,1H;5.53,s,2H;5.74,s,1H;5.82,s,1H; 6.73,s, 2H;6.76,s,2H;7.41,d,1H;7.43,d,1H;7.71,d,1H; 7.80,d,1H. M.S. (IBu): 544 (100%) C,H,S Analysis: (theoretical, actual) C (52.92,52.72); H (5.92,5.89); S (17.66,17.53).

EXAMPLE 7

Following substantially the same procedure as described in Example 6, 2-(3-methylsulfonyl-5-methoxy-4-propoxyphenyl)-4-(3,4,5-trimethoxyphenyl)-1,3-dithiolane (compound 15 on FIG. 2) (C.H.S. Analysis (theoretical, actual) C (53.67,53.75); H (5.88,5.93); S(18.69,18.75)), 2-(4,5-dimethoxy-3-(2-hydroxyethylsulfonyl)phenyl)-4-(3, 4,5-trimethoxyphenyl)-1,3-dithiolane (compound 16 on FIG. 2) (M.S. (IBu) 517,263 (100%)), and 2-(3-(2-(p-nitrobenzoate)ethylsulfonyl)-5-methoxy-4-propoxyphenyl)-4-(3,4,5-trimethoxyphenyl)-1,3-dithiolane (compound 17 on FIG. 2) (C.H.S. Analysis (theoretical, actual) C (53.67, 53.75); H (5.08,5.10); S (13.86,13.78)) are prepared.

EXAMPLE 8

Trans-2-(3,5-dimethoxy-4-(2-hydroxyethoxy))-4-(3, 4,5-trimethoxyphenyl)-1,3-dithiolane (compound 18 of FIG. 2)

Step A: Preparation of 3,5-dimethoxy-4-(2-hydroxyethoxy) benzaldehyde

Syringaldehyde (1.0 g, 5.49 mmole), 2-iodo-1-ethanol (1.90 g, 10.98 mmole) and potassium carbonate (1.90 g, 13.77 mmole) are added to 15 ml dry DMF and stirred for 24 hours at 80° C. under an argon atmosphere. The reaction mixture is added to 100 ml $H_2O$ and acidified with 10% HCl. The product is extracted into $CHCl_3$, dried over $MgSO_4$, and concentrated to an oil in vacuo. The remaining oil is purified by flash column chromatography using 1:1 hex/ethyl acetate as eluent (1.009 g, 81%).

NMR: ($CDCl_3$) 3.23,t,1H;3.73,m,2H;3.93,s,6H; 4.20,t, 2H;7.13,s,2H;9.87,s,1H M.S. (CI): 227 (100%).

Step B: Preparation of trans-2-(3,5-dimethoxy-4-(2-hydroxyethoxy))-4-(3,4,5-trimethoxyphenyl)-1,3-dithiolane 3,5-dimethoxy-4-(2-hydroxyethoxy) benzaldehyde (2.14 g, 9.47 mmole), 1-(3,4,5-trimethoxyphenyl)-1,2-ethane dithiol (2.54 g, 9.77 mmole) and 1.00 g of pyridinium paratoluene sulfonate is added to 75 ml dry benzene and refluxed with Dean-Stark removal of the benzene-water azeotrope for 24 hours. The benzene is removed in vacuo, and the remaining oil redissolved in ethyl acetate. The organic layer is washed with 10% HCl and $H_2O$. The organic layer is dried over $MgSO_4$, filtered, and evaporated in vacuo to an oil which is purified by flash column chromatography with 1:2 hex/ethyl acetate as eluent. The product mixture (white foam) triturates to a solid in diethylether (3.10 g, 70%). The trans isomer is isolated after three recrystallizations from $CH_2Cl_2$/hexane (1.00 g).

NMR: ($CDCl_3$) 3.40,t,1H;3.48,dd,1H;3.64,dd; 3.72,m, 2H;3.84,s,3H;3.88,s,6H;3.90,s,6H;4.13,t,2H;5.06,dd,

1H;5.83,s,1H;6.72,s,2H;6.85,s,2H. M.S. (CI): 469 (100%).
Melting point: 121°–122° C.

EXAMPLE 9

Following substantially the same procedure outlined in Example 8, 2-(3,5-dimethoxy-4-(3-bromopropoxyphenyl)-4-(3,4,5-trimethoxyphenyl)-1,3-dithiolane (compound 19) (M.S. (CI) 547,195 (100%)), 2-(4,5-dimethoxy-3-(2-hydoxyethoxyphenyl)-4-(3,4,5-trimethoxyphenyl)-1,3-dithiolane (compound 20) (M.S. (CI) 469, 195, 84 (100%), and 2-(4,5-dimethoxy-3-(3-hydoxypropoxyphenyl)-4-(3,4,5-trimethoxyphenyl)-1,3-dithiolane (compound 21) (M.S. (CI) 483, 195, 84 (100%)) are prepared.

Referring now to both FIGS. 1 and 2, many 2,4-diaryl-1,3-dithiolane compounds have been synthesized according to the scheme shown in FIG. 1 and discussed in Examples 1–9 and many other compounds are readily synthesizable via the same scheme. Several of these compounds have been tested for their antagonist activity for PAF induced platelet aggregation and for their inhibition of the production of leukotrienes via the 5-lipoxygenase pathway in PMN leukocytes and monocytes according to the procedures described above. FIG. 2 shows that small concentrations of these compounds can inhibit both PAF platelet aggregation and the 5-lipoxygenase pathway; therefore, these compounds would be beneficial for the treatment of the large number of diseases and disorders which are mediated by leukotrienes and PAF.

FIG. 3 shows the synthesis route for the preparation of the oxathiolane (F) analog of the diaryltetrahydrofuran L-652,731. This compound was synthesized for the purpose of comparing its antagonistic activity to compound 1 (FIGS. 1 and 2) of the present invention, which is the dithiolane (F) analog of diaryltetrahydrofuran L-652,731. 3,4,5-trimethoxystyrene (B') is formed by a Wittig reaction from 3,4,5-trimethoxybenzaldehyde (A') and methyltriphenylphosphoniumbromide. The styrene (B') was converted to the bromohydrin (C') using NBS and wet DMSO. The bromohydrin (C') was converted thiouronium salt (D'), using thiourea and subsequently hydrolyzed using sodium hydroxide to produce hydroxythiol (E'). Similar to FIG. 1, the hydroxythiol (E') was reacted in an acid catalyzed thioketal cyclization with 3,4,5-trimethoxy benzaldehyde to produce the oxathiolane (F). Of particular significance, the oxathiolane (F) was found to be a much weaker antagonist of PAF-induced platelet aggregation than the corresponding dithiolane compound which had an $IC_{50}$ value of less than 1 µM.

Figure 4A:
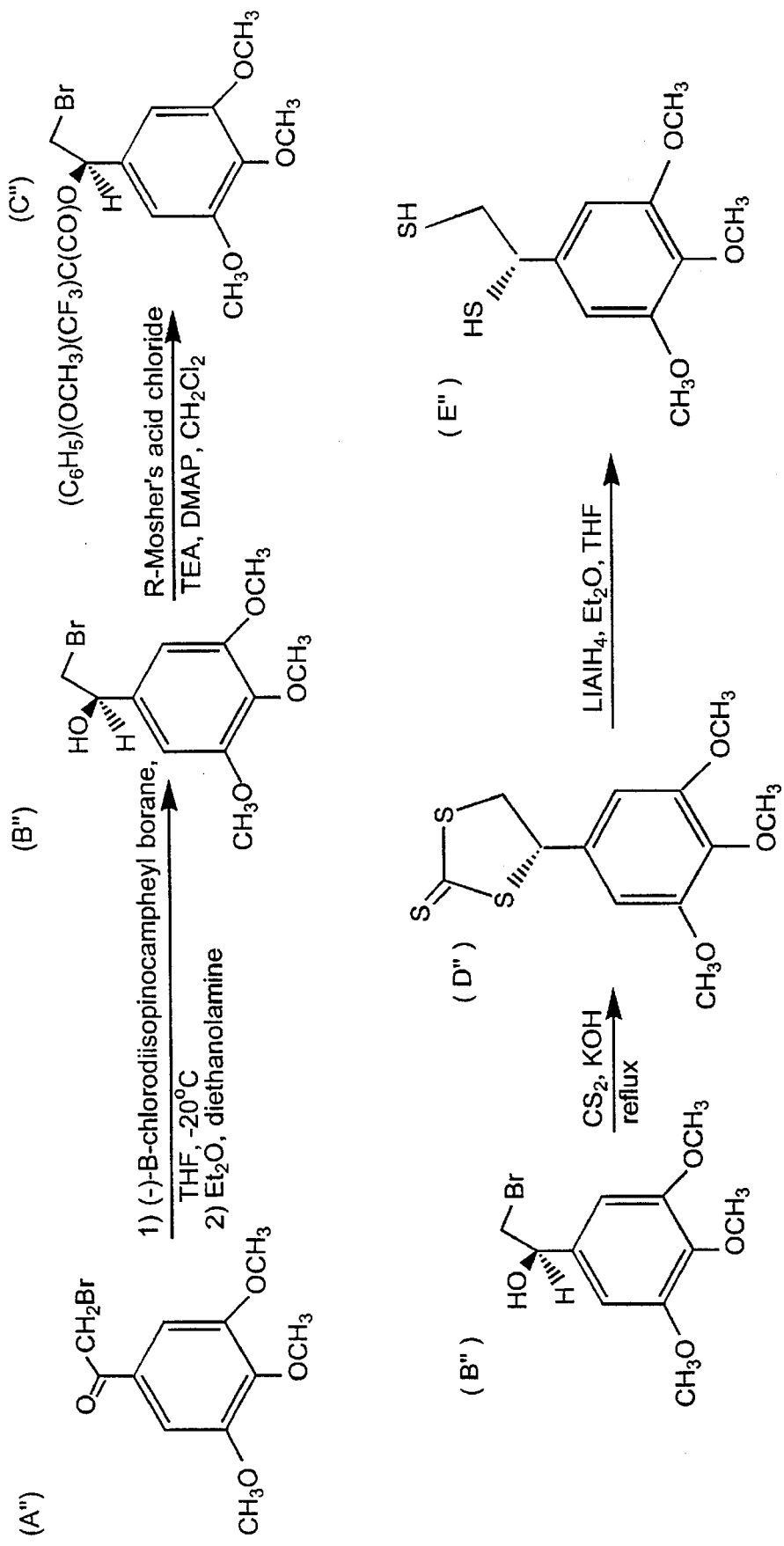
FIG. 4 is a schematic drawing showing a synthetic pathway for producing a single enantiomer of a 2,4-diaryl-1,3-dithiolane compound.
Figure 4B:
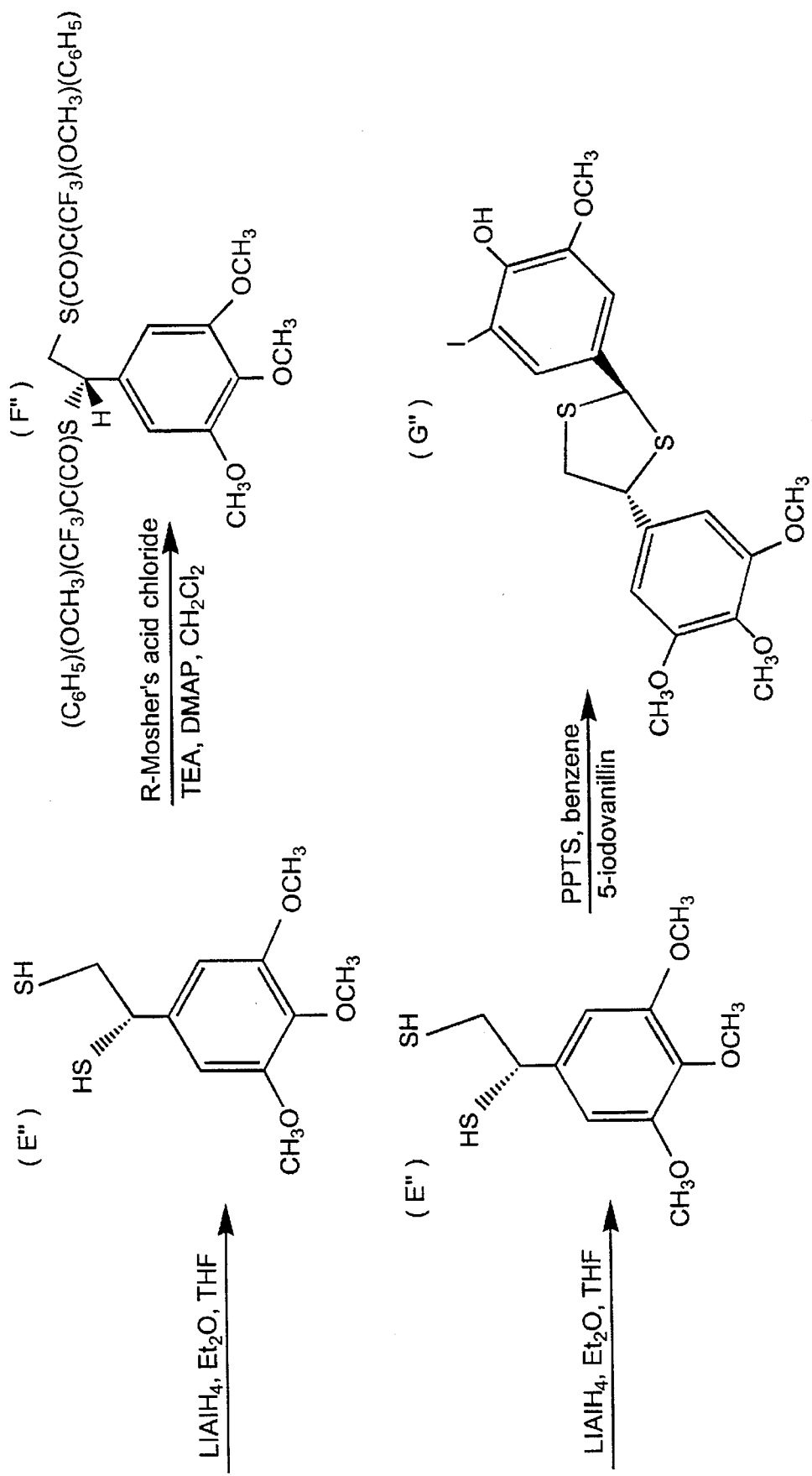

FIG. 4 shows a procedure for preparing R,S-enantiomer of compound 7 (FIGS. 1 and 2 show the preparation of a racemic mixture of compound 7, specifically, (R,S)-Trans-2-(4-hydroxy-5-iodo-3-methoxyphenyl)-4-(3,4,5-trimethoxyphenyl)-1,3-dithiolane. The importance of testing potential drugs in both their racemic and enantiomeric form has received increasing attention in the scientific community. Jamali et al., in *J. Pharm. Sci.*, 78. 695 (1989), demonstrated than the pharmokinetic and pharmodynamic interactions of a racemic drug is more complex than the sum of the contributions of the individual enantiomers. In a racemic mixture, the inactive enantiomer may agonize or antagonize pharmocologic and/or toxicologic activities. Thus, it may be preferable to use a single enantiomer for therapeutic applications. Example 10 describes the synthetic process shown in FIG. 4.

EXAMPLE 10

(R,S)-Trans-2-(4-hydroxy-5-iodo-3-methoxyphenyl)-4-(3,4,5-trimethoxyphenyl)-1,3-dithiolane Step A: Preparation of 2-bromo-1-(3,4,5-trimethoxyphenyl)ethanone (A")

Freshly pulverized copper bromide (15.00 g, 67.82 mole) is refluxed in 50 ml chloroform 3,4,5-trimethoxyacetophenone (7.50 g, 35.67 mmole) predissolved in 50 ml chloroform is added and the reaction refluxed overnight. The copper bromide is removed by filtration through celite and the solvent removed in vacuo to leave a dark yellow-brown oil. Crystallization of this oil has been unsuccessful and the product is purified by flash column chromatography using 2:1 hex/ethyl acetate as eluent (7.90 g, 77%). 1-(3,4,5-trimethoxyphenyl)-2,2-dibromoethanone is isolated as a minor side product.

NMR: ($CDCl_3$) 3.93,s,6H;3.94,s,3H;4.41,s,2H;7.24,s,2H Melting Point: 67°–68° C.

Step B: Preparation of (R)-2-bromo-1-(3,4,5-trimethoxyphenyl) ethanol (B")

2-bromo-1-(3,4,5-trimethoxyphenyl)ethanone (A1) (7.90 g, 27.33 mmole) is dissolved in 50 ml dry THF and is cooled to –20° C. under an $N_2$ atmosphere. To this solution is added (–)-B-chlorodiisopino campheylborane (14.90 g, 46.50 mmole) predissolved in 50 ml dry THF. The reaction is stirred at –20° C. for 6 hours. THF is removed in vacuo and the remaining oil redissolved in diethyl ether. To this solution is added diethanolamine (7.33 g, 69.75 mmole) and is stirred overnight. The solid is removed by filtration and the filtrate washed with $H_2O$, dried over $MgSO_4$, filtered and evaporated to an oil which is purified by flash column chromatography using 2:1 hex/ethyl acetate as eluent in order to remove the pinene side product. (6.268 g, 79%: $[\alpha]^{21}D=-28.0^s$ 1% $CHCl_3$). After one recrystallization from ether/hexane, the rotation increased to $[\alpha]^{21}D=30.40^s$ 1% $CHCl_3$ (5.50 g, 69%).

NMR: ($CDCl_3$) 2.71,d,2H;3.51,dd,1H;3.62,dd,1H; 3.82, s,3H;3.86,s,6H;4.85,ddd,1H;6.60,s,2H. M.S.: (IBu) 292, 290,273. Melting Point: 79°–80° C. C,H,Br Analysis: (theoretical, actual) C (45.38,45.44), H (5.19,5.22), Br (27.45,27.36).

The Mosher ester derivation of (R)-2-bromo-1-(3,4,5-trimethoxyphenyl) ethanol (C") was prepared as follows to determine the optical purity. (R)-2-bromo-1-(3,4,5-trimethoxyphenyl) ethanol (B") (0.025 g, 0.086 mmole), (R) (+)-α-methoxy-α-(trifluoromethyl) phenylacetic acid chloride (0.024 g, 0.094 mmole), dimethylaminipyridine (0.001 g, 0.11 equivalents), triethylamine (0.022 g, 0.215 mmole) and 5 ml dry dichloromethane are stirred at room temperature for 12 hours. The solvent is removed in vacuo, and the remaining oil redissolved in 0.025 ml ethyl acetate. This solution is added to a micro flash silica column in a disposable pasteur pipette and the product eluted with 2:1 hex/ethyl acetate (0.040 g, 92%). By $^1$H-NMR, the ratio of RR/RS diasteriomers is 67/1–97% ee.

NMR: ($CDCl_3$) 3.57,dd, 1H;3.68,dd,1H;3.69,s,6H; 3.70, d,3H;3.83,s,3H;6.04,dd,1H;6.36,s,2H;7.3–7.45,m, 5H. $[\alpha]^{21}D=-28.4^m$ 1% $CHCl_3$ M.S.: (IBu) 508,275,273 (base). Melting Point: 99°–101° C. C,H Analysis: (theoretical, actual) C (49.72,49.81), H (4.37,4.40).

Step C: Preparation of (S)-4-(3,4,5-trimethoxyphenyl)-1,3-dithiolane-2-thione (D")

Lithium hydroxide monohydrate (0.6 g, 1.27 mmole) is added to 8.5 ml carbon disulfide and 0.2 ml DMF and is stirred for 15 minutes under reflux. To this mixture is added (R)-2-bromo-1-(3,4,5-trimethoxy-phenyl) ethanol (B") (0.1 g, 0.344 mmole). The reaction mixture is refluxed under an $N_2$ atmosphere for 24 hours. The solvent is removed in vacuo, and the remaining oil redissolved in ethyl acetate, washed with 10% NaOH and $H_2O$. The organic layer is dried over $MgSO_4$, filtered, and evaporated to an oil which is purified by flash column chromatography using 1:1 hexane/ ethyl acetate as eluent. (0.034 g, 33%: $[\alpha]^{21}D=+90.5^m$ 1% $CHCl_3$). NMR: ($CDCl_3$) 3.85,s,3H;3.88,s,6H;3.99,dd,1H; 4.17,t,1H;5.57,dd,1H;6.70,s,2H.

Step D: Preparation of (S)-1-(3,4,5-trimethoxyphenyl)-1,2-ethanedithiol (E")

Lithium aluminum hydride (0.146 g, 3.84 mole) is added to 20 ml dry diethyl ether. To this slurry is added (s)-4-(3,4,5-trimethoxyphenyl)-1,3-dithiolane-2-thione (D") (0.725 g, 2.40 mmole) predissolved in 30 ml dry THF. The reaction is stirred at room temperature under an $N_2$ atmosphere for 24 hours. The reaction is cooled to 0° C. and the excess hydride destroyed with $H_2O$. The reaction mixture is acidified with 10% HCl and immediately extracted with diethyl ether. The organic layer is washed with $H_2O$, dried over $MgSO_4$, filtered and evaporated to a whine solid (0.514 g, 82%).

$[\alpha]^{21}D=+42.3^s$ 1% $CHCl_3$. NMR: ($CDCl_3$) 3.84,s, 3H;3.87,s,6H;3.98,dd,1H; 4.13,dd,1H;5.58,dd,1H;6.69,s, 2H.

The Mosher ester derivation of (S)-1-(3,4,5-trimethoxyphenyl)-1,2-ethanedithiol (F") was made as follows. (S)-1-(3,4,5-trimethoxyphenyl)-1,2-ethanedithiol (E") (0.004 g, 0.015 mole), (R) (+)-α-methoxy-α-(trifluoromethyl) phenylacetic acid chloride (0.012 g, 0.04 mmole), dimethylaminopyridine (0.001 g), triethylamine (0.004 g, 0.04 mmole) and 4 ml dry dichloromethane are stirred at room temperature for 5 hours. The solvent is removed in vacuo, and the remaining oil redissolved in 0.5 ml ethyl acetate. This solution is added no a micro flash silica column in a disposable pasteur pipette and the product eluted with 1:1 hex/ethyl acetate (0.008 g, 90%). By $^1$H-NMR, the ratio of RR/RS diastereomers is 11:1 (84% ee). NMR: ($CDCl_3$) (mixture of diastereomers) 3.2–3.4,m, 2H;3.55–3.70,m,2H;3.30,d,3H;3.44,d,3H;3.48,d,3H; 3.51,d, 3H;3.74,s,6H;3.80,s,3H;3.81,s,6H;3.83,s,3H; 4.63,dt, 2H;6.43,s,2H;6.46,s,2H;7.29–7.54,m,10H. M.S.: (IBu) 693 (base), 443,391.

Step E: Preparation of (R,S)-2-(3-hydroxy-5-iodo-4-methoxyphenyl)-4-(3,4,5-trimethoxyphenyl)-1,3-dithiolane (G")

(S)-1-(3,4,5-trimethoxyphenyl)-1,2-ethanedithiol (E") (0.500 g, 1.92 mmole]), 4-hydroxy-5-iodo-3-methoxybenzaldehyde (0.486 g, 1.75 mmole) and 0.176 g of pyridinium paratoluene sulfonate are added to 50 ml dry benzene and refluxed with Dean-Stark removal of the benzene-water azeotrope for 12 hours. The benzene is removed in vacuo, and the remaining oil redissolved in dichloromethane. The organic layer is washed with 10% $NaHCO_3$ and $H_2O$. The organic layer is dried over $MgSO_4$, filtered, and evaporated in vacuo to an oil which is purified by flash column chromatography with 2:1 hex/ethyl acetate as eluent. The product mixture contains a 1.0/1.2 cis/trans ratio (0.800 g, 88%). The trans isomer is isolated after four recrystallizations from methanol (0.100 g).

NMR: ($CDCl_3$) 3.49,dd,1H;3.64,dd,1H;3.84,s,3H; 3.88,s, 6H;3.93,s,3H;5.05,dd,1H;5.76,s,1H;6.11,s,1H; 6.72,s, 2H;7.10,d,1H;7.50,d,1H. M.S.: (IBu) 520 (100%) Melting Point: 145°–146° C. $[\alpha]^{21}D=+19.5^s$ 1% $CHCl_3$.

Figure 5A:
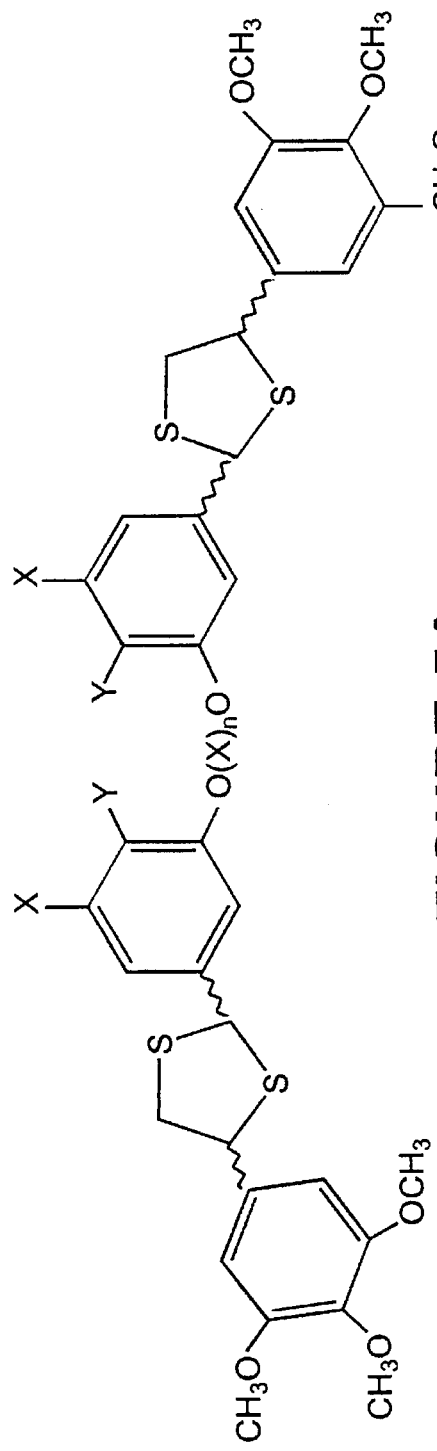
FIGS. 5a and 5b are chemical structures of dimeric 2,4-diaryl-1,3-dithiolane compounds.
Figure 5B:
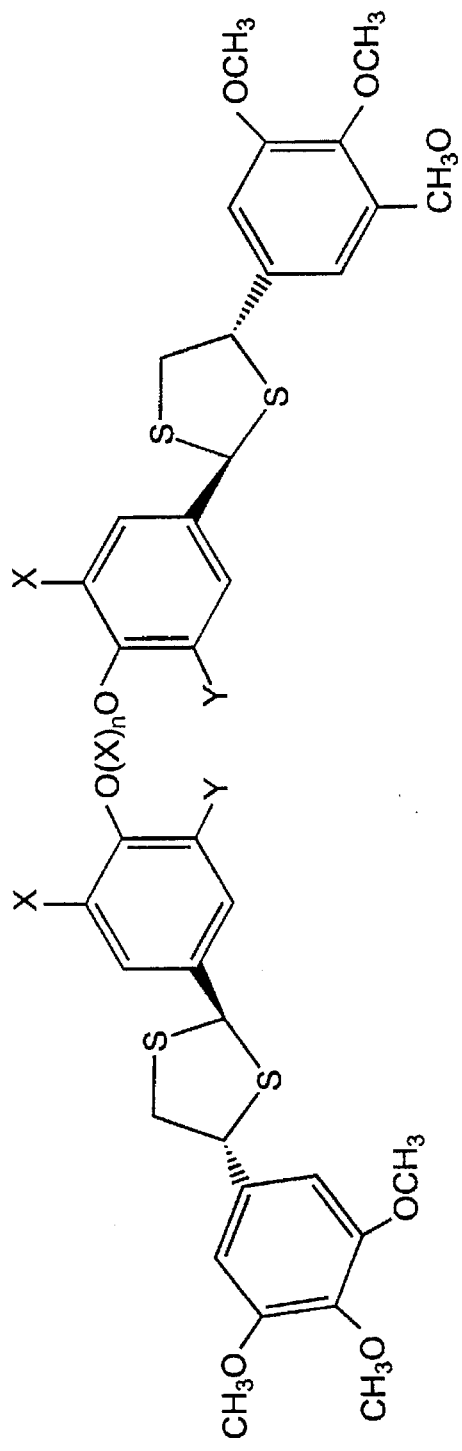

FIGS. 5a and 5b show chemical structures of dimeric 2,4-diaryl-1,3-dithiolane compounds. Erez et al., in J. Med. Chem., 25, 847–849 (1982), reported an increase in the binding activity of bivalent ligands versus their monomer counterparts in some biological systems (specifically, opioid receptors. Several dimeric 2,4-diaryl-1,3-dithiolane compounds have been synthesized and the substituent groups of those dimeric compounds are shown in FIGS. 6a and 6b which, respectively, relate to the dimeric compounds shown in FIGS. 5a and 5b. In addition, the antagonist activity for PAF induced platelet aggregation for one of the dimeric compounds has been tested according to the procedures described above. Note that only a small concentration of the dimeric compound is required to inhibit PAF induced platelet aggregation (FIG. 6b shows compounds 22d has an $IC_{50}$ value of 9 µM). Example 11 describes the synthesis of the dimeric 2,4-diaryl-1,3-dithiolane compounds.

EXAMPLE 11

Figure 20:
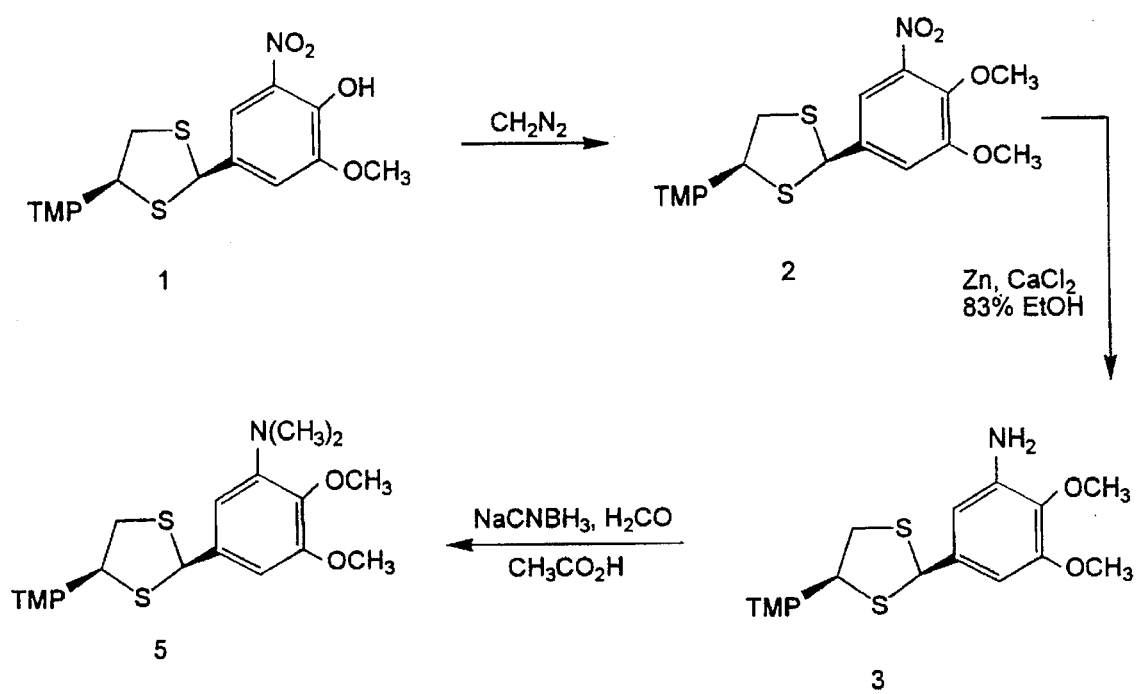
FIG. 20 is a schematic drawing showing the synthetic approach for producing 2,4-diaryl-1,3-dithiolane compounds with an aryl amino functionality.

Cis and trans-2-(3-nitro-4-hydroxy-5-methoxyphenyl)-4-(3,4,5-trimethoxyphenyl)-1,3-dithiolane (1) (FIG. 20)

Figure 19:
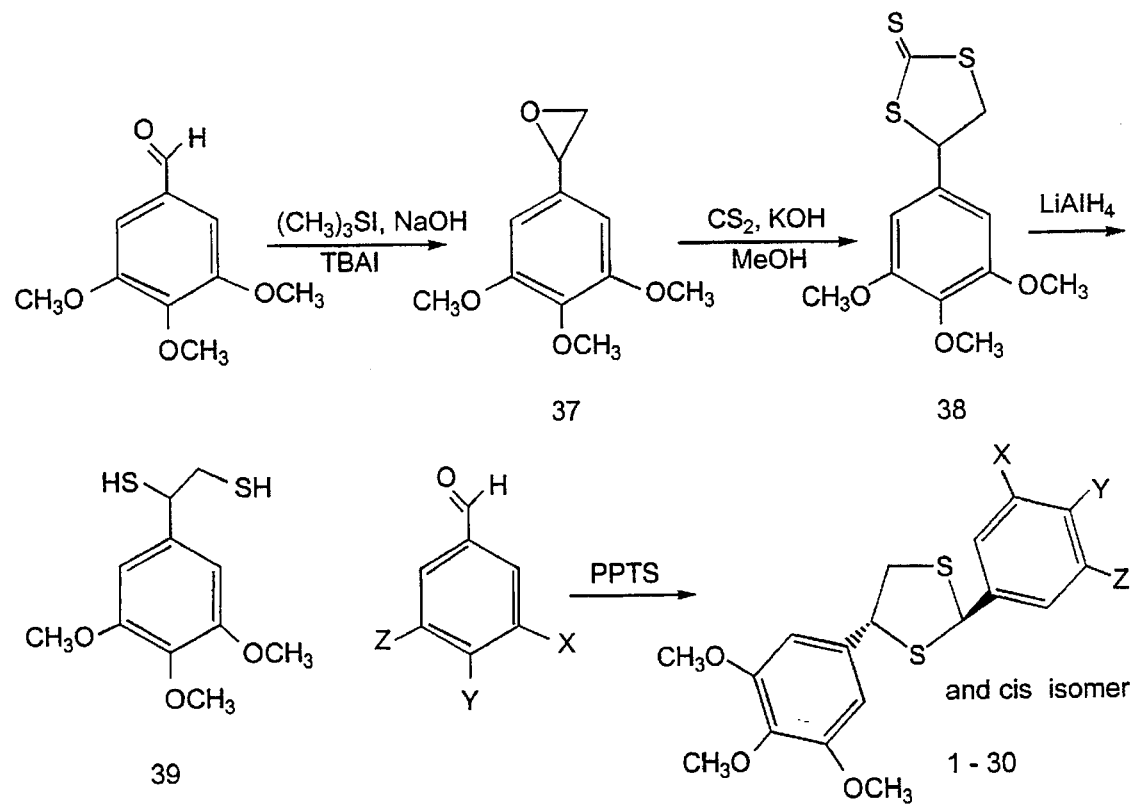
FIG. 19 is a schematic drawing showing the general synthetic approach for producing 2,4-diaryl-1,3-dithiolane compounds.

Step A Preparation of 1-(3,4,5-trimethoxyphenyl)oxirane (37) (FIG. 19)

3,4,5-trimethoxybenzaldehyde (9.80 g,50.0 mmole) was dissolved in 20 ml $CH_2Cl_2$ along with tetrabutylammonium iodide (0.396 g,1.00 mmole). To this solution was added a cooled 50% NaOH solution (10 g NaOH in 10 ml $H_2O$). To this mixture was added trimethylsulfonium iodide (10.20 g,50.0 mmole). The reaction was refluxed with vigorous stirring for 15 hours. The reaction was quenched with $H_2O$, extracted with $CH_2Cl_2$, washed with brine, dried over $MgSO_4$ and evaporated to an oil (9.69 g, 84%) which solidified to a white solid after 24 hours in vacuo.

NMR ($CDCl_3$) 2.75,dd,1H: 3.11,dd,1H: 3.81,d,1H: 3.82, s,3H; 3.85,s,6H; 6.50,s,2H M.S. (CI) 211 (100%). Melting Point 54.5°–56° C. Anal. Calcd. for $C_{11}H_{14}O_4$: C, 62.85: H, 6.76. Found C, 62.63; H, 6.76.

Step B Preparation of 4-(3,4,5-trimethoxyphenyl)-1,3-dithiolane-2-thione (38)(FIG. 19)

Powdered potassium hydroxide (2.40 g,42.85 mmole) was dissolved in 10.0 ml methanol and carbon disulfide (3.10 ml, 51.43 mmole) was added at 0° C. under an $N_2$ atmosphere. The reaction mixture was shaken vigorously and 1-(3,4,5-trimethoxyphenyl) oxirane (37) (FIG. 19) (3.50 g,16.66 mmole) was added. The reaction was allowed to warm to room temperature at which point the reaction started to reflux for twenty minutes. Subsequently, the reaction was stirred at room temperature overnight. The yellow precipitate was isolated by suction filtration and was washed with $H_2O$ and diethylether to yield 3.82 g (76%).

NMR: ($CDCl_3$) 3.85,s,3H; 3.88,s,6H; 3.99,dd,1H; 4.17,t, 1H; 5.57,dd,1H; 6.70,s,2H. M.S.: (IBu) 303 (100%). Melting Point: 152°–154° C. Anal. Calcd. for $C_{12}H_{14}O_3S_3$: C, 47.66; H, 4.67: S, 31.80. Found: C, 47.90; H, 4.70; S, 31.71.

Step C Preparation of 1-(3,4,5-trimethoxyphenyl)-1,2-ethanedithiol (39) (FIG. 19)

Lithium aluminum hydride (0.20 g,5.27 mmole) was added to 15 ml dry diethyl ether. To this slurry was added 4-(3,4,5-trimethoxyphenyl)-1,3-dithiolane-2-thione (38) (FIG. 19) (1.0 g,3.31 mmole) predissolved in 20 ml dry THF. The reaction was refluxed under an $N_2$ atmosphere for 12 hours. The reaction was cooled to 0° C. and the excess hydride destroyed with $H_2O$. The reaction mixture was acidified with 10% HCl and immediately extracted with diethyl ether. The organic layer was washed with $H_2O$, dried over $MgSO_4$, and concentrated to a white solid (0.836 g, 97%).

NMR: ($CDCl_3$) 2.34,d,1H; 2.95,m, 1H; 3.09,m, 1H; 3.84, s,3H; 3.87,s,6H; 4.03,m,1H: 6.53,s,2H. M.S. (IBu): 261

(100%). Melting Point: 72.5°–73.5° C. Anal. Calcd. for $C_{11}H_{16}O_3S_2$: C, 50.74: H, 6.19: S, 24.63. Found: C, 50.85; H, 6.20; S, 24.53.

Step D Preparation of cis and trans 2-(4-hydroxy-3-methoxy-5-nitrophenyl)-4-(3,4,5-trimethoxyphenyl)-1,3-dithiolane (1) (FIG. 20)

1-(3,4,5-trimethoxyphenyl)-1,2-ethanedithiol (39) (FIG. 19) (25.4 g,97.7 mmole), 5-nitrovanillin (16.73 g, 84.9 mmole), pyridinium para-toluenesulfonate (PPTS) (8.52 g, 33.9 mmole) and 100 ml dry benzene were refluxed under an argon atmosphere with Dean-Stark removal of the benzene-water azeotrope for 12 hours. The reaction was cooled to room temperature and the precipitated PPTS removed by vacuum filtration. Hexane (100 ml) was added to the filtrate and the precipitate collected by vacuum filtration. The yellow solid was washed with cold water, followed by minimal cold methanol and finally cold diethyl ether to leave 28.62 g of a 1:1.3 cis/trans ratio of product. Six recrystallizations from ethyl acetate/hexane gives 4.3 g of pure trans diastereomer. An additional 2.4 g trans product can be obtained by repeating the above crystallization process from the material remaining in the mother liquors. Once 6.7 g of trans product was isolated,0.315 g of cis diastereomer was isolated by recrystallizing the combined mother liquors from above.

Trans epimer:

NMR (CDCl$_3$) 3.50,dd,1H; 3.66,dd,1H; 3.84,s,3H; 3.88, s,6H; 4.00,s,3H: 5.05,dd,1H; 5.80,s,1H; 6.72.s.2H; 7.41,d, 1H; 7.90,d,1H. M.S. (IBu) 440 (100%). Melting Point 149°–151° C. Anal. Calcd. for $C_{19}H_{21}O_7S_2N$: C, 51.92: H, 4.82: S. 14.59. Found: C, 52.03: H, .4.86: S, 14.51.

Cis epimer:

NMR: (CDCl$_3$) 3.53,d, 2H; 3.84,s,3H; 3.89,s,6H; 3.97,s, 3H; 4.88,t,1H; 5.70,s,1H; 6.75,s,2H; 7.37,d,1H; 7.97,d, 1H. M.S. (CI) 440 (100%). Melting Point 120°–121° C. Anal. Calcd. for $C_{19}H_{21}O_7S_2N$: C, 51.92: H, 4.82: S, 14.59. Found: C, 52.05; H, 4.87; S, 3.12

EXAMPLE 12

Preparation of Cis and trans-2-(3,4-dimethoxy-5-nitrophenyl)-4-(3,4,5-trimethoxyphenyl)-1,3-dithiolane (2) (FIG. 20)

Using the Aldrich diazald kit, diazald (13.0 g, 60.7 mmole) predissolved in 100 ml diethyl ether was added dropwise to an aqueous potassium hydroxide solution (ethanol, 27 ml; H$_2$O, 21 ml; and potassium hydroxide, 13.3 g) at 65° C. The diazomethane/ether distillate was added at 0° C. to a solution of trans-2-(4-hydroxy-3-methoxy-5-nitrophenyl)-4-(3,4,5-trimethoxyphenyl)-1,3-dithiolane (1) (FIG. 20) predissolved in 25 ml chloroform and 50 ml methanol. The reaction was stirred to completely homogenize the solution and was then allowed to stand at room temperature under an argon atmosphere for 5 hours. The solvent was removed in vacuo and the remaining oil was dissolved in 10 ml diethyl ether. The product crystallized out of the ether solution to yield 3.285 g (98%) of light yellow crystals.

Trans epimer

NMR: (CDCl$_3$) 3.49,dd,1H: 3.65,dd,1H; 3.84,s,3H; 3.88, s,6H; 3.96,s,3H; 3.97,s,3H; 5.04,dd,1H; 5.78,s,1H; 6.71,s, 2H; 7.32,d,1H; 7.58,d,1H. M.S. (CI) 454 (100%). Melting Point 133°–134° C. Anal. Calcd. for $C_{20}H_{23}O_7S_2N$: C, 52.97; H, 5.11; S, 14.14; N, 3.09. Found: C, 52.92: H, 5.06; S, 14.06; N, 3.14.

The cis product can be obtained in the same manner as above starting from cis-2-(4-hydroxy-3-methoxy-5-nitrophenyl)-4-(3,4,5-trimethhoxyphenyl)-1,3-dithiolane (1) (FIG. 20).

Cis epimer:

NMR: (CDCl$_3$) 3.55,d,2H: 3.84,s,3H; 3.88,s,6H: 3.93,s, 3H; 3.97,s,3H; 4.88,t,1H: 5.70,s,1H; 6.73,s,2H; 7.30,d,1H; 7.65,d,1H. M.S. (CI) 454 (100%). Melting Point 99°–100° C. Anal. Calcd. for $C_{20}H_{23}O_7S_2N$: C, 52.97; H, 5.11; S, 14.14; N, 3.09. Found: C, 53.08; H, 5.09; S, 14.04; N, 3.10.

EXAMPLE 13

Preparation of Cis and trans-2-(5-amino-3,4-dimethoxyphenyl)-4-(3,4,5-trimethoxy-phenyl)-1,3-dithiolane (3) (FIG. 20)

Trans-2-(3,4-dimethoxy-5-nitrophenyl)-4-(3,4,5-trimethoxyphenyl)-1,3-dithiolane (2) (FIG. 20) (3.10 g, 6.84 mmole) was predissolved in 33 ml absolute ethanol. To this solution was added calcium chloride (0.721 g, 6.50 mmole) predissolved in 7 ml H$_2$O followed by freshly activated zinc dust (10.0 g,195 mmole). The reaction was refluxed for 12 hours. The solid was removed by vacuum filtration through celite and was washed with ethyl acetate. The filtrate was washed with H$_2$O, dried over MgSO$_4$, and evaporated in vacuo to a white foam (2.52 g, 87%).

Trans epimer:

NMR: (CDCl$_3$) 3.45,dd,1H; 3.63,dd,1H; 3.81,s,3H; 3.84, s,3H; 3.87,s,3H; 3.88,s,6H; 5.04,dd,1H; 5.75,s,1H; 6.56,d, 1H; 6.65,d,1H; 6.72,s,2H. M.S. (IBu): 424, 227, 195 (100%). Melting Point 48°–51° C. (foam). Anal. Calcd. for $C_{20}H_{25}O_5S_2N$: C, 56.72: H, 5.95: S, 15.14: N, 3.31. Found C, 56.79: H, 5.96; S, 15.04: N, 3.35.

The cis product can be obtained in the same manner as above starting from cis-2-(3,4-dimethoxy-5-nitrophenyl)-4-(3,4,5-trimethoxyphenyl)-1,3-dithiolane (2) (FIG. 20).

Cis epimer:

NMR: (CDCl$_3$) 3.53,d,2H; 3.81,s,3H; 3.83,s,3H; 3.85,s, 3H; 3.87,s,6H; 4.81,t,1H; 5.68,s,1H; 6.64,d,1H; 6.68,d, 1H; 6.74,s,2H. M.S. (CI) 424 (100%), 227, 195, 119.

EXAMPLE 14

Preparation of cis and trans-2-(3,4-dimethoxy-5-N-methylaminophenyl)-4-(3,4,5-trimethoxyphenyl)-1,3-dithiolane (4) (table 1)

Trans-2-(5-amino-3,4-dimethoxyphenyl)-4-(3,4,5-trimethoxyphenyl)-1,3-dithiolane (3) (FIG. 20) (2.07 g,4.89 mmole), glacial acetic acid (57 µL, 1.0 mmole), 37% formaldehyde (75 µL, 1.0 mmole), and dry acetonitrile (30 ml) were stirred at room temperature under an argon atmosphere for 5 minutes. To this solution was added sodium cyanoborohydride (0.069 g,1.1 mmole) and the reaction was stirred at room temperature for 48 hours. The precipitate was removed by filtration and the filtrate quenched with 10% potassium carbonate and extracted with dichloromethane. The organic layer was washed with brine, dried over MgSO$_4$, and concentrated in vacuo to an oil which was purified by flash column chromatography with 2:1 hex/ethyl acetate as eluent (0.400 g, 91%). The excess primary amine was recovered in yield.

Trans epimer:

NMR: (CDCl$_3$) 2.87,s,3H; 3.46,dd,1H; 3.65,dd,1H; 3.78, s,3H; 3.84,s,3H; 3.87,s,3H; 3.88,s,6H; 5.07,dd,1H; 5.83,s, 1H; 6.51,d,1H; 6.59,d,1H; 6.73,s,2H;. M.S. (CI): 438 (100%).

The cis product can be obtained in the same manner as above starting from cis-2-(5-amino-3,4-dimethoxyphenyl)-4-(3,4,5-trimethoxyphenyl)-1,3-dithiolane (3) (FIG. 20).

EXAMPLE 15

Preparation of cis and trans-2-(3,4-dimethoxy-5-N, N-dimethylaminophenyl)-4-(3,4,5-trimethoxyphenyl)-1,3-dithiolane (5) (FIG. 20)

Trans-2-(5-amino-3,4-dimethoxyphenyl)-4-(3,4,5-trimethoxyphenyl)-1,3-dithiolane (3) (FIG. 20) (0.031 g,0.073 mmole), 37% formaldehyde (60 uL), and sodium cyanoborohydride (0.014 g,0.220 mmole) were dissolved in dry acetonitrile (2 ml). To this solution at room temperature under an argon atmosphere was added glacial acetic acid (83 µL). The reaction was stirred at room temperature for 24 hours. The precipitate was removed by filtration and the filtrate quenched with 10% potassium carbonate and extracted with dichloromethane. The organic layer was washed with brine, dried over $MgSO_4$, and concentrated in vacuo to an oil which was purified by flash column chromatography with 2:1 hex/ethyl acetate as eluent (0.017 g, 52%). The compound can be recrystallized from hexane/ethyl acetate to a white solid.

Trans epimer:

NMR: ($CDCl_3$) 2.84,s,6H; 3.46,dd,1H; 3.55,dd,1H; 3.80, s,3H; 3.84,s,3H; 3.88,s,9H; 5.07,dd,1H; 5.83,s,1H; 6.73,s, 3H; 6.83,d,1H. M.S. (CI) 452, 226, 195, 83 (100%). Melting Point 89°–91° C. Anal. Calcd. for $C_{22}H_{29}O_5S_2N$: C, 58.51; H, 6.47; S, 14.20; N, 3.10. Found: C, 58.60; H, 6.47; S, 14.13; N, 3.13.

The cis product can be obtained in the same manner as above starting from cis-2-(5-amino-3,4-dimethoxyphenyl)-4-(3,4,5-trimethoxyphenyl)-1,3-dithiolane (3) (FIG. 20).

Cis epimer: NMR: ($CDCl_3$) 2.83,s,6H; 3.55,d,2H; 3.79, s,3H; 3.83,s,3H; 3.87,s,9H; 4.83,t,1H; 5.73,s,1H; 6.76,bs, 3H; 6.85,d, 1H. M.S. (CI): 452, 226, 117 (100%).

EXAMPLE 16

Figure 21:
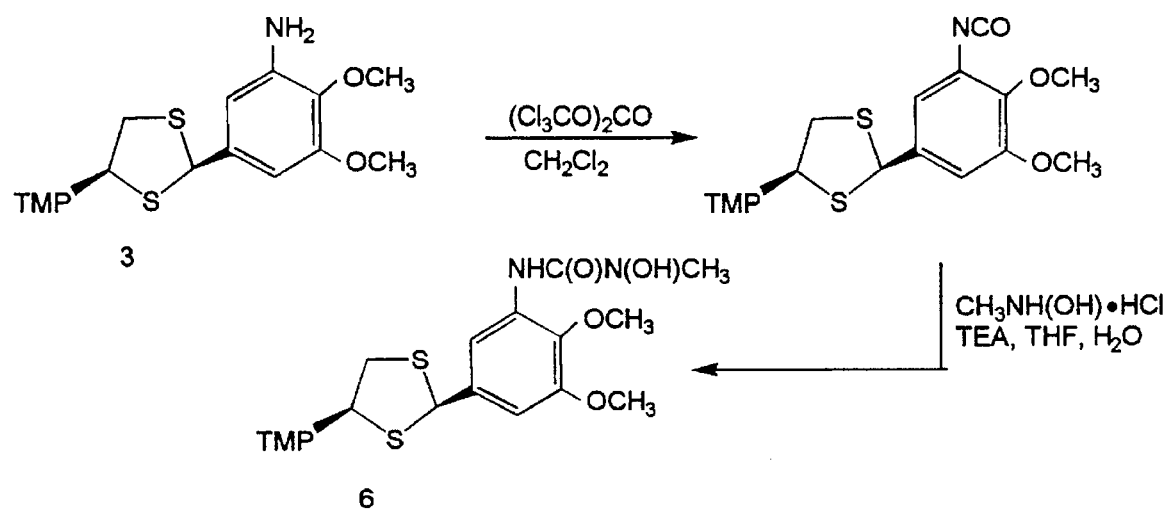
FIG. 21 is a schematic drawing showing the synthetic approach for producing 2,4-diaryl-1,3-dithiolane compounds with an aryl hydroxyurea functionality.

Preparation of cis and trans-N'-hydroxyl-N'-methyl-N-[2,3-dimethoxy-5-{3-(3,4,5-trimethoxyphenyl)-2,4-dithiolanyl}]phenyl urea (6) (FIG. 21)

Trans-2-(5-amino-3,4-dimethoxyphenyl)-4-(3,4,5-trimethoxyphenyl)-1,3-dithiolane (3) (FIG. 20) (0.150 g,0.355 mmole), triethylamine (50 µL), triphosgene (0.035 g,0.118 mmole), and 20 ml dry dichloromethane were refluxed for 2 hours under an argon atmosphere. When all of the amine had been converted to isocyanate by TLC, the reaction was cooled to room temperature and N-methyl hydroxylamine hydrochloride (0.044 g,0.533 mmole) predissolved in 5 ml THF, 75 µL triethylamine, and 0.5 ml $H_2O$ was added. The reaction was stirred at room temperature overnight under an argon atmosphere. The solvent was removed in vacuo, the remaining oil redissolved in dichloromethane. The organic layer was washed with $H_2O$, dried over $MgSO_4$, and concentrated to an oil in vacuo which was purified by flash column chromatography with 2:1 hexane/ethyl acetate as eluent. (112 mg, 64% yield foam). The product can be crystallized from hexane/ethyl acetate to a white solid.

Trans epimer:

NMR: ($CDCl_3$) 3.28,s,3H; 3.45,dd,1H; 3.65.dd,1H; 3.84, s,3H; 3.85,s,3H; 3.88,s,6H; 3.90,s,3H; 5.09,dd,1H; 5.72,s, 1H; 6.72,s,2H; 6.90,d,1H; 8.15,d,1H; 8.52,s,1H. M.S. (CI): Melting Point 93°–94° C. Anal. Calcd. for $C_{22}H_{28}O_7S_2N_2$: C, 53.21; H, 5.68; S, 12.91; N, 5.66. Found: C, 53.31; H, 5.70; S, 12.84; N, 5.60.

The cis product can be obtained in the same manner as above starting from cis-2-(5-amino-3,4-dimethoxyphenyl)-4-(3,4,5-trimethoxyphenyl)-1,3-dithiolane (3) (FIG. 20).

Cis epimer:

NMR: ($CDCl_3$) 3.25,s,3H; 3.55,d,2H; 3.83.s,3H; 3.84,s, 3H; 3.88,s,9H; 4.84,dd,1H; 5.71,s,1H; 6.78,s,2H; 6.89,d, 1H; 8.23,d, 1H; 8.52,s,1H. M.S. (CI): 497, 450,424, 227, 147.

EXAMPLE 17

Preparation of cis and trans-2-(5-acetamido-3,4-dimethoxyphenyl)-4-(3,4,5-trimethoxyphenyl)-1,3-dithiolane (7) (table 1)

Trans-2-(5-amino-3,4-dimethoxyphenyl)-4-(3,4,5-trimethoxyphenyl)-1,3-dithiolane (3) (FIG. 20) (25 mg) was dissolved in 5 ul dry dichloromethane and cooled to 0° C. under an argon atmosphere. To this solution was added acetic anhydride (11 µL) followed by 1 drop glacial acetic acid. The reaction was allowed to warm to room temperature overnight. The reaction was quenched with 10% $NaHCO_3$ and extracted with dichloromethane. The organic layer was dried over $MgSO_4$, and concentrated to an oil which was purified by flash column chromatography using 2:1 hexane/ethyl acetate as eluent (24 mg, 89% yield).

Trans epimer:

NMR: ($CDCl_3$) 2.21,s,3H; 3.46,dd,1H; 3.67,dd,1H; 3.84, s,3H; 3.87,s,3H; 3.88,s,6H; 3.91,s,3H; 5.08,dd,1H; 5.82,s, 1H; 6.72,s,2H; 6.97,d, 1H; 7.78,bs,1H; 8.8.24,d, 1H. M.S. (CI): 466, 117 (100%).

The cis product can be obtained in the same manner as above starting from cis-2-(5-amino-3,4-dimethoxyphenyl)-4-(3,4,5-trimethoxyphenyl)-1,3-dithiolane (3) (FIG. 20).

EXAMPLE 18

Cis/trans-2-(3-methoxy-4-propoxy-5-nitrophenyl)-4-(3,4,5-trimethoxyphenyl)-1,3-dithiolane (8) (table 1)

Step A Preparation of 3-methoxy-5-nitro-4-propoxybenzaldehyde (40)

5-nitrovanillin (2.50 g,12.69 mmole) and freshly pulverized potassium carbonate (5.25 g,38.07 mmole) were added to 40 ml dry DMF and stirred at room temperature for 5 minutes. Propyl iodide (4.31 g,25.38 mmole) was added to the reaction mixture which was stirred under an $N_2$ atmosphere at 60° C. for 36 hours. The reaction mixture was quenched with 125 ml $H_2O$ and extracted with dichloromethane. The organic layer was washed with ss NaCl, dried over $MgSO_4$ and the solvent removed in vacuo to leave a yellow oil. (1.71 g, 56%).

NMR: ($CDCl_3$) 1.03,t,3H; 1.81,m,2H; 3.97,s,3H; 4.21,t, 2H; 7.59,d, 1H; 7.80,d, 1H; 9.90,s,1H. M.S.: (IBu) 240 (100%).

Step B Preparation of cis/trans-2-(3-methoxy-4-propoxy-5-nitrophenyl)-4-(3,4,5-trimethoxyphenyl)-1,3-dithiolane (8) (table 1)

1-(3,4,5-trimethoxyphenyl)-1,2-ethanedithiol (39) (FIG. 19) (0.689 g,2.65 mmole), 3-methoxy-5-nitro-4-propoxybenzaldehyde (40) (0.633 g, 2.65 mmole) and 0.266 g of pyridinium para-toluenesulfonate was added to 50 ml dry benzene and refluxed with Dean-Stark removal of the benzene- water azeotrope for 24 hours. The benzene was removed in vacuo, and the remaining oil redissolved in dichloromethane and was purified by flash column chromatography with 9:1 hex/ethyl acetate as eluent. The product mixture contains a 1/1 cis/trans ratio (0.600 g, 47%).

cis/trans epimers:

NMR: ($CDCl_3$) 0.98,t,6H; 1.76,m,4H; 3.46,dd,1H; 3.52, d,2H; 3.62,dd,1H; 3.81,s,6H; 3.84,s,12H; 3.98,s,3H; 3.91,s,

3H; 4.05,t,4H; 4.86,t,1H; 5.03,dd,1H; 5.67,1H; 5.76,s,1H; 6.70,s,2H; 6.72,s,2H; 7.28,t,2H; 7.53,d,1H; 7.60,d,1H. M.S. (CI): 482, 288, 268, 240 (100%), 227, 198.

EXAMPLE 19

Preparation of cis/trans-2-(5-amino-3-methoxy-4-propoxyphenyl)-4-(3,4,5-trimethoxyphenyl)-1,3-dithiolane (9) (Table 1)

1:1 Cis/trans-2-(3,4-dimethoxy-5-nitrophenyl)-4-(3,4,5-trimethoxyphenyl)-1,3-dithiolane (8) (Table 1) (0.40 g,0.832 mmole), calcium chloride (0.088 g,0.790 mmole), freshly activated zinc dust (1.70 g,33.26 mmole) and 30 ml 83% ethanol were refluxed for 4 hours. The solid was removed by vacuum filtration and the filtrate concentrated to an oil in vacuo. The oil was redissolved in dichloromethane, dried over $MgSO_4$, and purified by flash column chromatography using 2:1 hex/ethyl acetate as eluent. The product mixture (foam) contains a 1.0/1.0 cis/trans ratio (0.302 g, 81%).

cis/trans epimers

NMR: ($CDCl_3$) 1.02,t,6H; 1.77,m,4H; 3.45,dd,1H; 3.53, d,2H; 3.62,dd,1H; 3.83–3.87, 4s, 24H; 3.91,t,4H; 4.81,t,1H; 5.02,dd,1H; 5.68,s,1H; 5.75,s,1H; 6.55,d,1H; 6.58,d, 1H; 6.64,d, 1H; 6.68,d, 1H; 6.71,s,2H; 6.75,s,2H. M.S. (CI): 452, 195 (100%).

EXAMPLE 20

Preparation of cis/trans-2-(5-dimethylamino-3-methoxy-4-propoxyphenyl)-4-(3,4,5-trimethoxyphenyl)-1,3-dithiolane (10) (Table 1)

1:1 cis/trans-2-(5-amino-3,4-dimethoxyphenyl)-4-(3,4,5-trimethoxyphenyl)-1,3-dithiolane (9) (Table 1) (0.100 g,0.222 mmole), 37% formaldehyde (177 uL), and sodium cyanoborohydride (0.044 g,0.700 mmole) were dissolved in dry acetonitrile (4 ml). To this solution at room temperature under an argon atmosphere was added glacial acetic acid (250 µL). The reaction was stirred at room temperature for 24 hours. The precipitate was removed by filtration and the filtrate quenched with 10% potassium carbonate and extracted with dichloromethane. The organic layer was washed with brine, dried over $MgSO_4$, and concentrated in vacuo to an oil which was purified by flash column chromatography with 2:1 hex/ethyl acetate as eluent. The product mixture (oil) contains a 1.0/1.0 cis/trans ratio (0.050 g, 47%).

cis/trans epimers:

NMR: ($CDCl_3$) 1.01,t,3H; 1.76,m,4H; 2.82,s,3H; 2.83,s, 3H; 3.46,dd,1H; 3.62,d,2H; 3.66,dd,1H; 3.84–3.88, 4s, 24H; 4.83,t,1H; 5.07,dd,1H; 5.75,s,1H; 5.83,s,1H; 6.73,s,3H; 6.76,s,3H; 6.82,dd,1H; 6.84,dd,1H. M.S. (CI): 480, 195 (100%).

EXAMPLE 21

Cis/trans-2,3-dimethoxy-5-[3-(3,4,5-trimethoxyphenyl)-2,4-dithiolanyl]phenyl carboxylic acid (11) (Table 1)

Figure 22:
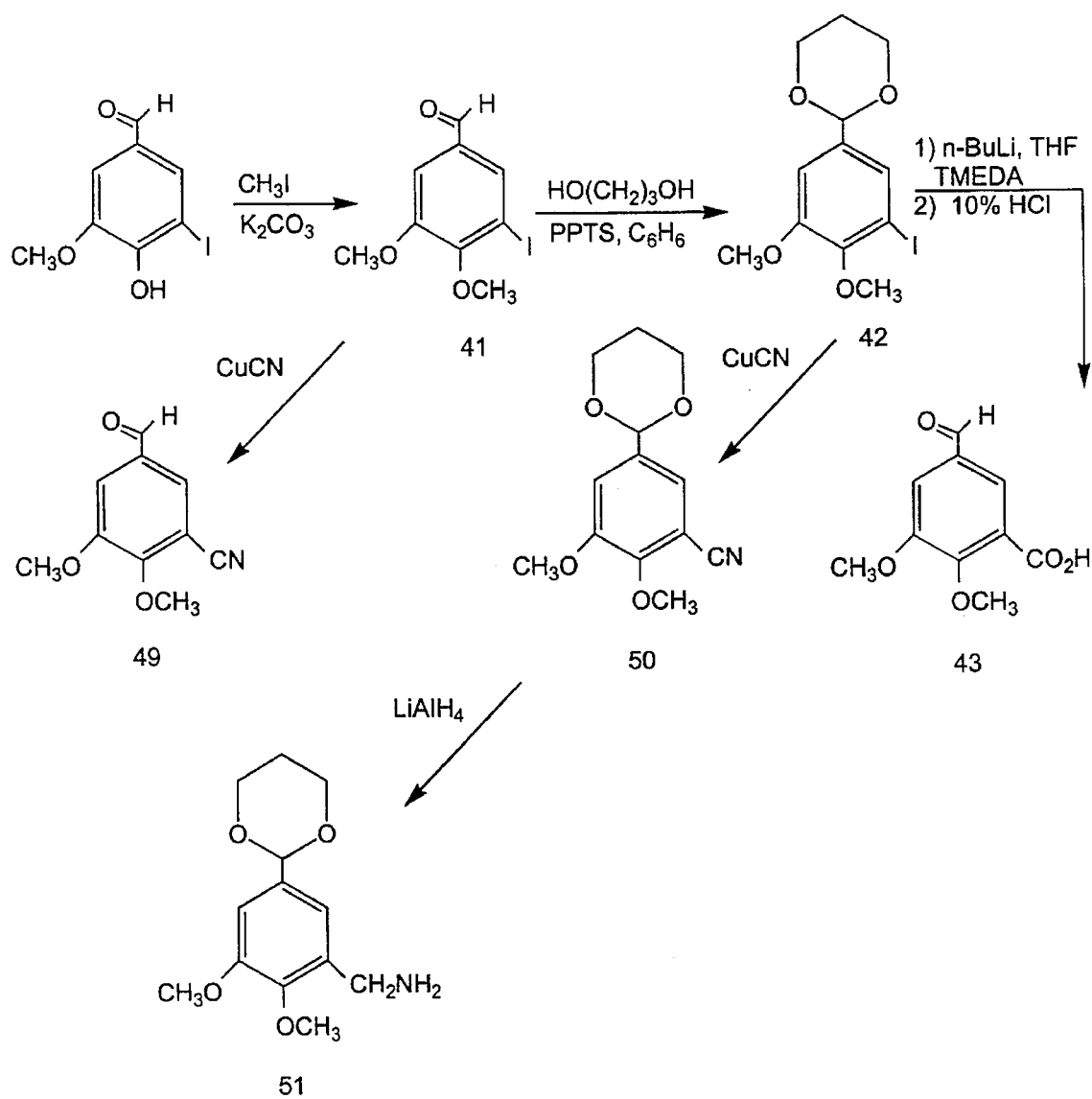
FIG. 22 is a schematic drawing showing the synthetic approach for producing 2,4-diaryl-1,3-dithiolane intermediates with a substituted aryl niffue, carboxylic acid or methylamino functionalities.

Step A Preparation of 3,4-dimethoxy-5-iodobenzaldehyde (41) (FIG. 22)

5-iodovanillin (6.0 g, 21.58 mmole), potassium carbonate (5.96 g, 43.16 mmole), iodomethane (9.06 g, 64.77 mmole) and dry DMF (50 ml) were stirred at room temperature under an argon atmosphere overnight. The reaction was quenched with 250 ml $H_2O$ and extracted with diethyl ether. The organic layer was dried over $MgSO_4$, and concentrated to an oil in vacuo which was purified by flash column chromatography using 3:1 hexane/ethyl acetate as eluent. The column gives 5.814 g (92%) of a white solid.

NMR: ($CDCl_3$) 3.92,s,6H; 7.40,s,1H; 7.84,s,1H; 9.82,s, 1H.

Step B Preparation of 2-(3,4-dimethoxy-5-iodophenyl)-1,3-dioxane (42) (FIG. 22)

3,4-dimethoxy-5-iodobenzaldehyde (41) (FIG. 22) (5.814 g,19.9 mmole), 1,3-propanediol (6.13 g, 79.6 mmole), pyridinium para-toluenesulfonate (2.0 g, 7.96 mmole) and 100 ml dry benzene were refluxed with Dean-Stark removal of the benzene-water azeotrope overnight. The benzene was removed in vacuo and the remaining oil redissolved in diethyl ether and was washed with 10% $NaHCO_3$ and $H_2O$. The organic layer was washed over $MgSO_4$, and concentrated to a white solid in vacuo. (6.823 g, 98%). The solid can be recrystallized from hexane/ethyl acetate.

NMR ($CDCl_3$) 1.45,d,1H; 2.20,m,1H; 3.80,s,3H; 3.87,s, 3H; 3.96,dt,2H; 4.25,dd,2H; 5.40,s,1H; 7.04,d,1H; 7.46,d, 1H. M.S. (CI) 351 (100%) Melting Point 76°–77.5° C. Anal. Calcd. for $C_{12}H_{15}O_4I$ C, 41.16; H,4.32: I, 36.24. Found C, 41.30; H, 4.33; I, 36.15.

Step C Preparation of 2,3-dimethoxy-5-formylbenzoic acid (43) (FIG. 22)

2-(3,4-dimethoxy-5-iodophenyl)-1,3-dioxane (42) (FIG. 22) (1.7 g, 4.86 mmole) was dissolved in 40 ml dry THF and cooled to −78° C. under an argon atmosphere. n-butyllithium (4.3 ml of a 1.25M soln.) was added and the reaction was warmed to 0° C. and was stirred at that temperature for an additional 45 minutes. The aryl lithium solution was then poured onto solid carbon dioxide covered with anhydrous diethyl ether. A white precipitate formed immediately. Water was added and the organic solvent subsequently removed in vacuo. The remaining aqueous solution was extracted with ethyl acetate. The organic layer was washed with 5% sodium thiosulfate, water, and then stirred vigorously over an equivolume of 10% HCl overnight. The organic layer was separated and the product extracted into 10% $K_2CO_3$. The basic solution was acidified with 10% HCl and the product extracted into chloroform. The organic layer was dried over $MgSO_4$, and concentrated in vacuo to a white solid (0.412 g, 40%). The solid can be recrystallized from hexane/ethyl acetate.

NMR: ($CDCl_3$) 3.99,s,3H; 4.19,s,3H; 7.67,s,1H; 8.23,s, 1H; 9.95,s,1H. M.S. (CI): 211 (100%) Melting Point 154°–155° C. Anal. Calcd. for $C_{10}H_{10}O_5$: C, 57.14: H,4.80. Found: C, 57.06; H, 4.84.

Step D Preparation of cis/trans-2,3-dimethoxy-5-[3-(3,4,5-trimethoxyphenyl)-2,4-dithiolanyl]phenyl carboxylic acid (11) (Table 1)

2,3-dimethoxy-5-formylbenzoic acid (43) (FIG. 22) (1.775 g,8.45 mmole), 1-(3,4,5-trimethoxyphenyl)-1,2-ethanedithiol (2.51 g, 9.65 mmole) (39) (FIG. 19), pyridinium para-toluenesulfonate (0.848 g, 3.38 mmole) and 100 ml dry benzene were refluxed under an argon atmosphere with Dean-Stark removal of the benzene-water azeotrope for 7 hours. The benzene was removed in vacuo and the remaining oil purified by flash column chromatography using 2:1 ethyl acetate/hexane as eluant. The column yields 2.90 g (76%, 1:1 cis/trans) of a colorless oil which titurates to a white solid in cold methanol. The solid can be recrystallized from hexane/ethyl acetate.

cis/trans epimers:

NMR: ($CDCl_3$) 3.50,dd,1H; 3.57,d,2H; 3.66,dd,1H; 3.84, s,6H; 3.88,s,12H; 3.93,s,3H; 3.97,s,3H; 4.08,s,6H; 4.87,dd, 1H; 5.08,dd, 1H; 5.73,s,1H; 5.82,s,1H; 6.72,s,2H; 6.76,s,

2H; 7.39,d, 1H; 7.42,d, 1H; 7.90,d, 1H; 8.0,d,1H; 11.3,bs, 1H. M.S. (CI): 453 (100%) Melting Point 130°–132° C. Anal. Calcd. for $C_{21}H_{24}O_7S_2$: C, 55.74; H,5.34; S, 14.17. Found: C, 55.73; H, 5.38; S, 14.10.

EXAMPLE 22

Preparation of cis/trans-N-hydroxyl-N-methyl-[2,3-dimethoxy-5-{3-(3,4,5-trimethoxyphenyl)-2,4-dithiolanyl}]phenyl amide (12) (Table 1)

1:1 cis/trans-2,3-dimethoxy-5-[3-(3,4,5-trimethoxyphenyl)-2,4-dithiolanyl]phenyl carboxylic acid (11) (Table 1) (0.650 g, 1.44 mmole), dry DMF (111 µL) and 20 ml dry dichloromethane was cooled to 0° C. under an argon atmosphere. Oxalyl chloride (314 µL, 3.6 mmole) was added and the reaction stirred for 2 hours at 0° C. The acid chloride solution was then added to a solution of N-methylhydroxylamine hydrochloride (0.481 g, 5.76 mmole) predissolved in THF (17 ml), triethylamine (1.2 ml) and water (1.7 ml). The reaction was stirred at room temperature for 48 hours. The reaction was quenched with 10% HCl and extracted with dichloromethane. The organic layer was dried over $MgSO_4$, and concentrated in vacuo to an oil which was purified by flash column chromatography using 2:1 ethyl acetate/hexane as eluent. The column yields 281 mg (41%) as a white foam (1:1 cis/trans).

cis/trans epimers

NMR: ($CDCl_3$) 3.24,s,6H; 3.50,dd,1H; 3.57,d,2H; 3.65, dd,1H; 3.80–3.93,5s,30H; 4.85,dd,1H; 5.05,dd,1H; 5.73,s, 1H; 5.80,s,1H; 6.71,s,2H; 6.74,s,2H; 7.15,d,1H; 7.21,d, 1H; 7.25,d, 1H; 7.28,d, 1H; 8.56,bs,1H. M.S. (CI): 482, 391 (100%)

EXAMPLE 23

Cis/trans-2,6-dimethoxy-4-[3-(3,4,5-trimethoxyphenyl)-2,4-dithiolanyl]phenyl carboxylic acid (13) (Table 1)

Figure 23:
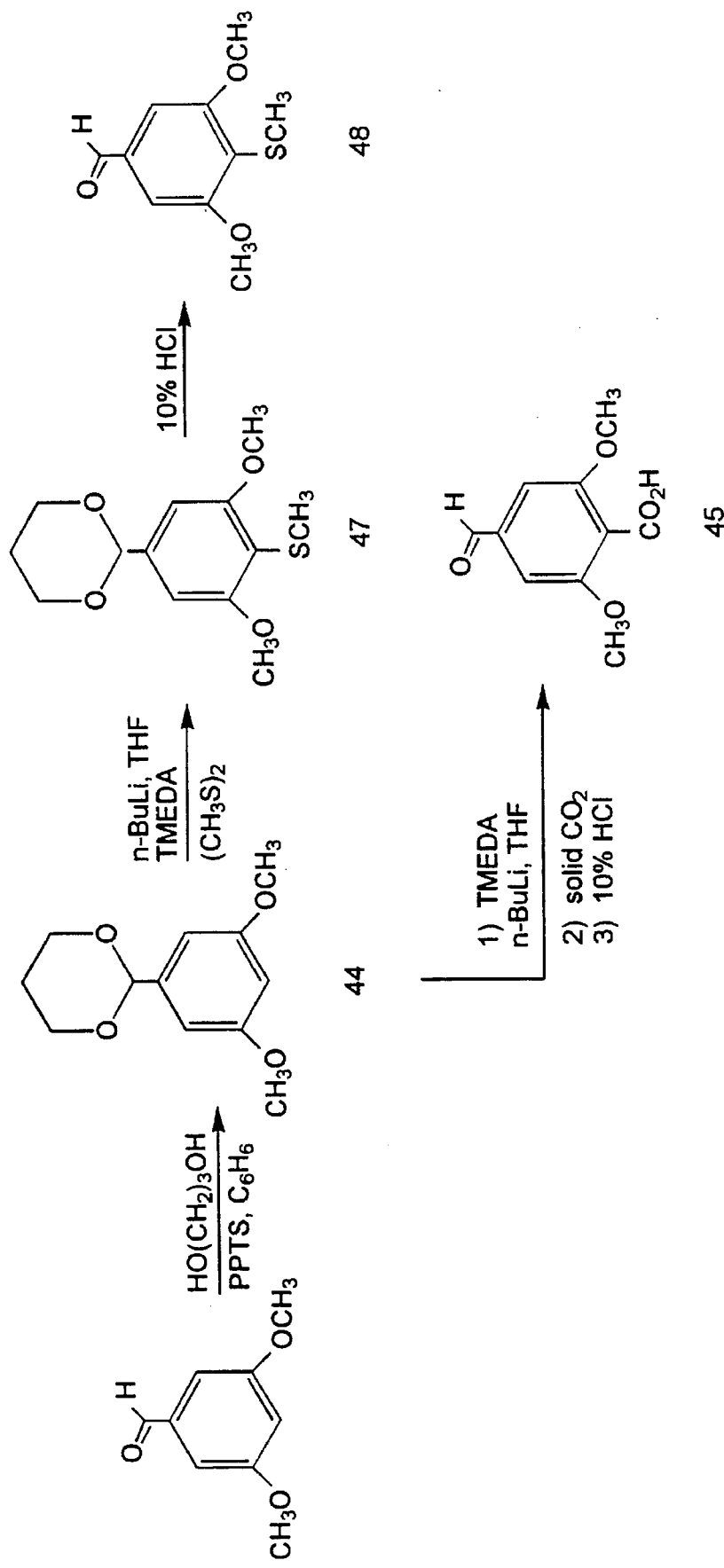
FIG. 23 is a schematic drawing showing the synthetic approach for producing 2,4-diaryl-1,3-dithiolane intermediates with a pm substituted aryl carboxylic acid or alkylthio functionalities.

Step A Preparation of 2-(3,5-dimethoxyphenyl)-1,3-dioxane (44) (FIG. 23)

3,5-dimethoxybenzaldehyde (5.00 g,30.12 mmole), 1,3-propanediol (9.15 g, 120.5 mmole), pyridinium para-toluenesulfonate (3.02 g, 12.05 mmole) and 80 ml dry benzene were refluxed with Dean-Stark removal of the benzene-water azeotrope for 12 hours. The benzene was removed in vacuo and the remaining oil redissolved in dichloromethane and was washed with 10% $NaHCO_3$ and $H_2O$. The organic layer was washed over $Na_2SO_4$ and concentrated to an oil in vacuo which was purified by flash column chromatography using 2:1 hexane/ethyl acetate containing 0.5% triethylamine as eluent. (5.731 g, 85%).

NMR: ($CDCl_3$) 1.45,dt,1H; 2.22,m, 1H; 3.79,s,6H; 3.97, dt,2H; 4.26,dd,2H; 5.43,s,1H; 6.43,t,1H; 6.65,d,2H. M.S. (CI): 225 (100%)

Step B Preparation of 2,6-dimethoxy-4-formylbenzoic acid (45) (FIG. 23)

Anhydrous TMEDA (2.05 ml, 13.62 mmole) and 90 ml dry THF was cooled to –78° C. under an argon atmosphere. n-Butyllithium (11.35 ml of a 1.20M soln.) was added and after 15 minutes, 2-(3,5-dimethoxyphenyl)-1,3-dioxane (44) (FIG. 23) (3.05 g, 13.62 mmole) predissolved in 50 ml dry THF was added. The reaction was warmed to 0° C. and was stirred at that temperature for an additional 60 minutes (the solution turned from a blood red color to a dark brown color). The aryl lithium solution was then poured onto solid carbon dioxide covered with anhydrous diethyl ether. A white precipitate formed immediately. When the reaction warmed to room temperature, 15 ml of 10% HCl was added and the reaction was stirred overnight. The product was then extracted into chloroform. The organic layer was dried over $MgSO_4$, and concentrated in vacuo to a white solid (1.311 g, 46%). The solid can be recrystallized from hexane/ethyl acetate.

NMR: ($CDCl_3$) 3.95,s,6H; 7.11,s,2H; 9.97,s,1H. M.S. (CI) 211 (100%) Melting Point 209°–211° C. Anal. Calcd. for $C_{10}H_{10}O_5$: C, 57.14; H,4.80. Found: C, 5.7.24; H, 4.82.

Step C Preparation of cis/trans-2,6-dimethoxy-4-[3-(3,4,5-trimethoxyphenyl)-2,4-dithiolanyl]phenyl carboxylic acid (13) (Table 1)

2,6-dimethoxy-4-formylbenzoic acid (45) (FIG. 23) (1.18 g, 5.62 mmole), 1-(3,4,5-trimethoxyphenyl)-1,2-ethanedithiol (39) (FIG. 19) (1.68 g, 6.46 mmole), pyridinium para-toluenesulfonate (0.564 g, 2.25 mmole) and 50 ml dry benzene were refluxed under an argon atmosphere with Dean-Stark removal of the benzene-water azeotrope for 8 hours. The benzene was removed in vacuo and the remaining oil purified by flash column chromatography using 2:1 ethyl acetate/hexane as eluent. The column yields 1.25 g (49%, 11 cis/trans) of a white foam. The solid can be recrystallized from dichloromethane/diethyl ether.

cis/trans epimers:

NMR: ($CDCl_3$) 3.50,dd,1H; 3.57,d,2H; 3.66,dd,1H; 3.84, s,3H; 3.84,s,3H; 3.86,s,6H; 3.88,s,6H; 3.91,s,6H; 3.93,s,6H; 4.88,t,1H; 5.03,dd,1H; 5.73,s,1H; 5.80,s,1H; 6.72,s,2H; 6.72,s,2H; 6.87,s,2H; 6.88,s,2H. M.S. (CI): 453 (100%) Melting Point 124°–125° C. Anal. Calcd. for $C_{21}H_{24}O_7S_2$: C, 55.74: H,5.34; S, 14.17. Found: C, 55.45; H, 5.41: S, 14.32.

EXAMPLE 24

Preparation of cis/trans-N-hydroxyl-N-methyl-[2,6-dimethoxy-4-{3-(3,4,5-trimethoxyphenyl)-2,4-dithiolanyl}]phenyl amide (14) (table 1)

1:1 cis/trans-2,6-dimethoxy-4-[3-(3,4,5-trimethoxyphenyl)-2,4-dithiolanyl]phenyl carboxylic acid (13) (table 1) (0.630 g, 1.30 mmole), dry DMF (111 µL) and 20 ml dry dichloromethane was cooled to 0° C. under an argon atmosphere. Oxalyl chloride (314 µL, 3.6 mmole) was added and the reaction stirred for 2 hours at 0° C. The acid chloride solution was then added to a solution of N-methylhydroxylamine hydrochloride (0.962 g, 11.52 mmole) predissolved in THF (20 ml), triethylamine (2.4 ml) and water (2.0 ml). The reaction was stirred at room temperature overnight. The reaction was quenched with 10% HCl end extracted with chloroform. The organic layer was dried over $MgSO_4$, and concentrated in vacuo to an oil which was purified by flash column chromatography using 2:1 ethyl acetate/hexane as eluent. The column yields 335 mg (54%) as a white foam (1:1 cis/trans).

cis/trans epimers

NMR: ($CDCl_3$) 3.13,s,6H; 3.45,dd,1H; 3.50,d,2H; 3.59, dd,1H; 3.3.77,s,6H; 3.77,s,6H; 3.78,s,6H; 3.79,s,6H; 3.81, s,6H; 4.81,t,1H; 5.00,dd,1H; 5.68,s,1H; 5.76,s,1H; 6.68,s, 2H; 6.69,s,2H; 6.78,bs,4H. M.S. (CI) 482, 391,89 (100%) Melting point 148°–153° C. Anal. Calcd. for $C_{22}H_{27}O_7S_2N$ C, 54.87; H, 5.65; S, 13.32; N, 2.91. Found C, 54.98; H, 5.69; S, 13.21; N, 2.89.

EXAMPLE 25

Cis/trans-ethyl-4'-[2,6-dimethoxy-4-{3-(3,4,5-trimethoxyphenyl)-2,4-dithiolanyl}]phenoxybutyrate (15) (table 1)

Step A Preparation of ethyl-4'-(2,6-dimethoxy-4-formyl) phenoxybutyrate (46)

Syringe aldehyde (2.00 g, 11.0 mmole), potassium carbonate (3.96 g, 28.69 mmole), sodium iodide (2.46 g, 16.4 mmole), ethyl 4-bromobutyrate (5.559 g, 28.5 mmole) and 15 ml dry DMF were stirred under a nitrogen atmosphere at 70° C. for 24 hours. The reaction was quenched with 100 ml $H_2O$ and extracted with dichloromethane. The organic layer was dried over $MgSO_4$, and concentrated to an oil which was purified by flash column chromatography using 2:1 hexane/ethyl acetate as eluent. The column yielded 2.689 g (83%) as a colorless oil.

NMR: ($CDCl_3$) 1.25,t,3H; 2.05,m,2H; 2.60,t,2H; 3.90,s, 6H; 4.12,m,4H; 7.11,s,2H; 9.86,s,1H. M.S. (CI): 297,251, 115 (100%)

Step B Preparation of cis/trans-ethyl-4'-[2,6-dimethoxy-4-{3-(3,4,5-trimethoxyphenyl)-2,4-dithiolanyl}] phenoxybutyrate (15) (table 1)

ethyl-4'-(2,6-dimethoxy-4-formyl)phenoxybutyrate (46) (0.825 g, 2.79 mmole), 1-(3,4,5-trimethoxyphenyl)-1,2-ethanedithiol (39) (FIG. 19) (0.833 g, 3.205 mmole), pyridinium para-toluenesulfonate (0.280 g, 1.116 mmole) and 50 ml dry benzene were refluxed under an argon atmosphere with Dean-Stark removal of the benzene-water azeotrope overnight. The benzene was removed in vacuo and the remaining oil purified by flash column chromatography using 1:2 ethyl acetate/hexane as eluent. The column yields 1.346 g (90%, 1:1 cis/trans) of a colorless oil.

cis/trans epimers:

NMR: ($CDCl_3$) 1.23,t,6H; 2.02,m,4H; 2.59,t,4H; 3.47,dd, 1H; 3.55,d,2H; 3.64,dd,1H; 3.84–3.87,5s,30H; 3.99,t,4H; 4.13,q,4H; 4.83,t,1H; 5.05,dd, 1H; 5.74,s,1H; 5.82,s,1H; 6.72,s,2H; 6.75,s,2H; 6.81,s,2H; 6.83,s,2H. M.S. (CI) 538 (100%)

EXAMPLE 26

Preparation of cis/trans-4'-[2,6-dimethoxy-4-{3-(3,4,5-trimethoxyphenyl)-2,4-dithiolanyl}] phenoxybutyric acid (16) (table 1)

1:1 Cis/trans-ethyl-4'-[2,6-dimethoxy-4-{3-(3,4,5-trimethoxyphenyl)-2,4-dithiolanyl}]phenoxybutyrate (15) (table 1) (1.346 g, 2.5 mmole) was dissolved in 15 ml THF. To this solution was added lithium hydroxide monohydrate (136 mg, 3.25 mmole) predissolved in 3 ml $H_2O$. The reaction was stirred at room temperature overnight. 10% HCl was added and the product was extracted into chloroform. The organic layer was dried over $MgSO_4$ and concentrated in vacuo to an oil which was purified by flash column chromatography using 100% ethyl acetate as eluent to give 715 mg (56%) of a white foam (1:1 cis/trans).

cis/trans epimers:

NMR: ($CDCl_3$) 2.04,m,4H; 2.69,t,4H; 3.47,dd,1H; 3.54, d,2H; 3.64,dd,1H; 3.84–3.87,5s,30H; 4.00,t,4H; 4.13, g,4H; 4.83,t,1H; 5.06,dd,1H; 5.74,s,1H; 5.82,s,1H; 6.72,s,2H; 6.75,s,2H; 6.81,s,2H; 6.84,s,2H. M.S. (CI) 511 (100%)

EXAMPLE 27

Preparation of cis/trans-N-hydroxyl-N-methyl-4'-[2,6-dimethoxy-4-{3-(3,4,5-trimethoxyphenyl)-2,4-dithiolanyl}]phenoxybutyramide (17) (table 1)

1:1 cis/trans-4'-[2,6-dimethoxy-4-{3-(3,4,5-trimethoxyphenyl)-2,4-dithiolanyl}]phenoxybutyric acid (16) (table 1) (0.215 g, 0.421 mmole), dry DMF (33 µL) and 20 ml dry dichloromethane was cooled to 0° C. under an argon atmosphere. Oxalyl chloride (110 µL, 1.26 mmole) was added and the reaction stirred for 1 hour at 0° C. The acid chloride solution was then added to a solution of N-methylhydroxylamine hydrochloride (0.421 g,5.04 mmole) predissolved in THF (10 ml), triethylamine (0.765 g) and water (1.0 ml). The reaction was stirred at room temperature overnight. The reaction was quenched with 10% HCl and extracted with chloroform. The organic layer was dried over $MgSO_4$, and concentrated in vacuo to an oil which was purified by flash column chromatography using 2:1 ethyl acetate/hexane as eluent. The column yields 167 mg (74%) as a white foam (1:1 cis/trans).

Cis/trans epimers:

NMR: ($CDCl_3$) 2.11,m,4H; 2.65,m,2H; 2.82,m,2H; 3.29, s,3H; 3.40,s,3H; 3.47,dd,1H; 3.56,d,1H; 3.65,dd,1H; 3.84, s,6H; 3.86,s,12H; 3.88,s,12H; 3.98,m,4H; 4.84,t,1H; 5.06, dd,1H; 5.75,s,1H; 5.82,s,1H; 6.72,s,2H; 6.75,s,2H; 6.85,2s, 2H. M.S. (CI) 540, 298, 195 (100%).

EXAMPLE 28

Cis and trans-2-(3,5-dimethoxy-4-methylthiophenyl) -4-(3,4,5-trimethoxyphenyl)-1,3-dithiolane (18) (table 1)

Step A Preparation of 2-3,5-dimethoxy-4-methylthiophenyl)-1,3-dioxane (47) (FIG. 23)

TMEDA (898 µl,5.95 mmole) and dry THF (20 ml) were cooled to −78° C. under an argon atmosphere and 1.5M n-butyl lithium (3.96 ml) was added. The solution was kept at −78° C. for 15 minutes and then 2-(3,5-dimethoxyphenyl) -1,3-dioxane (42) (FIG. 22) (1.212 g,5.41 mmole) predissolved in 10 ml dry THF was added. The solution turned blood red in color after being warmed to 0° C. and stirring at that temperature for 1 hour. To this solution at 0° C. was added methyl disulfide (535 µl,5.95 mmole) and the reaction was stirred for two hours and then allowed to warm to room temperature. The reaction was quenched with 10% $NaHCO_3$, and extracted with diethyl ether. The organic layer was dried over anhydrous sodium sulfate, and evaporated in vacuo to an oil which was purified by flash column chromatography using 2:1 hexane/ethyl acetate as eluent. (0.957 g, 66%) (oil).

NMR: ($CDCl_3$) 1.46,dt,1H; 2.23,m,1H; 2.32,s,3H; 3.91, s,6H; 3.99,dt,2H; 4.28,dd,2H; 5.46,s,1H; 6.71,s,2H. M.S. (CI) 271 (100%).

Step B Preparation of 3,5-dimethoxy-4-methylthiobenzaldehyde (48) (FIG. 23)

2-(3,5-dimethoxy-4-methylthiophenyl)-1,3-dioxane (47) (0.945 g, 3.5 mmole) was dissolved in 15 ml THF and 7 ml of 10% HCl was added. The solution was stirred overnight at room temperature. The aldehyde was extracted into diethyl ether, dried over $MgSO_4$, and concentrated in vacuo to an oil. (0.742 g, 90%).

NMR: ($CDCl_3$) 2.45,s,3H; 3.97,s,6H; 7.06,s,2H; 9.92,s, 1H. M.S. (CI): 213 (100%).

Step C Preparation of cis and trans-2-(3,5-dimethoxy-4-methylthiophenyl)-4-(-3,4,5-trimethoxyphenyl)-1,3-dithiolane (18) (table 1)

1-(3,4,5-trimethoxyphenyl)-1,2-ethanedithiol (39) (0.148 g,0.57 mmole), 3,5-dimethoxy-4-methylthiobenzaldehyde (48) (FIG. 23) (0.11 g, 0.519 mmole) and 0.052 g of pyridinium para-toluenesulfonate was added to 40 ml dry benzene and refluxed with Dean-Stark removal of the benzene- water azeotrope for 48 hours. The benzene was removed in vacuo, and the remaining oil redissolved in dichloromethane. The organic layer was washed with 3×30 ml H$_2$O and was dried over MgSO$_4$, and evaporated in vacuo to an oil which was purified by flash column chromatography with 2:1 hex/ethyl acetate as eluent. The product mixture contains a 1.0/1.0 cis/trans ratio (0.151 g, 64%). The trans isomer was isolated after two recrytallizations of this mixture from methanol.

trans epimer

NMR: (CDCl$_3$) 1.45,s,18H; 3.42–3.70,m,4H; 3.84,s,3H; 3.88,s,6H; 5.10,dd,1H; 5.24,s,1H; 5.88,s,1H; 6.73,s,2H; 7.38,s,2H. M.S. (CI): 455 (100%). Melting Point 140°–142.5° C. Anal. calcd. for C$_{21}$H$_{26}$O$_5$S$_3$: C, 55.48; H, 5.76; S, 21.16. Found: C, 55.39; H, 5.78; S, 21.08.

EXAMPLE 29

Preparation of trans 2-(4-hydroxy-5-iodo-3-methoxyphenyl)-4-(3,4,5-trimethoxyphenyl)-1,3-dithiolane (19) (table 1)

1-(3,4,5-trimethoxyphenyl)-1,2-ethanedithiol (32) (FIG. 26) (0.500 g, 1.92 mmole), 5-iodovanillin (0.411 g, 1.48 mmole), pyridinium para-toluenesulfonate (0.193 g, 0.769 mmole) and 50 ml dry benzene were refluxed under an argon atmosphere with Dean-Stark removal of the benzene-water azeotrope for 12 hours. The benzene was removed in vacuo, and the remaining oil redissolved in dichloromethane. The organic layer was washed with 3×30 ml H$_2$O and was dried over MgSO$_4$, and evaporated in vacuo to an oil which was purified by flash column chromatography with 2:1 hex/ethyl acetate as eluent. The product mixture contains a 1.0/1.3 cis/trans ratio (0.578 g, 75%) after one crystallization from methanol. The trans isomer (50 mg) was isolated after one additional crytallization from ethanol.

Trans epimer:

NMR: (CDCl$_3$) 3.49,dd,1H; 3.64,dd,1H; 3.84,s,3H; 3.88, s,6H; 3.93,s,3H; 5.05,dd,1H; 5.76,s,1H; 6.11,s,1H; 6.72,s, 2H; 7.10,d,1H; 7.50,d,1H. M.S. (IBu) 521 (100%). Melting Point 145°–146° C. Anal. calcd. for C$_{19}$H$_{21}$O$_5$S$_2$I: C, 43.85; H, 4.07; S,12.32. Found: C, 43.93; H, 4.09; S, 12.42.

EXAMPLE 30

Preparation of cis/trans 2-(3,4-dimethoxy-5-iodophenyl)-4-(3,4,5-trimethoxyphenyl)-1,3-dithiolane (20) (table 1)

1-(3,4,5-trimethoxyphenyl)-1,2-ethanedithiol (39) (FIG. 19) (1.404 g,5.40 mmole), 3,4-dimethoxy-5-iodobenzaldehyde (41) (FIG. 22) (1.30 g, 4.45 mmole) and 0.542 g of pyridinium para-toluenesulfonate was added to 50 ml dry benzene and refluxed with Dean-Stark removal of the benzene- water azeotrope for 12 hours. The benzene was removed in vacuo, and the remaining oil redissolved in ethyl acetate. The organic layer was washed with 10% NaHCO$_3$ and H$_2$O. The organic layer was dried over MgSO$_4$, and evaporated in vacuo to an oil which was purified by flash column chromatography with 2:1 hex/ethyl acetate as eluent. The product mixture contains a 1.0/1.0 cis/trans ratio (2.38 g, 100%). The trans isomer can be isolated by recrystallization from methanol.

Trans epimer:

NMR: (CDCl$_3$) 3.47,dd,1H; 3.63,dd,1H; 3.82,s,3H; 3.84, s,3H; 3.88,s,9H; 5.05,dd,1H; 5.74,s,1H; 6.72,s,2H; 7.26,d, 1H; 7.56,d,1H. M.S. (CI): 534, 501, 409, 309, 227, 195 (100%). Melting Point 117°–118° C. (Recrystallized from methanol). Anal. calcd. for C$_{20}$H$_{23}$O$_5$S$_2$I: C, 44.95; H, 4.34; S, 12.00. Found: C, 45.01; H, 4.35; S, 12.08.

EXAMPLE 31

Cis/trans 2-(5-cyano-3,4-dimethoxyphenyl)-4-(3,4, 5-trimethoxyphenyl)-1,3-dithiolane (21) (table 1)

Step A Preparation of 5-cyano-3,4-dimethoxybenzaldehyde (47) (FIG. 22)

3,4-dimethoxy-5-iodobenzaldehyde (41) (FIG. 22) (4.40 g, 15.07 mmole), copper cyanide (13.5 g, 150.7 mmole) and dry DMF (45 ml) were stirred under an argon atmosphere for 18 hours at 140° C. The reaction was cooled to room temperature, filtered through celite, and the filtrate concentrated to an oil in vacuo. The dark brown oil was purified through a short flash silica column using 11 hexane/ethyl acetate as eluent to yield 2.87 g (69%) of a white solid.

NMR: (CDCl$_3$) 3.96,s,3H; 4.18,s,3H; 7.61,d, 1H; 7.64,d, 1H; 9.87,s,1H. M.S. (CI): 383, 192 (100%).

Step B Preparation of cis/trans 2-(5-cyano-3,4-dimethoxyphenyl)-4-(3,4,5-trimethoxyphenyl)-1,3-dithiolane (21)

1-(3,4,5-trimethoxyphenyl)-1,2-ethanedithiol (2.36 g, 9.09 mmole), 5-cyano-3,4-dimethoxybenzaldehyde (49) (1.50 g, 7.85 mmole) and 0.788 g of pyridinium para-toluenesulfonate was added to 50 ml dry benzene and refluxed with Dean-Stark removal of the benzene-water azeotrope for 24 hours. The benzene was removed in vacuo, and the remaining oil redissolved in ethyl acetate. The organic layer was washed with 10% NaHCO$_3$ and H$_2$O. The organic layer was dried over MgSO$_4$, and evaporated in vacuo to an oil which was purified by flash column chromatography with 2:1 hex/ethyl acetate as eluent. The product mixture contains a 1.0/1.0 cis/trans ratio (2.91 g, 86%).

Trans/cis epimers: NMR: (CDCl$_3$) 3.49,dd,2H; 3.56,d, 4H; 3.65,dd,2H; 3.84,s,6H; 3.87,s,12H; 3.89,s,3H; 3.92,s, 3H; 4.02,s,6H; 4.86,t,1H; 5.04,dd,1H; 5.68,s,1H; 5.75,s,1H; 6.71,s,2H; 6.72,s,2H; 7.32,bd,2H; 7.37,d,1H; 7.42,d,1H. M.S. (CI) 434 (100%). Melting Point 103°–106° C. Anal. calcd. for C$_{21}$H$_{23}$O$_5$NS$_2$: C, 58.18; H, 5.35; S,14.79; N. 3.23. Found: C, 58.00: H, 5.38; S, 14.93; N, 3.21.

EXAMPLE 32

Cis/trans-2-(3-(2-hydroxyethylsufonyl)-5-methoxy-4-propoxyphenyl)-4-(3,4,5- trimethoxyphenyl)-1,3-dithiolane (22)

Figure 24:
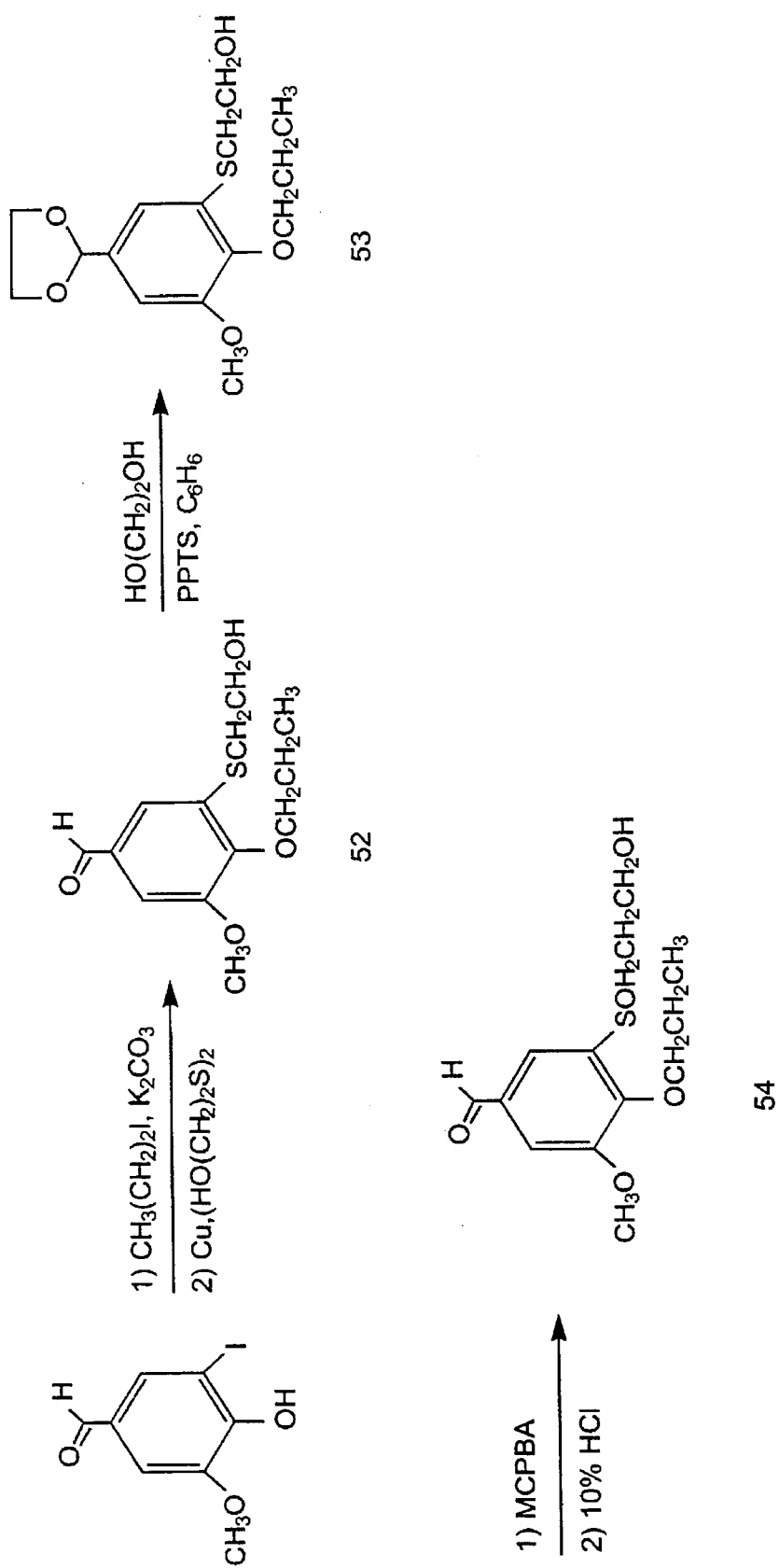
FIG. 24 is a schematic drawing showing the synthetic approach for producing 2,4-diaryl-1,3-dithiolane intermediates with a M= substituted aryl sulfonyl functionalities.

Step A Preparation of 3-(2-hydroxyethylthio)-5-methoxy-4-propoxybenzaldehyde (52) (FIG. 24)

5-iodo-3-methoxy-4-propoxybenzaldehyde (6.166 g,19.27 mmole). copper powder (10.41 g,163.78 mmole) and 45 ml DMF were stirred vigorously under an N$_2$ atmosphere at 140° C. for 3 hours. To this slurry was added 2-hydroxyethyldisulfide (4.75 g,30.8 mmole) predissolved in 10 ml DMF. The reaction was stirred at 140° C. overnight. The copper was removed by suction filtration through celite, and was washed thoroughly with ethyl acetate. The filtrate was concentrated to an oil in vacuo and then redissolved in dichloromethane. The organic layer was washed with H$_2$O, dried over MgSO$_4$, and concentrated to an oil in vacuo which was purified by flash column chromatography using 1:1 hex/ethyl acetate as eluent to yield a light yellow oil (4.00 g, 77%).

NMR: (CDCl$_3$) 1.06,t,3H; 1.85,m,2H; 3.13,t,2H; 3.74,t, 2H; 3.91,s,3H; 4.08,t,2H; 7.31,d,1H; 7.46,d,1H; 9.86,s,1H. M.S. (CI): 271 (100%).

Step B Preparation of 2-(3-(2-hydroxyethylthio)-5-methoxy-4-propoxyphenyl)-1,3-dioxalane (53) (FIG. 24)

3-(2-hydroxyethylthio)-5-methoxy-4-propoxybenzaldehyde (52) (FIG. 24) (0.738 g,2.73 mmole), ethylene glycol (0.678 g,10.92 mmole), PPTS (0.274 g, 1.09 mmole) and 40 ml benzene were refluxed with Dean-Stark removal of the benzene-water azeotrope for 5 hours. The benzene was removed in vacuo and the remaing oil redissolved in $CH_2Cl_2$ which was washed with 10% $NaHCO_3$, $H_2O$ and dried over sodium sulfate. The solvent was removed in vacuo and the oil purified by flash column chromatography using 2:1 hex/ethyl acetate as eluent to yield a light tan oil (0.616 g, 71%).

NMR: ($CDCl_3$) 1.03,t,3H; 1.84,m,2H; 3.05,t,2H; 3.66,t, 2H; 3.85,s,3H; 3.95,t,2H; 4.07,m,4H; 5.71,s,1H; 6.93,d,1H; 7.08,d, 1H.

Step C Preparation of 3-(2-hydroxyethylsulfonyl)-5-methoxy-4-propoxybenzaldehyde (54) (FIG. 24)

2-(3-(2-hydroxyethylthio)-5-methoxy-4-propoxyphenyl)-1,3-dioxalane (53) (FIG. 24) (2.11 g,6.70 mmole) was dissolved in 15 ml $CH_2Cl_2$ and was cooled to 0° C. under an $N_2$- atmosphere. To this solution was slowly added 80% MCPBA (3.32 g,15.41 mmole) along with an additional 10 ml $CH_2Cl_2$. The reaction was allowed to warm to room temperature over a 6 hour period. The m-chloro-benzoic acid precipitate was removed by suction filtration end the filtrate was washed with 10% $NaHCO_3$ and $H_2O$. The organic layer was then added to 20 ml 10% HCl and the mixture was stirred vigorously overnight. The organic layer was separated, dried over $MgSO_4$, and evaporated to an impure white solid which was purified by flash column chromatography using 2:1 hexane/ethyl acetate as eluent to yield a white solid (1.20 g, 60%).

NMR: ($CDCl_3$) 1.03,t,3H; 1.88,m,2H; 2.70,br s,1H; 3.65, t,2H; 3.96,s,3H; 3.98,t,2H; 4.24,t,2H; 7.68,d,1H; 7.80,d,1H; 9.93,s,1H. M.S. (IBu) 302 (100%). Melting Point 111°–112° C. Anal. calcd. for $C_{13}H_{18}O_6S$: C, 51.64; H, 6.00; S,10.60. Found: C, 51.67; H,5.99; S, 10.52.

Figure 25:
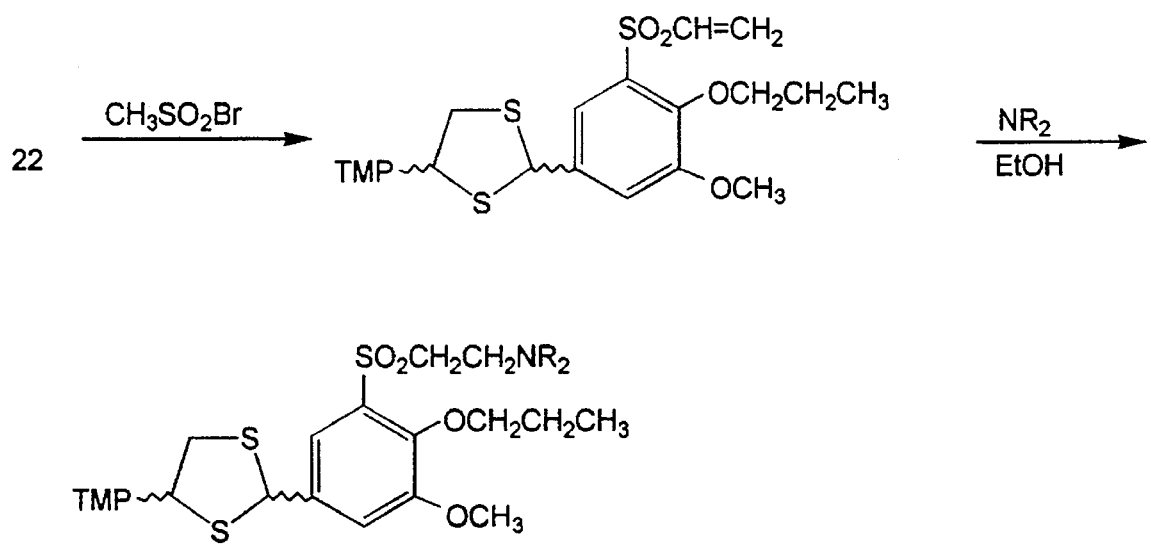
FIG. 25 is a schematic drawing showing the synthetic approach for producing 2,4-diaryl-1,3-dithiolane compounds with various substituted aryl amino ethylsulfonyl functionalities.

Step D Preparation of cis/trans2-(3-(2-hydroxyethylsulfonyl)-5-methoxy-4-propoxyphenyl)-4-(3,4,5-trimethoxyphenyl)-1,3-dithiolane (22) (FIG. 25)

1-(3-(2-hydroxyethylsulfonyl)-5-methoxy-4-propoxybenzaldehyde (54) (FIG. 24) (0.88 g,2.91 mmole), 1-(3,4,5-trimethoxyphenyl)-1,2-ethanedithiol (39) (FIG. 19) (0.947 g, 3.64 mmole) and 0.365 g of pyridinium para-toluene sulfonate was added to 120 ml dry benzene and refluxed with Dean-Stark removal of the benzene- water azeotrope for 24 hours. The benzene was removed in vacuo, and the remaining oil redissolved in dichloromethane. The organic layer was washed with 10% $NaHCO_3$ and $H_2O$. The organic layer was dried over $MgSO_4$, and evaporated in vacuo to an oil which was purified by flash column chromatography with 1:1 hex/ethyl acetate as eluent. The product mixture (white foam) contains a 1.0/1.0 cis/trans ratio (1.254 g, 79%).

trans/cis epimers:

NMR: ($CDCl_3$) 1.04,t,6H; 1.87,m,4H; 3.45–3.60,m,4H; 3.64,t,4H; 3.92,s,12H; 3.95,s,6H; 3.97,t,4H; 4.12,t,4H; 4.88, dd,1H; 5.07,dd,1H; 5.53,s,2H; 5.74,s,1H; 5.82,s,1H; 6.73,s, 2H; 6.76,s,2H; 7.41,d, 1H; 7.43,d,1H; 7.71,d, 1H; 7.80,d, 1H. M.S. (IBu): 544 (100%) Melting Point 56°–60° C. Anal. calcd. for $C_{24}H_{32}O_8S_3$: C, 52.92; H, 5.92; S,17.66. Found C, 52.72; H,5.89; S, 17.53.

EXAMPLE 33

Preparation of cis/trans-2-(3-(vinylsufonyl)-5-methoxy-4-propoxyphenyl)-4-(3,4,5-trimethoxyphenyl)-1,3-dithiolane (23) (FIG. 25)

1:1 cis/trans-2-(3-(2-hydroxyethylsulfonyl)-5-methoxy-4-propoxyphenyl)-4-(3,4,5-trimethoxyphenyl)-1,3-dithiolane (22) (FIG. 25) (0.30 g,0.55 mmole), pyridine (90 µl) and 15 ml dry chloroform was stirred under an argon atmosphere. To this solution was added methane sulfonyl bromide (0.108 g,0.679 mmole) predissolved in 1 ml dry chloroform. The reaction was stirred at room temperature for 4 hours. TLC shows no change, however, the solvent is removed in vacuo and the remaining oil added to a flash silica column using 2:1 hex/ethyl acetate as eluent. The vinyl sulfone compound is formed on the column and only one product eludes off the column. The product mixture (foam) contains a 1.0/1.0 cis/trans ratio (0.236 g, 82%).

cis/trans epimers:

NMR: ($CDCl_3$) 1.03,t,6H; 1.86,m,4H; 3.45–3.70,m,4H; 3.84,s,6H; 3.88,s,12H; 3.89,s,3H; 3.92,s,3H; 4.12,t,4H; 4.87,dd,1H; 5.07,dd,1H; 5.73,s,1H; 5.82,s,1H; 6.05,d,2H; 6.42,d,1H; 6.49,d,1H; 6.72,s,2H; 6.75,s,2H; 7.00,dd,2H; 7.38,d,1H; 7.40,d,1H; 7.71,d,1H; 7.80,d,1H. M.S. (CI): 527 (100%) 227, 195.

EXAMPLE 34

Preparation of cis/trans-2-(3-(2-N,N-dimethylaminoethylsulfonyl)-4-propoxy-5-methoxyphenyl)-4-(3,4,5-trimethoxyphenyl)-1,3-dithiolane (24) (FIG. 25)

2-(3-(vinylsufonyl)-5-methoxy-4-propoxyphenyl)-4-(3,4,5-trimethoxyphenyl)-1,3-dithiolane (22) (FIG. 25) (0.035 g,0.0821 mmole) was dissolved in absolute ethanol (5 ml) which was cooled to 0° C. under an argon atmosphere. Dimethylamine gas was then condensed into the reaction until 10 drops of amine were added. The reaction was stirred at 0° C. for 3 hours. The solvent and excess amine were removed in vacuo, and the remaining oil purified by flash column chromatography with 1:1 hex/ethyl acetate as eluent. The product mixture (oil) contains a 1.0/1.0 cis/trans ratio (0.036 g, 78%).

cis/trans epimer:

NMR: ($CDCl_3$) 1.03,t,6H; 1.86,m,4H; 2.21,s,12H; 2.74, dt,4H; 3.45–3.70,m,4H; 3.63,t,4H; 3.83,s,6H; 3.87,s,12H; 3.90,s,3H; 3.93,s,3H; 4.11,t,4H; 4.88,dd,1H; 5.07,dd.1H; 5.73,1H; 5.81,s,1H; 6.71,s,2H; 6.74,s,2H; 7.39,d,1H; 7.41, d,1H; 7.66,d,1H; 7.75,d,1H. M.S. (CI): 572,389, 346, 330, 227, 195 (100%).

EXAMPLE 35

Preparation of cis/trans-2-(3-(2-N,N-diethylaminoethylsulfonyl)-4-propoxy-5-methoxyphenyl)-4-(3,4,5-trimethoxyphenyl)-1-3-dithiolane (25) (FIG. 25)

2-(3-(vinylsulfonyl)-5-methoxy-4-propoxyphenyl)-4-(3,4,5-trimethoxyphenyl)-1,3-dithiolane (22) (FIG. 25) (0.015 g,0.076 mmole) was dissolved in absolute ethanol (10 ml) and diethylamine (2 drops) was into the reaction which was stirred at room temperature for 24 hours. The solvent and excess amine were removed in vacuo, and the remaining oil purified by flash column chromatography with 1:1 hex/ethyl acetate as eluent. The product mixture (oil) contains a 1.0/1.0 cis/trans ratio (0.0049 g, 29%).

cis/trans epimer:

NMR: ($CDCl_3$) 0.94,dt,6H; 1.04,t,6H; 1.86,m,4H; 2.43, dq,6H; 2.92,dt,4H; 3.45–3.70,m,4H; 3.63,t,4H; 3.83,s,6H; 3.87,s,12H; 3.90,s,3H; 3.93,s,3H; 4.11,t,4H; 4.87,dd,1H; 5.07,dd,1H; 5.73,1H; 5.82,s,1H; 6.72,s,2H; 6.75,s,2H; 7.38, d,1H; 7.40,d,1H; 7.68,d,1H; 7.76,d,1H. M.S. (CI) 600, 402, 374,358,227, 195, 100 (100%).

EXAMPLE 36

Preparation of cis/trans-2-(3-(2-morpholinoethylsulfonyl)-4-propoxy-5-methoxyphenyl)-4-(3,4,5-trimethoxyphenyl)-1,3-dithiolane (26) (FIG. 25):

2-(3-(vinylsufonyl)-5-methoxy-4-propoxyphenyl)-4-(3,4,5-methoxyphenyl)-1,3-dithiolane (22) (FIG. 25) (0.040 g,0.076 mmole) was dissolved in absolute ethanol (10 ml) and morpholine (13 ml) was into the reaction which was stirred at room temperature for 4 hours. The solvent and excess amine were removed in vacuo, and the remaining oil purified by flash column chromatography with 1:1 hex/ethyl acetate as eluent. The product mixture (oil) contains a 1.0/1.0 cis/trans ratio (0.022.5 g, 49%).

Cis/trans epimers:

NMR: ($CDCl_3$) 1.03,t,6H; 1.86,m,4H; 2.31,t,8H; 2.74,dt, 4H; 3.39,t,8H; 3.45–3.70,m,4H; 3.84,s,6H; 3.88,s,12H; 3.91,s,3H; 3.93,s,3H; 4.11,t,4H; 4.86,dd,1H; 5.07,dd,1H; 5.73,1H; 5.82,s,1H; 6.71,s,2H; 6.75,s,2H; 7.38,d,1H; 7.40, d,1H; 7.68,d,1H; 7.76,d,1H. M.S. (CI) 614, 372, 195 (100%).

EXAMPLE 37

Figure 26:
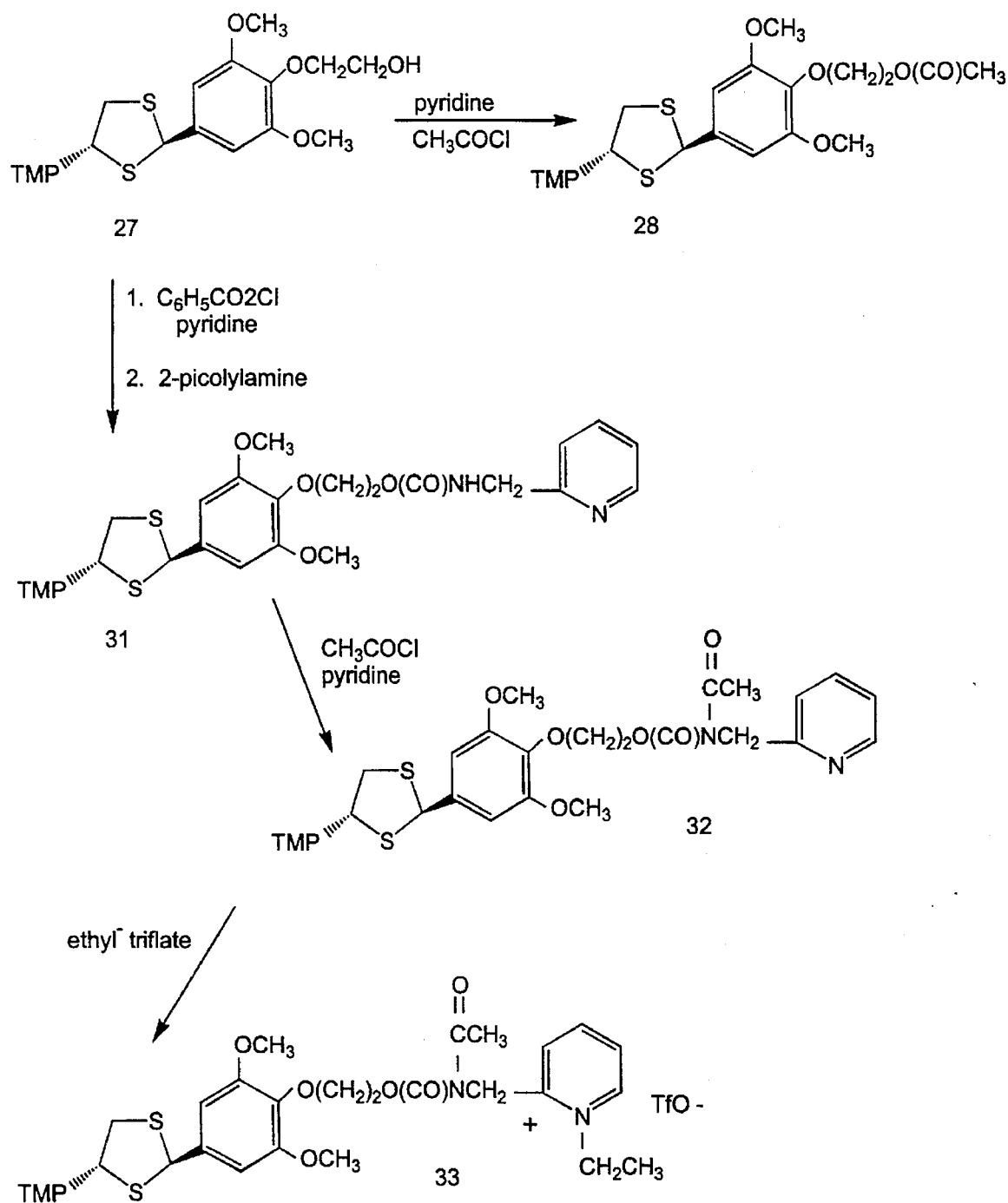
FIG. 26 is a schematic drawing showing the synthetic approach for producing 2,4-diaryl-1,3-dithiolane compounds with a quaternary alkyl pyridine side chain and its analogs functionalities.

Trans-2-(3,5-dimethoxy-4-(2'-hydroxyethoxy)phenyl)-4-(3,4,5-trimethoxyphenyl)-1,3-dithiolane (27) (FIG. 26)

Step A Preparation of 3,5-dimethoxy-4-(2'-hydroxyethoxy)benzaldehyde (55)

Syringaldehyde (1.0 g,5.49 mmole), 2-iodo-1-ethanol (1.90 g,10.98 mmole) and potassium carbonate (1.90 g, 13.77 mmole) were added to 15 ml dry DMF and stirred for 24 hours at 80° C. under an argon atmosphere. The reaction mixture was added to 100 ml $H_2O$ and acidified with 10% HCl. The product was extracted into $CHCl_3$, dried over $MgSO_4$, and concentrated to an oil in vacuo. The remaining oil was purified by flash column chromatography using 1:1 hex/ethyl acetate as eluent (1.009 g, 81%). NMR: ($CDCl_3$) 3.23,t,1H; 3.73,m,2H; 3.93,s,6H; 4.20,t,2H; 7.13,s,2H; 9.87, s,1H M.S. (CI): 227 (100%).

Step B Preparation of trans-2-(3,5-dimethoxy-4-(2'-hydroxyethoxy))-4-(3,4,5-trimethoxyphenyl)-1,3-dithiolane (27) (FIG. 26)

3,5-dimethoxy-4-(2-hydroxyethoxy)benzaldehyde (55) (2.14 g,9.47 mmole), 1-(3,4,5-trimethoxyphenyl)-1,2-ethanedithiol (39) (FIG. 19) (2.54 g,9.77 mmole) and 1.00 g of pyridinium para-toluene sulfonate was added to 75 ml dry benzene and refluxed with Dean-Stark removal of the benzene-water azeotrope for 24 hours. The benzene was removed in vacuo, end the remaining oil redissolved in ethyl acetate. The organic layer was washed with 10% HCl and $H_2O$. The organic layer was dried over $MgSO_4$, filtered, and evaporated in vacuo to an oil which was purified by flash column chromatography with 12 hex/ethyl acetate as eluent. The product mixture (white foam) titurates to a solid in diethylether (3.10 g,70%). The trans isomer was isolated after three recrystallizations from $CH_2Cl_2$/hexane (1.00 g).

Trans epimer:

NMR: ($CDCl_3$) 3.40,t,1H; 3.48,dd,1H; 3.64,dd,; 3.72,m, 2H; 3.84,s,3H; 3.88,s,6H; 3.90,s,6H; 4.13,t,2H; 5.06,dd,1H; 5.83,s,1H; 6.72,s,2H; 6.85,s,2H. M.S. (CI): 469 (100%). Melting point 121°–122° C. Anal. calcd. for $C_{22}H_{28}O_7S_2$: C, 56.39; H, 6.02; S,13.68. Found: C, 56.45; H,6.05; S, 13.62.

EXAMPLE 38

Preparation of trans-2-(3,5-dimethoxy-4-(2'-acetoxyethoxy)phenyl)-4-(3,4,5-trimethoxyphenyl)-1,3-dithiolane (28) (FIG. 26)

Trans-2-(3,5-dimethoxy-4-(2'-hydroxyethoxyphenyl))-4-(3,4,5-trimethoxyphenyl)-1,3-dithiolane (27) (FIG. 26) (0.05 g,0.107 mmole) was dissolved in 5 ml dry chloroform and 20 µl of pyridine was added. The reaction was cooled to 0° C. under an argon atmosphere and 10 µl of acetyl chloride was added. The reaction was allowed to warm to room temperature and stir for 2 hours. The reaction was quenched with 10% HCl and extracted with chloroform. The organic layer was washed with $H_2O$, dried over $MgSO_4$ and concentrated to a yellow oil which was purified by flash column chromatography using 2:1 hexane/ethyl acetate as eluent. The column yields 34 mg of the desired acetate as a white foam (63% yield).

Trans epimer:

NMR: ($CDCl_3$) 2.07,s,3H; 3.46,dd,1H; 3.48,dd,1H; 3.63, dd,1H; 3.83,s,3H; 3.86,s,6H; 3.87,s,6H; 4.18,t,2H; 4.33,t, 2H; 5.05,dd,1H; 5.80,s,1H; 6.71,s,2H; 6.81,s,2H. M.S. (CI): 540, 298, 195 (100%).

EXAMPLE 39

N'-hydroxyl-N'-methyl-N-[2,3-dimethoxy-5-{3-(3,4,5-trimethoxyphenyl)-2,4-dithiolanyl}]benzyl urea (29) (table 1)

Step A Preparation of 2-(5-cyano-3,4-dimethoxyphenyl)-1,3-dioxolane (50) (FIG. 22)

2-(3,4-dimethoxy-5-iodophenyl)-1,3-dioxolane (42) (FIG. 22) (2.80 g, 8.0 mmole), copper cyanide (5.7 g, 32.0 mmole) and dry DMF (50 ml) were stirred under an argon atmosphere for 24 hours at 140° C. The reaction was cooled to room temperature, filtered through celite, and the filtrate concentrated to an oil in vacuo. The dark brown oil was purified through a short flash silica column using 2:1 hexane/ethyl acetate as eluent to yield 1.471 g (74%) of a white solid. The product can be recrystallized from hexane/ethyl acetate.

NMR: ($CDCl_3$) 1.46,d,1H; 2.21,m, 1H; 3.90,s,3H; 3.97, m,2H; 4.00,s,3H; 4.26,dd,2H; 5.43,s,1H7.25,brs,2H. M.S. (CI) 250 (100%). Melting point 76.5°–77.5° C. Anal. calcd. for $C_{13}H_{15}O_4N$: C, 62.64: H, 6.06; N,5.62. Found: C, 62.45; H,6.02; N, 5.59.

Step B Preparation of 2-(5-aminomethyl-3,4-dimethoxyphenyl)-1,3-dioxolane (51) (FIG. 22)

2-(5-cyano-3,4-dimethoxyphenyl)-1,3-dioxolane (50) (FIG. 22) (0.555 g, 2.23 mmole) was predissolved in 2 ml dry THF and 10 ml anhydrous diethyl ether. To this solution under an argon atmosphere at room temperature was added 2.23 ml of 1.0M lithium aluminum hydride in diethyl ether solution. The reaction was then stirred at room temperature for 4 hours. The reaction was then cooled to 0° C. and the excess hydride destroyed with $H_2O$. The reaction mixture was subsequently quenched with 10% NaOH and extracted with diethyl ether. The organic layer was dried over $MgSO_4$, and concentrated to an oil in vacuo.

NMR: ($CDCl_3$) 1.47,d, 1H; 2.18,m,1H; 3.77,bd,2H; 3.79, s,3H; 3.85,s,3H; 3.94,dt,2H; 4.21,dd,2H; 5.40,s,1H; 6.95,bs, 2H.

Step C Preparation of N'-hydroxyl-N'-methyl-N-[2,3-dimethoxy-5-formylbenzyl urea (55)

2-(5-aminomethyl-3,4-dimethoxyphenyl)-1,3-dioxolane (51) isolated from the reduction 2-(5-cyano-3,4-dimethoxyphenyl)-1,3-dioxolane 50 (0.400 g, 2.23 mmole) as in step B was dissolved in 10 ml dichloromethane and triethylamine (202 mg). To this solution was added triphosgene (190 mg, 0.642 mmole) and the reaction was refluxed under nitrogen overnight. The reaction was cooled to room temperature and methyl hydroxylamine hydrochloride (403 mg, 4.83 mmole) predissolved in THF (10 ml), $H_2O$ (1 ml)

and triethylamine (488 mg) was added. The reaction was stirred at room temperature for two hours and was then quenched and extracted with 10 ml 5% HCl. The organic layer was separated and then stirred vigorously overnight over an equivolume of 10% HCl. The organic layer was separated, dried over $MgSO_4$, and concentrated to a brown oil in vacuo which was purified by flash column chromatograpy using 1:1 hexane/ethyl acetate-100% NMR: ($CHCl_3$) 3.15,s,3H; 3.91.s,3H; 3.96,s,3H; 4.45,s,2H; 6.41,br s,1H; 7.36,d,1H; 7.41,d,1H; 9.83,s,1H. M.S. (CI): 537, 269, 99 (100%)

Step D: Preparation of N'-hydroxyl-N'-methyl-N-[2,3-dimethoxy-5-[3-(3,4,5-trimethoxyphenyl)-2,4-dithiolanyl)] benzyl urea (29):

2-(5-aminomethyl-3,4-dimethoxyphenyl)-1,3-dioxolane (55) can be cyclized using the standard procedure illustrated in FIG. 1 to form dithiolane 29.

EXAMPLE 40

Preparation of 2-(3,4-dimethoxy-5-methyl-N,N-dimethylaminophenyl)-4-(3,4,5-trimethoxyphenyl)-1,3-dithiolane (30) (table 1)

2-(5-aminomethyl-3,4-dimethoxyphenyl)-1,3-dioxolane (51) (FIG. 22) can be reductively methylated following the procedure given in example 15, the acetal hydrolyzed following the procedure given in example 28,step C, and the resulting aldehyde cyclized using the standard procedure illustrated in FIG. 19 to form diothiolane (30) (Table 1).

EXAMPLE 41

Preparation of trans-2-[{2,6-dimethoxy-4-(3-(3,4,5-trimethoxyphenyl)-2,4-dithiolanyl) phenoxy}ethoxycarbonylaminomethyl]pyridine (31) (FIG. 26)

Trans-2-(3,5-dimethoxy-4-(2'-hydroxyethoxyphenyl))-4-(3,4,5-trimethoxyphenyl)-1,3-dithiolane (27) (FIG. 26) (0.395 g,0.844 mmole) was dissolved in 25 ml dry chloroform and 136 µl of pyridine was added. The reaction was cooled to 0° C. under an argon atmosphere and 116 µl of chlorophenylcarbonate was added. The reaction was allowed to warm to room temperature and was stirred for 2 hours. The reaction was quenched with 5% HCl and extracted with chloroform. The organic layer was dried over $MgSO_4$ and concentrated to 25 ml total volume. 2-(aminomethyl)pyridine (108 ml, 1.05 mmole) was added and the reaction was refluxed under an argon atmosphere for 12 hours. The reaction was concentrated to 1 ml total volume and purified by flash column chromatography using 1/1 hexane/ethyl acetate–100% ethyl acetate as eluent. The column yields 365 mg (72%) as a white foam.

Trans epimer:

NMR: ($CDCl_3$) 3.46,dd,1H; 3.64,dd,1H; 3.81,s,6H; 3.84, s,3H; 3.88,s,6H; 4.16,t,2H; 4.45,t,2H; 4.62,d,2H; 5.05,dd, 1H; 5.07,s,2H; 5.82,s,1H; 6.72,s,2H; 6.81,s,2H; 7.15,m,2H; 7.61,t,1H; 8.50,d,1H. M.S. (CI): 603 (100%) 195.

EXAMPLE 42

Preparation of trans-2-[N-acetyl[{2,6-dimethoxy-4-(3-(3,4,5-trimethoxyphenyl)-2,4-dithiolanyl) phenoxy}ethoxycarbonyl]aminomethyl]pyridine (32) (FIG. 26)

Trans-2-[{2,6-dimethoxy-4-(3-(3,4,5-trimethoxyphenyl)-2,4-dithiolanyl)phenoxy}ethoxycarbonylaminomethyl] pyridine (31) (FIG. 26) (0.313 g,0.520 mmole) was dissolved in 20 ml dry dichloromethane. The reaction was cooled to 0° C. under an argon atmosphere and 44 µl of acetyl chloride was added. The reaction was allowed to warm to room temperature and was stirred overnight. The reaction was recooled to 0° C. and 87 µl triethyl amine and 44 µl acetyl chloride was added. The reaction was then allowed to warm to room temperature and was stirred for an additional 12 hours. The reaction was then quenched with 10% $NaHCO_3$ and extracted with dichloromethane. The organic layer was dried over $MgSO_4$ and concentrated to a brown oil which was purified by flash column chromatography using 1:1 hexane/ethyl acetate—1:2 hexane/ethyl acetate as eluent. The column yields 293 mg (88%) as a white foam.

Trans epimer:

NMR: ($CDCl_3$) 2.63,s,3H; 3.47,dd,1H; 3.48,dd.1H; 3.64, dd,1H; 3.84,s,6H; 3.86,s,3H; 3.88,s,6H; 4.18,t,2H; 4.35,t, 2H; 4.62,d,2H; 5.05,dd,1H; 5.81,s,1H; 6.72,s,2H; 6.81,s,2H; 7.38,t,1H; 7.51,d,1H; 7.88,t,1H; 8.56,d,1H. M.S. (CI): 644, 403, 195, 133, 84 (100%).

EXAMPLE 43

Preparation of trans-2-[N-acetyl[{2,6-dimethoxy-4-(3-(3,4,5-trimethoxyphenyl)-2,4-dithiolanyl) phenoxy}ethoxycarbonyl]aminomethyl]-1-ethyl pyridinium triflate (33) (FIG. 26)

2-[-N-acetyl[{2,6-dimethoxy-4-(3-(3,4,5-trimethoxyphenyl)-2,4-dithiolanyl) phenoxy}ethoxycarbonyl]aminomethyl]pyridine (32) (FIG. 26) (0.049 g, 0.076 mmole), diisopropylethylamine (8 µl, 0.076 mmole) and 5 ml anhydrous dichloromethane were cooled to 0° C. under a nitrogen atmosphere. Ethyl triflate (10 µl, 0.076 mmole) was added. The reaction was allowed to warm to room temperature and was stirred for 12 hours. The solvent was removed in vacuo and the remaining residue redissolved in 0.5 ml acetone. The acetone solution was purified by flash column chromatography using 100% ethyl acetate-10/1$CHCl_3$ MeOH-4/1$CHCl_3$/MeOH as eluent. The product was isolated as a 1.6/1.0 trans/cis mixture of diastereomers as a white foam (0.047 g. 75%).

Cis/trans epimers:

NMR: (Acetone-$D_6$) 1.72,t,6H; 2.64,s,6H; 3.51–3.7,m, 4H; 3.79,brs,12H; 3.80,brs,18H; 4.12,m,4H; 4.45,m,4H; 4.96,m,7H; 5.17,dd,1H; 5.53,brs,4H; 5.79,s,1H; 5.92,s,1H; 6.86,s,2H; 6.90,s,2H; 6.94,s,2H; 6.97,s,2H; 8.08,brd,4H; 8.56,t,2H; 9.12,brd,2H.

EXAMPLE 44

Figure 27:
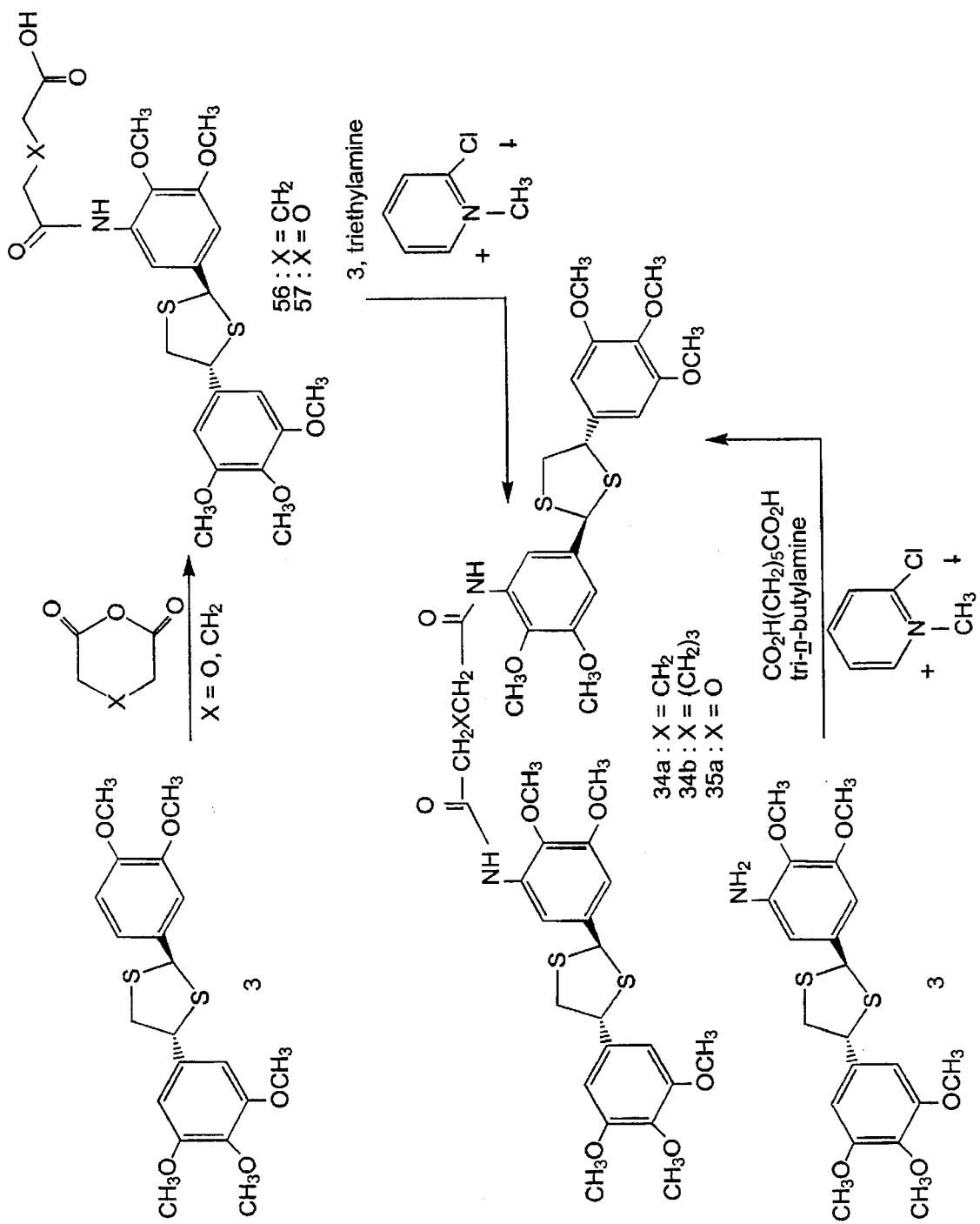
FIGS. 27 & 28 are schematic drawings showing the general synthetic approach form producing dimeric 2,4-diaryl-1,3-dithiolane compounds with an amide linkage.

Trans-bis-glutaric-amide dithiolane dimer (34a) and trans-bis-pimelic-amide dithiolane dimer (34b) (see Table 3 and FIG. 27).

Step A Preparation of trans-glutaric amide/acid dithiolane (56) (FIG. 27)

Trans-2-(5-amino-3,4-dimethoxyphenyl)-4-(3,4,5-trimethoxyphenyl)-1,3-dithiolane (3) (FIG. 27) (0.100 g,0.236 mmole) was predissolved in 10 ml dry dichloromethane and was cooled to 0° C. under an argon atmosphere. To this solution was added 35 mg of diglutaric anhydride (0.035, 0.306 mmole), and 1 drop of glacial acetic acid. The reaction was allowed to warm to room temperature and was stirred overnight. The solvent was removed in vacuo and the remaining residue purified by flash column chromatography using chloroform—2:1 chloroform/methanol as eluent. The column yields 106 mg (84%) of a pale red foam.

Trans epimer:

NMR: (CDCl$_3$) 2.08,t,2H; 2.52,t,4H; 3.45,dd,1H; 3.65, dd,1H; 3.83,s,3H; 3.87,s,3H; 3.88,s,6H.; 3.90,s,3H; 5.08,dd, 1H; 5.81,s,1H; 6.72,s,2H; 6.95,d,1H; 7.86,s,1H; 8.26,s,1H. M.S. (CI): 538, 89 (100%).

Step B Preparation of trans-bis-glutaric-amide dithiolane dimer (34a) (FIG. 27)

Compound (56) (FIG. 27) (0.038 g, 0.071 mmole), trans-2-(5-amino-3,4-dimethoxyphenyl)-4-(3,4,5-trimethoxyphenyl)-1,3-dithiolane (3) (FIG. 27) (0.032 g,0.076 mmole), 2-chloro-1-methylpyridinium iodide (0.022 g, 0.085 mmole), triethylamine (0.014 g, 0.014 mmole) and dry dichloromethane (5 ml) were refluxed under an argon atmosphere overnight. The reaction was quenched with 5% HCl and the product extracted into dichloromethane. The organic layer was dried over magnesium sulfate and concentrated in vacuo to an oil which was purified by flash column chromatography using 1:1 hexane/ethyl acetate—100% ethyl acetate as eluent. The column yields 18 mg (27%) of a clear oil.

Trans epimer:

NMR: (CDCl$_3$) 2.09,m,2H; 2.80,t,4H; 3.43,dd,2H; 3.60, dd,2H; 3.76,s,6H; 3.82,s,6H; 3.86,s,12H; 3.90,s,6H; 4.97, dd,2H; 5.78,s,2H; 6.70,s,4H; 6.88,d,2H; 7.72,d,2H.

Preparation of trans-bis-pimelic-amide dithiolane dimer (34b) (FIG. 27)

Pimelic acid (0.0095 g, 0.059 mmole), trans-2-(5-amino-3,4-dimethoxyphenyl)-4-(3,4,5-trimethoxyphenyl)-1,3-dithiolane (3) (FIG. 27) (0.05 g,0.118 mmole), 2-chloro-1-methylpyridinium iodide (0.036 g, 0.142 mmole), tri-n-butylamine (0.052 g, 0.284 mmole) and dry toluene (10 ml) were refluxed under an argon atmosphere for 5 hours. The solvent was removed in vacuo and the remaining residue was redissolved in chloroform. The solution was washed with 5% HCl and H$_2$O, dried over magnesium sulfate and concentrated in vacuo to an oil which was purified by flash column chromatography using 1:1 hexane/ethyl acetate-1:2 hexane/ethyl acetate as eluent. The column yields 26 mg (46%) of a clear oil.

Trans epimer:

NMR: (CDCl$_3$) 1.49,m,2H; 1.79,m,4H; 2.42,t,4H; 3.43, dd,2H; 3.65,dd,2H; 3.83,s,6H; 3.86,s,6H;. 3.87,s,12H; 3.90, s,6H; 5.07,dd,2H; 5.81,s,2H; 6.72,s,4H; 6.94,d,2H; 7.79,d, 2H; 8.27,s,2H.

Following substantially the same procedure as described for compound 34b (FIG. 29), dimer 34c (FIG. 29) can be prepared.

EXAMPLE 45

Figure 28:
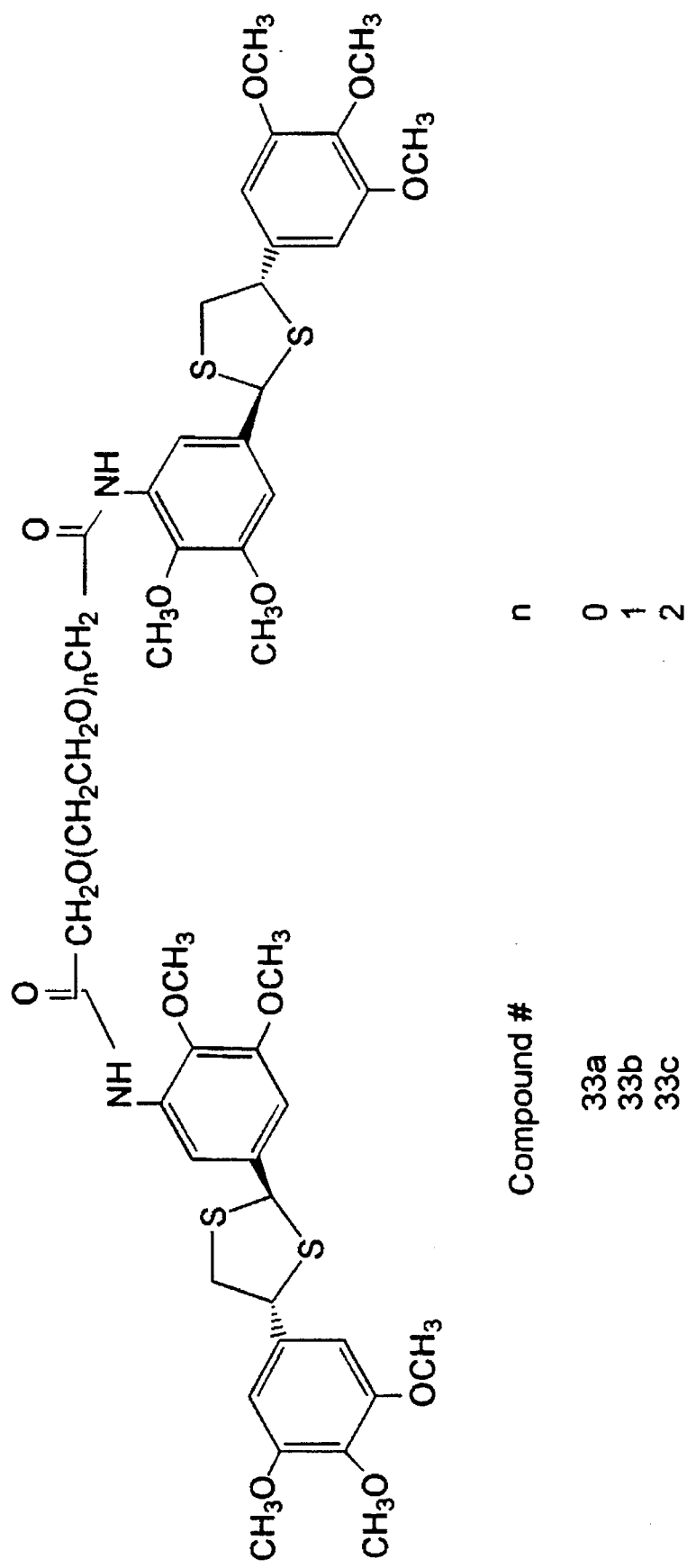

Trans-bis-glycolic-amide dithiolane dimer (35a) (See FIGS. 27 and 28)

Step A Preparation of trans-glycolic amid/acid dithiolane (57) (FIG. 27)

Trans-2-(5-amino-3,4-dimethoxyphenyl)-4-(3,4,5-trimethoxyphenyl)-1,3-dithiolane (3) (FIG. 27) (0.100 g,0.236 mmole) was predissolved in 10 ml dry dichloromethane and was cooled to 0° C. under an argon atmosphere. To this solution was added 36 mg of 90% diglycolic anhydride (0.036, 0.283 mmole). The reaction was allowed to warm to room temperature and was stirred for 12 hours. The solvent was removed in vacuo and the remaining residue purified by flash column chromatography using chloroform—3:1 chloroform/methanol as eluent. The column yields 126 mg (99%) of a pale red foam. The product will crystallize to a white solid from hexane/ethyl acetate.

Trans epimer:

NMR: (CDCl$_3$) 3.45,dd,1H; 3.63,dd,1H; 3.83,s,3H; 3.86, s,3H; 3.87,s,6H; 3.90,s,3H; 4.23,s,2H; 4.28.s,2H; 5.07,dd, 1H; 5.65,bs,1H; 5.82,s,1H; 6.72,s,2H; 7.00,d,1H; 8.22.s,1H; 9.08,s,1H. M.S. (CI): 539, 117 (100%).

Step B Preparation of trans-bis-glycolic-amide dithiolane dimer (35a) (FIG. 27)

Compound (57) (0.126 g, 0.234 mmole), Trans-2-(5-amino-3,4-dimethoxyphenyl)-4-(3,4,5-trimethoxyphenyl)-1,3-dithiolane (3) (FIG. 27) (0.099 g,0.234 mmole), 2-chloro-1-methylpyridinium iodide (0.072 g, 0.281 mmole), triethylamine (0.028 g, 0.281 mmole) and dry dichloromethane (10 ml) were refluxed under an argon atmosphere for 15 hours. The reaction was quenched with 5% HCl and the product extracted into dichloromethane. The organic layer was dried over magnesium sulfate and concentrated in vacuo to an oil which was purified by flash column chromatography using 1:1 hexane/ethyl acetate-100% ethyl acetate as eluent. The column yields 101 mg (46%) of a clear oil which crystallized from ethyl acetate/hexane.

Trans epimer:

NMR: (CDCl$_3$) 3.46,dd,2H; 3.65,dd,2H; 3.84,s,6H; 3.86, s,6H; 3.88,s,12H; 3.91,s,6H; 4.28,s,4H; 5.08,dd,1H; 5.83,s, 2H; 6.72,s,4H; 7.01,d,2H; 8.26,d,2H; 8.85,bs,2H. M.S. (IBu): 945, 195 (100%).

Following substantially the same procedure as described for compound 34, dimers 35b and 35c can be prepared.

EXAMPLE 46

Figure 29:
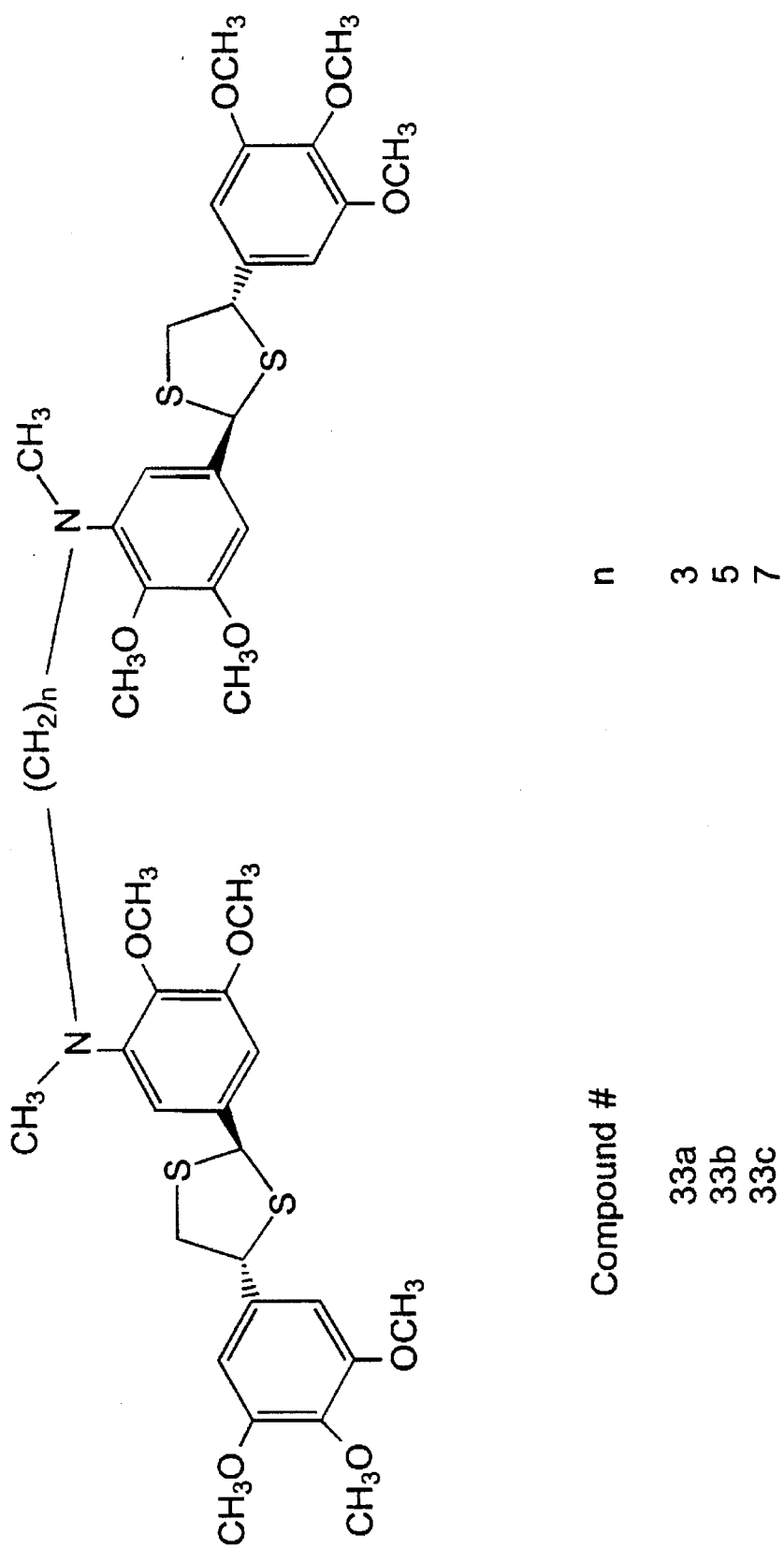
FIG. 29 is a schematic drawing producing the general synthetic approach for producing dimeric 2,4-diaryl-1,3-dithiolane compounds with an amine linkage.

Trans-bis-alkyl-amine dithiolane dimers (36a,b,c) (See FIG. 29)

Dimers of type 36a, b, and c (FIG. 29) can be readily synthesized starting with trans-2-(3,4-dimethoxy-5-methylaminophenyl)-4-(3,4,5-trimethoxyphenyl)-1,3-dithiolane (4) ( table 1). and alkyl dihalides or p-ditosylates such as the commercially available 1,3-propanediol-p-ditosylate, using conditions as reported by Erez et al., in J. Med. Chem., 25, 847–849 (1982).

EXAMPLE 47

2-(3,5-dimethoxy-4-hydroxyphenyl)-4-(3,4,5-trimethoxyphenyl)-1,3-dithiolane tetraethyleneglycol dimer (Compound 22a)

Tetraethyleneglycol-1,10-diiodide (0.125 g, 0.302 mmole), 2-(3,5-dimethoxy-4-hydroxyphenyl)-4-(3,4,5-trimethoxyphenyl)-1,3-dithiolane (compound 5 on FIG. 2) (0.270 g, 0.637 mmole), potassium tert-butoxide (0.071 g, 0.637 mmole) and 5 ml dry THF are stirred at room temperature for 24 hours. Dry DMF (1 ml) is added and the reaction is stirred for an additional 12 hours. The solvent is removed in vacuo and the remaining oil is purified to a white foam by flash column chromatography using 2:1–1:2 hex/ethyl acetate as eluent (0.174 g). C,H Analysis: C (57.24, 57.21), H (6.20,6.17). Following substantially the same procedures, the other dimeric 2,4-diaryl-1,3-dithiolane compounds (i.e., compounds 22B–G) reported in FIGS. 6a and 6b are prepared.

Figure 7:
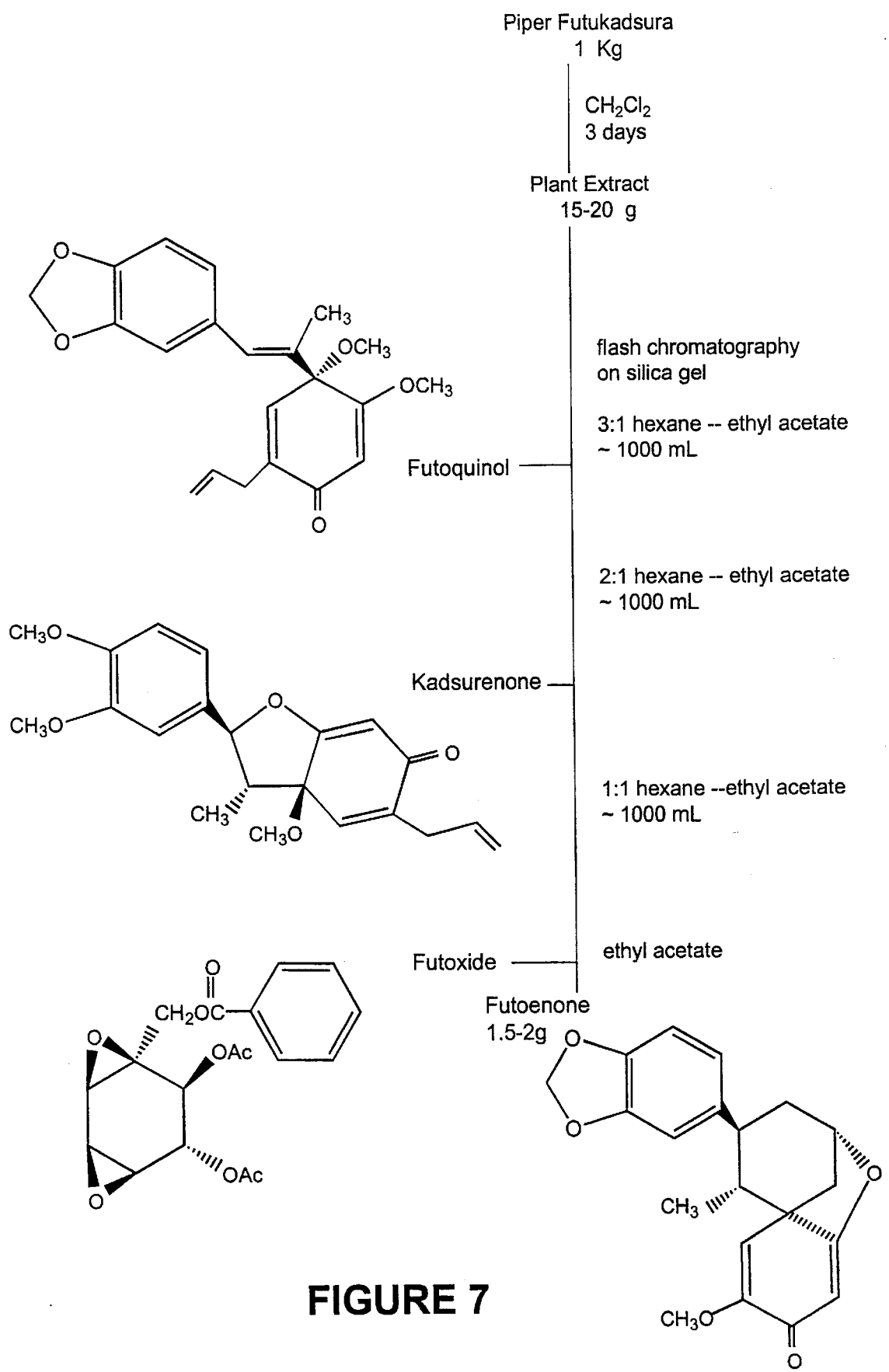
FIG. 7 is a schematic drawing showing the extraction of futoenone and other compounds from Piper fotukadsura.

As discussed above, another series of neolignan derivatives which are potent PAF antagonist compounds can be isolated from the leaves of the Piper futokadsura (Chinese herbal plant). FIG. 7 shows sevaral compounds compounds isolated from Piper futokadsura via extraction. In particular, the plant material is soaked for three days in dicloromethane then filtered using a Buchner funnel and water aspiration. The resulting filtrate is concentrated in vacuo and futoquinol, kadsurenone, futoxide, and futoenone are separated by flash chromotography on silica gel using a gradient of hexane and ethyl acetate. Shen et al. in *Proc. Natl. Acad. Sci.* (U.S.A.), 82. 672–678 (1985), reported that kadsurenone is a potent, specific and competitive inhibitor of PAF an the receptor level. A part of this invention is particularly concerned with futoenone and derivatives thereof. Futoenone is a major component of Piper futokadsura, constituting 0.1% dry weight of the plant. While the structure and several syntheses of futoenone have previously been published (see, Ogiso et al., *Tet. lett.*, 16, 2003 (1968) and Ogiso et al., *Chem. Pharm. Bull.*, 18, 1005 (1970)), the inventors are the first to observe that futoenone posesses PAF antagonist activity. Using the procedures described above for the human platelet assay in PRP, futoenone was found to have an $IC_{50}$ value of approximately 13.6 µM for platelet aggregation induced by 0.1 µM PAF (see FIG. 14b where X=O and $R_1,R_2$=a single —$CH_2$— which closes the ring between the oxygens).

Figure 8A:
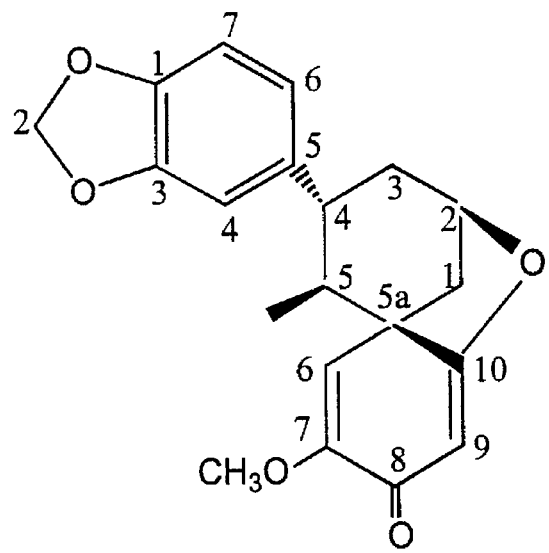
FIGS. 8a and 8b are chemical structures of futoenone and a futoenone derivative, respectively, showing the numbering scheme used to identify the novel compounds of this invention.
Figure 8B:
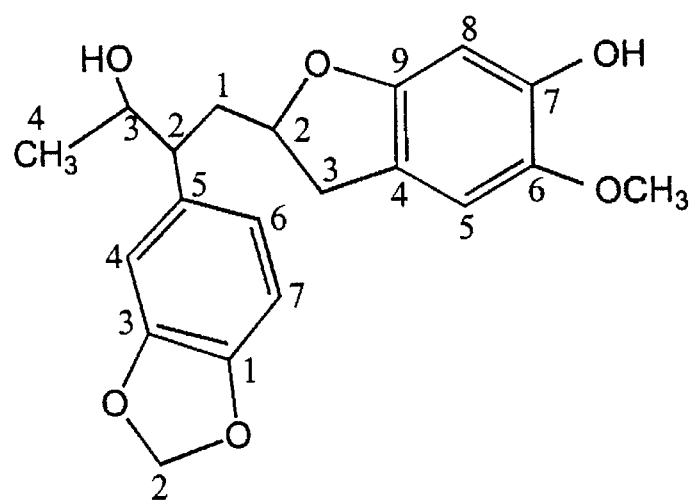

Many futoenone derivative compounds have been prepared and the PAF and 5-lipoxygenase activity for several of the compounds have been determined. FIGS. 8a and 8b show the numbering scheme used to identify these new compounds and FIGS. 9–13 schematically show the synthetic routes used to prepare the new compounds. The following Examples relate particularly to FIGS. 9–13 where the compound number used in an Example relates to the number identified in FIGS. 9–13.

EXAMPLE 48

Figure 9:
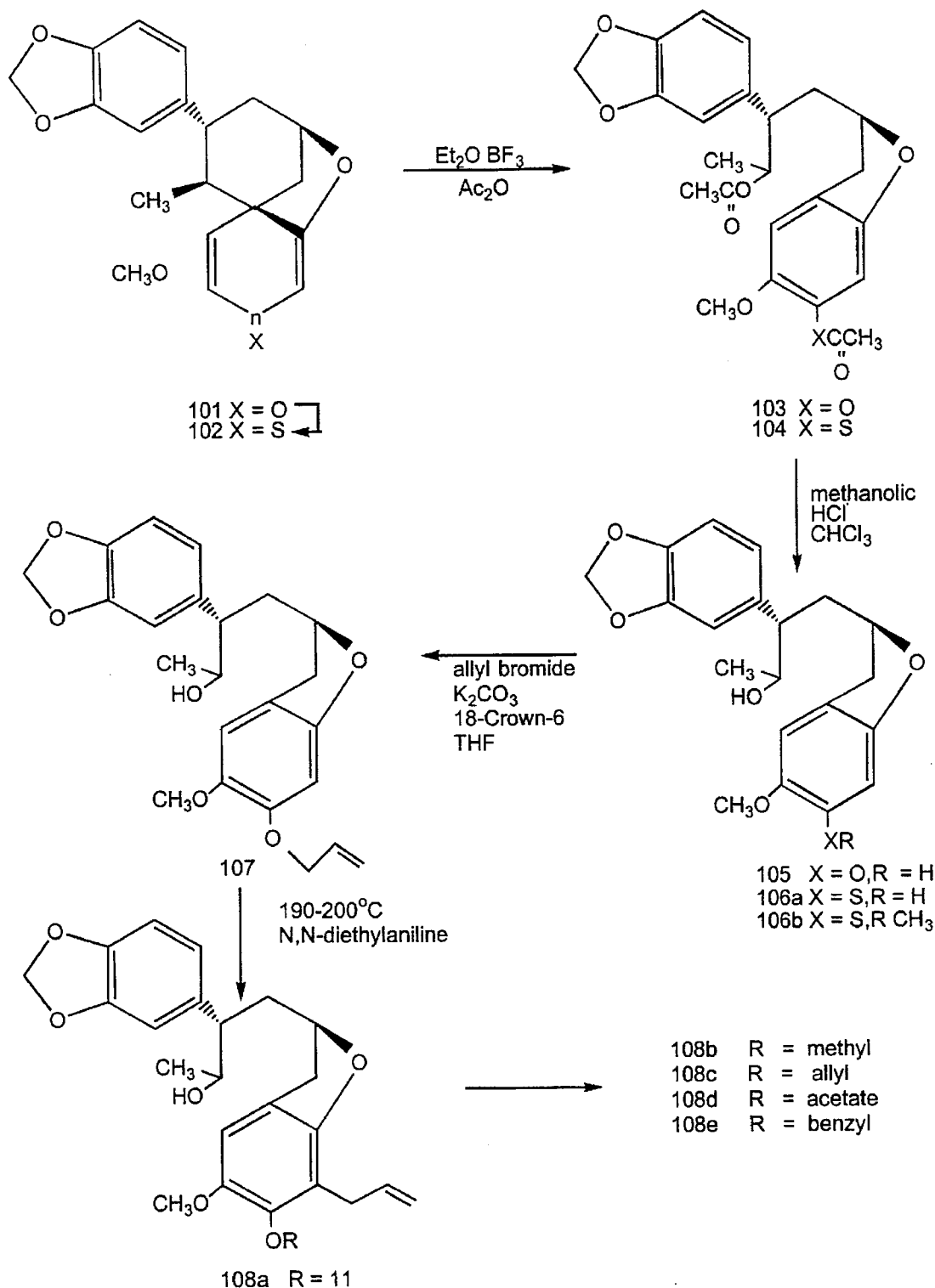
FIGS. 9–13 are schematic drawings showing the synthesis of futoenone derivative compounds.

2-[3-acetyl-2-(1,3-benzodioxol-5-yl)butane]-7-acetyl-6-methoxydihydrobenzofuran (103, FIG. 9)

Boron trifluoride etherate (0.231 ml, 0.0014 mols) is added to a stirred solution of futoenone (101) (1.0 g, 0.0029 mols) in acetic anhydride (16.76 ml). The reaction is monitored with thin layer chromatography (TLC) until no starting material is observed. This involves stirring at room temperature for nine hours then gently warming for 30 minutes. The color changes from yellow to orange over the course of the reaction. The reaction mixture is poured over ice-water and extracted with ether. The ether extract is washed with sodium bicarbonate followed by water and dried over magnesium sulfate. The extract is filtered and dried in vacuo. The reaction mixture is purified by flash chromatography on a silica gel (4.0 g with 5:1 hexane-ethyl acetate as the eluant). The fractions corresponding to the product, as determined by $^1$H NMR spectra are combined and concentrated in vacuo affording a bright yellow foam; 0.87 mg (66%).

$^1$H NMR ppm: 1.05 (3H, d), 1.76 (1H, m), 2.06 (3H, s) 2.23 (1H, m), 2.28 (3H, s), 2.71 (1H,d) 2.98 (1H, m) 3.07 (1H, dd), 3.74 (3H, s), 4.43 (1H, m), 5.02 (1H, m), 5.94 (2H, s), 6.47 (1H, s), 6.72 (4H, m). M+(CI)=442 (Mass Spec. parent ion peak).

EXAMPLE 49

2-[3-hydroxy-2-(1,3-benzodioxol-5-yl)butane]-7-hydroxy-6-methoxydihydrobenzofuran (105, FIG. 9)

Acetyl chloride (0.77 ml, 1.08 mmoles) in methanol (methanolic HCl prepared by addition of acetyl chloride to dry methanol at 0° C.) is added to a stirred solution of 2-[3-acetyl-2-(1,3-benzodioxol-5-yl)butane]-7-acetyl-6-methoxydihydrofuran (103, prepared as described in Example 48) (1.45 g, 3.3 mmoles) in chloroform (5 ml, 6.2 mmoles). The reaction turns orange-red with the addition of methanolic HCl. The reaction is stirred at room temperature for six hours and is monitored by TLC every hour. The reaction mixture is treated with sodium bicarbonate, diluted with 30 ml of chloroform, and washed with water. The extract is dried over sodium sulfate, filtered, and concentrated in vacuo. The extract shows three spots on TLC (1:1 hexane-ethyl acetate) with the product being the most polar of the three. The reaction is purified by flash chromatography on silica gel (1:1:2 hexane-ether-dichloromethane as the eluant). The fractions corresponding to the product are combined and concentrated (0.84 g, 2.4×10–3 mmoles,71%) and resemble a pale yellow foam.

Anal. Calcd. for $C_{20}H_{22}O_6$: C, 67.03; H, 6.19. Found: C, 66.88; H, 6.26 (Analytic data C=carbon, H=hydrogen). $^1$H NMR ppm: 1.07 (3H, d), 1.92 (1H, m), 2.4 (1H, m), 2.68 (1H, dd), 2.84 (1H, m), 3.07 (1H, dd), 3.78 (3H, s), 3.93 (1H, m), 4.5 (1H, m), 5.5 (1H, s), 5.95 (2H, s), 6.4 (1H, s), 6.63 (4H, m). M+(CI)=358.

EXAMPLE 50

2-[3-hydroxy-2-(1,3-benzodioxol-5-yl)butane]-7-allyloxy-6-methoxydihydrobenzofuran (107, FIG. 9)

Potassium carbonate (0.97 g, 7.02 mmoles), 18-Crown-6 ether (0.25 g, 9.45 mmoles) and allyl bromide (0.32 Ml, 3.7 mmoles) are added to a stirred solution of 2-[3-hydroxy-2-(1,3-benzodioxol-5-yl)butane]-7-hydroxy-6-methoxydihydrobenzofuran (105, prepared as described in Example 49) (0.84 g, 2.35 mmoles) in THF (12 ml). The reaction is stirred for one hour and is monitored by TLC. After four hours, allyl bromide (0.5 eq) is added to drive the reaction to completion. The reaction is stirred for an additional two hours with no change. Another 0.5 eq of allyl bromide is then added to reaction. After stirring a total of 6.5 hours, the reaction was warmed for 0.5 h. The reaction mixture is poured over ice-water, extracted with methylene chloride, and the extract is dried with sodium sulfate. The reaction mixture is purified by flash chromatography on a silica gel (150 g with 1:1:1 hexane-diethyl ether-dichloromethane as the eluant). The fractions identified by TLC corresponding to the allyl ether are combined, and concentrated in vacuo producing a foam, 0.76 g (1.91×10–3 mmoles 82%). $^1$H NMR ppm: 1.07 (3H ,d), 1.85 (1H, m), 2.41 (1H, m), 2.72 (1H, m), 3.09 (1H, dd), 3.78 (3H, s), 3.85 (1H, m), 4.32 (1H, m), 4.55 (2H, d), 5.34 (2H, dd), 5.94 (2H, s), 6.04 (1H, m), 6.4 (1H, s), 6.72 (4H, m). M+(CI)=398.

EXAMPLE 51

2-[3-hydroxy-2-(1,3-benzodioxol-5-yl) butane]-8-allyl-7-hydroxy-6-methoxydihydrobenzofuran (108a, FIG. 9)

N,N-diethylaniline (2.5 ml) is added to 0.8 g of 2-[3-hydroxy-2-(1,3-benzodioxol-5-yl)butane]-7-allyloxy-6-methoxydihydrobenzofuran (107, prepared according to Example 50). The stirred solution is placed in an oil bath and heated at 190°–200° C. for three hours. The reaction is diluted with ether and washed with 10% HCl followed by water. The ether extract is dried over sodium sulfate overnight. The extract is filtered and concentrated in vacuo. The reaction is purified by flash chromatography on silica gel (8.0 g with 1:1:1 hexane-diethyl ether-dichloromethane) to produce 0.043 g (40%) 2-[3-hydroxy-2-(1,3-benzodioxol-5-yl)butane]-8-allyl-7-hydroxy-6-methoxydihydrobenzofuran (108a).

¹H NMR ppm: 1.05 (3H, d), 1.82 (1H, m), 2.69 (1H, dd), 2.85 (1H, m), 3.05 (1H, dd), 3.36 (2H, d), 3.79 (3H, s), 3.86 (1H, m), 4.53 (1H, m), 5.04 (21H, dd), 5.61 (1H, s), 5.95 (2H, s), 6.01 (1H, m) 6.57 (1H, s), 6.73 (3H, m).

EXAMPLE 52

2-[3-hydroxy-2-(1,3-benzodioxol-5-yl)butane]-8-allyl-6,7-dimethoxydihydrobenzofuran (108b, FIG. 9)

Potassium carbonate (8.7 mg, 0.063 mmoles), 18-crown-6 ether (6.7 mg, 0.025 mmoles), and iodomethane (3.92 ml, mmoles) is added to a stirred solution of 2-[3-hydroxy-2-(1,3-benzodioxol-5-yl)butane]-8-allyl-7-hydroxy-6-methoxydihydrobenzofuran (108a, prepared according to Example 51) in THF (1 ml). The reaction is stirred at 0° C. for one hour and then is gradually warmed to room temperature. The reaction is monitored by TLC until little starting material remains (approximately five hours elapsed time). The reaction mixture is poured over ice-water, extracted with dichloromethane, and washed with 10% HCl followed by water. The extracts are dried over sodium sulfate and concentrated in vacuo. The reaction mixture is purified by flash chromatography on silica gel (2.5 g with 2:1 hexane-ethyl acetate as the eluant) to obtain 14.2 mg (53% yield) of 2-[3-hydroxy-2-(1,3-benzodioxol-5-yl) butane]-8-allyl-6,7-dimethoxydihydrobenzofuran (108b). The product and starting material run very close together on silica so separation is difficult and several fractions may contain a mixture of methyl ether and starting material. M+(CI)=413 ¹H NMR ppm: 1.06 (3H, D), 1.82 (1H, m), 2.69 (1H, dd), 2.85 (1H, m), 3.13 (1H, dd), 3.36 (2H, d), 3.79 (6H, s), 3.86 (1H, m), 4.53 (1H, m), 5.04 (2H, dd), 5.61 (1H, s), 5.95 (2H, s), 6.01 (1H, m), 6.57 (1H, s), 6.73 (3H, m).

EXAMPLE 53

Following substantially the same procedure as described in Example 52,the following related compounds can be prepared:

2-[3-hydroxy-2-(1,3-benzodioxol-5-yl)butane]-8-allyl-7-allyloxy-6-methoxydihydrobenzofuran (108c, FIG. 9)

M+(CI)=440 ¹H NMR ppm: 1.06 (3H, d), 1.82 (1H, m), 2.69 (1H, dd), 2.85 (1H, m), 3.13 (1H, dd), 3.23 (2H, d), 3.79 (3H, s), 3.86 (1H, m), 4.53 (1H, m), 5.04 (2H, dd), 5.95 (2H, s), 6.73 (4H, m).

2-[3-hydroxy-2-(1,3-benzodioxol-5-yl)butane]-7-acetyl-8-allyl-6-methoxydihydrobenzofuran (108d, FIG. 9)

M+(CI)=439 ¹H NMR ppm: 1.06 (3H, d), 1.82 (3H, s), 2.69 (1H, dd), 2.85 (1H, m), 3.13 (1H, dd), 3.36 (2H, d), 3.79 (3H, s), 4.42 (2H, d), 4.50 (1H, m), 5.04 (2H, dd), 5.30 (2H, dd), 5.95 (2H, dd), 6.09 (2H, m), 6.61 (1H, s), 6.73 (3H, m).

2-[3-hydroxy-2-(1,3-benzodioxol-5-yl)butane]-8-allyl-7-benzyloxy-6-methoxydihydrobenzofuran (108e, FIG. 9)

M+(CI)=489 ¹H NMR ppm: 1.06 (3H, d), 1.82 (1H, m), 2.69 (1H, dd), 2.85 (1H, m), 3.13 (1H, dd), 3.36 (2H, d), 3.79 (3H, s), 3.86 (1H, m), 4.53 (1H, m), 4.95 (2H, d), 4.98 (2H, dd), 6.70 (4H, m), 7.24 (1H, s), 7.4 (2H, m), 7.55 (2H, d).

EXAMPLE 54

Figure 10:
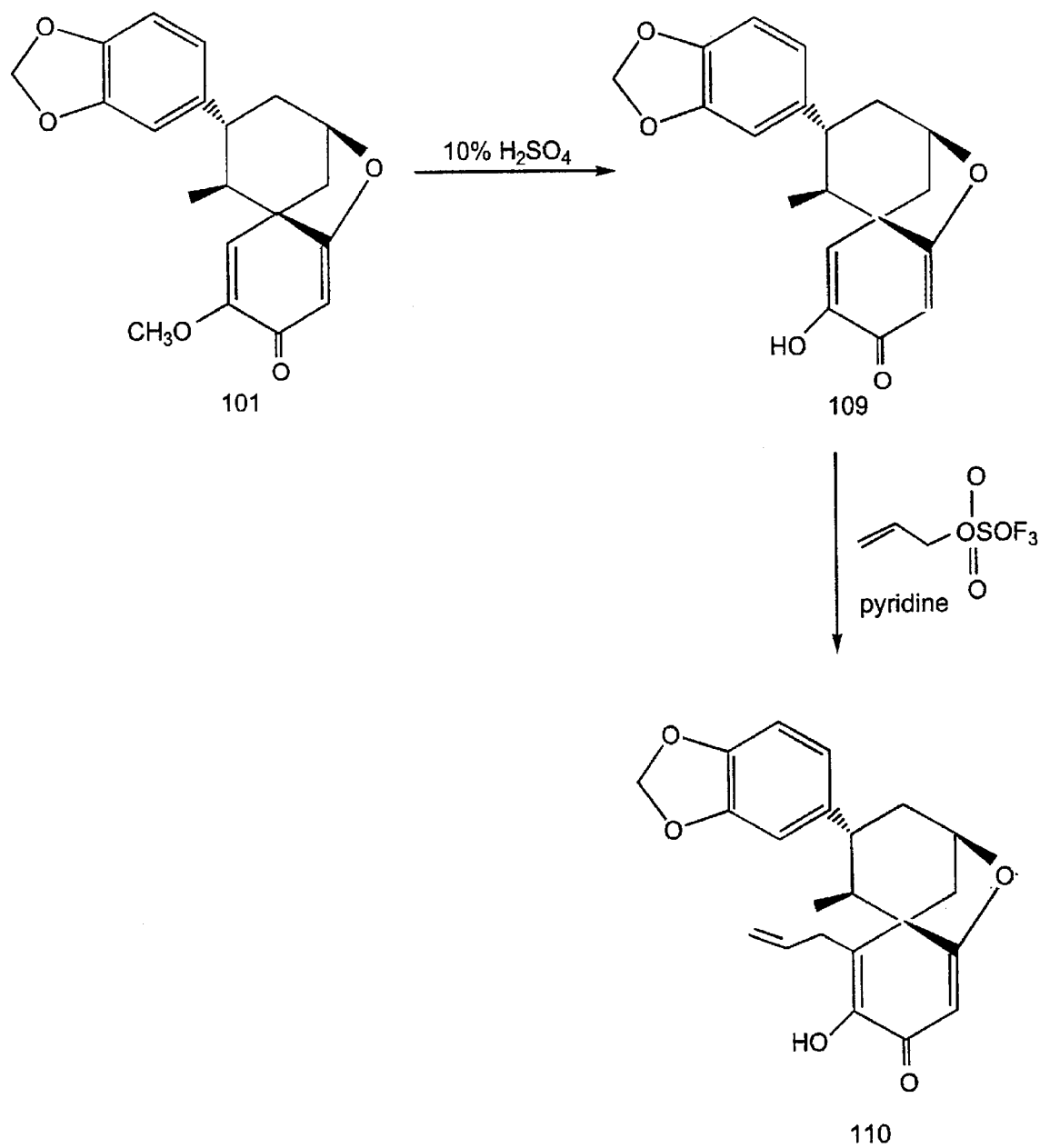

4-(1,3-benzodioxol-5-yl )-2,3,4,5-tetrahydro-7-hydroxy-5-methyl-8H-2,5a-methano-1-benzoxepin-8-one (109, FIG. 10)

Futoenone (50 mg, 0.15 mmol) and 30% sulfuric acid (7.5 ml) are added to a 25 ml round bottom flask. This mixture is heated with a heating mantle to reflux for approximately six hours. The reaction mixture is diluted with distilled water and crystals begin to precipitate. The flask is placed in a refrigerator to aid in precipitation. The crystals are collected by filtration, 300 mg (80%). M+(CI)=327. ¹H NMR ppm: 0.59 (3H, d), 1.25 (1H, s), 1.72 (1H, t), 2.03 (1H, m), 2.17 (1h, d), 2.35 (2H, m), 2.53 (1H, m), 5.06 (1H, t), 5.72 (1H, s), 5.83 (1H, s), 5.93 (2H, s), 6.69 (3H, m).

EXAMPLE 55

4-(1,3-benzodioxol-5-yl)-2,3,4,5-tetrahydro-6-allyl-7-hydroxy-5-methyl-8H-2,5a-methano-1-benzoxepin-8-one (110, FIG. 10)

Potassium carbonate (172.7 mg, 1.25 mmol) and mesyl allyl ether (113 mg, 0.83 mmol) are added to a stirred solution of 4-(1,3-benzodioxol-5-yl)- 2,3,4,5-tetrahydro-7-hydroxy-5-methyl-8H-2,5a-methano-1-benzoxepin-8-one (109, as prepared in Example 54) in DMF (4 ml). The reaction is stirred at room temperature overnight, after which time TLC still shows unreacted starting material present. An additional 50 µl mesyl allyl ether is then added to the reaction and the reaction is then starred for another 24 hours. The reaction is diluted with methylene chloride and washed with 10% HCl followed by water. The extract is dried over sodium sulfate and concentrated in vacuo. The reaction is best purified by medium pressure liquid chromatography (MPLC) (i.e., flash chromatography on silica gel (25 g, 1:1 hexane-ethyl acetate as eluant) produces a contaminated product as determined by ¹H NMR and flash chromatography on silica gel (30 g silica, 1:1:1 hexane-ethyl ether-methylene chloride) also produces a contaminated product as determined by ¹H NMR). M+(CI)=367. ¹H NMR: 0.64 (3H, d), 1.67 (1H, dd), 1.89 (1H, d), 2.06 (1H, m), 2.26 (2H, m), 2.49 (3H, m), 2.72 (1H, dd), 3.05 (1H, t), 5.08 (3H, m), 5.92 (2H, s), 6.15 (1H, s), 6.65 (3H, m).

EXAMPLE 56

Figure 11:
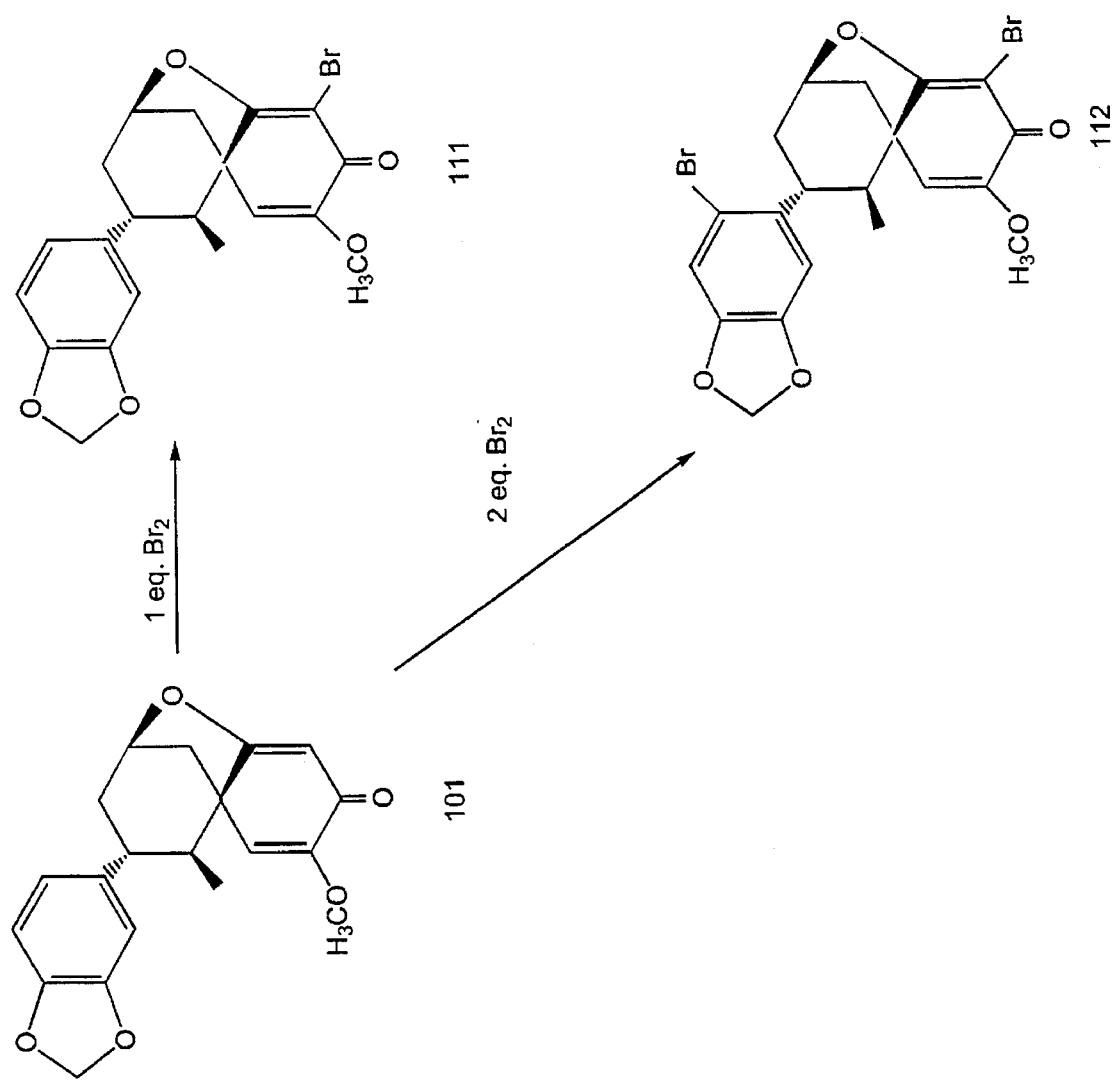

4-(1,3-benzodioxol-5-yl)-2,3,4,5-tetrahydro-7-methoxy-5-methyl-8H-2,5a-methano-9-bromo-1-benzoxepin-8-one (111, FIG. 11)

Pyridine (19.0 mg, 0.24 mmols) is added to a stirred solution of futoenone (101)(51 mg, 0.15 mmols) in 2 ml distilled dichloromethane, followed by the addition of a 0.1M solution of bromine (2 ml) at −60° to −78° C. under argon. The reaction is stirred overnight and slowly warmed up from −78 ° C. to room temperature. After 24 h, the reaction is concentrated in vacuo and purified by MPLC using ethyl acetate on silica gel. The major product identified by TLC is collected and concentrated in vacuo forming a white solid. The solid is recrystallized using ethyl acetate, 234.5 mg (95.2%). M+(CI)=419. ¹H NMR ppm: 0.55 (3H, d), 2.05 (1H, m), 2.43 (5H, m), 3.66 (3H, s), 5.19 (1H, t), 5.49 (1H, s), 5.92 (2H, s), 6.68 (3H, m).

EXAMPLE 57

Following substantially the same procedure as described in Example 20 (however, 2 equivalents of bromine are used), 4-(1,3-benzodioxol-6-bromo-5-yl)- 2,3,4,5-tetrahydro-7-methoxy-5-methyl-8H-2,5a-methano-9-bromo-1-benzoxepin-8-one (112, FIG. 11) is produced. ¹H NMR ppm: 0.566 (3H, d), 1.579 (1H, t), 2.074 (1H, m), 2.267–2.47 (3H, m), 3.277 (3H, m), 3.662 (3H, s), 5.194 (1H, t), 5.494 (1H, s), 5.95 (2H, s), 6.714 (1H, s) 6.959 (1H, s).

EXAMPLE 58

Figure 12:
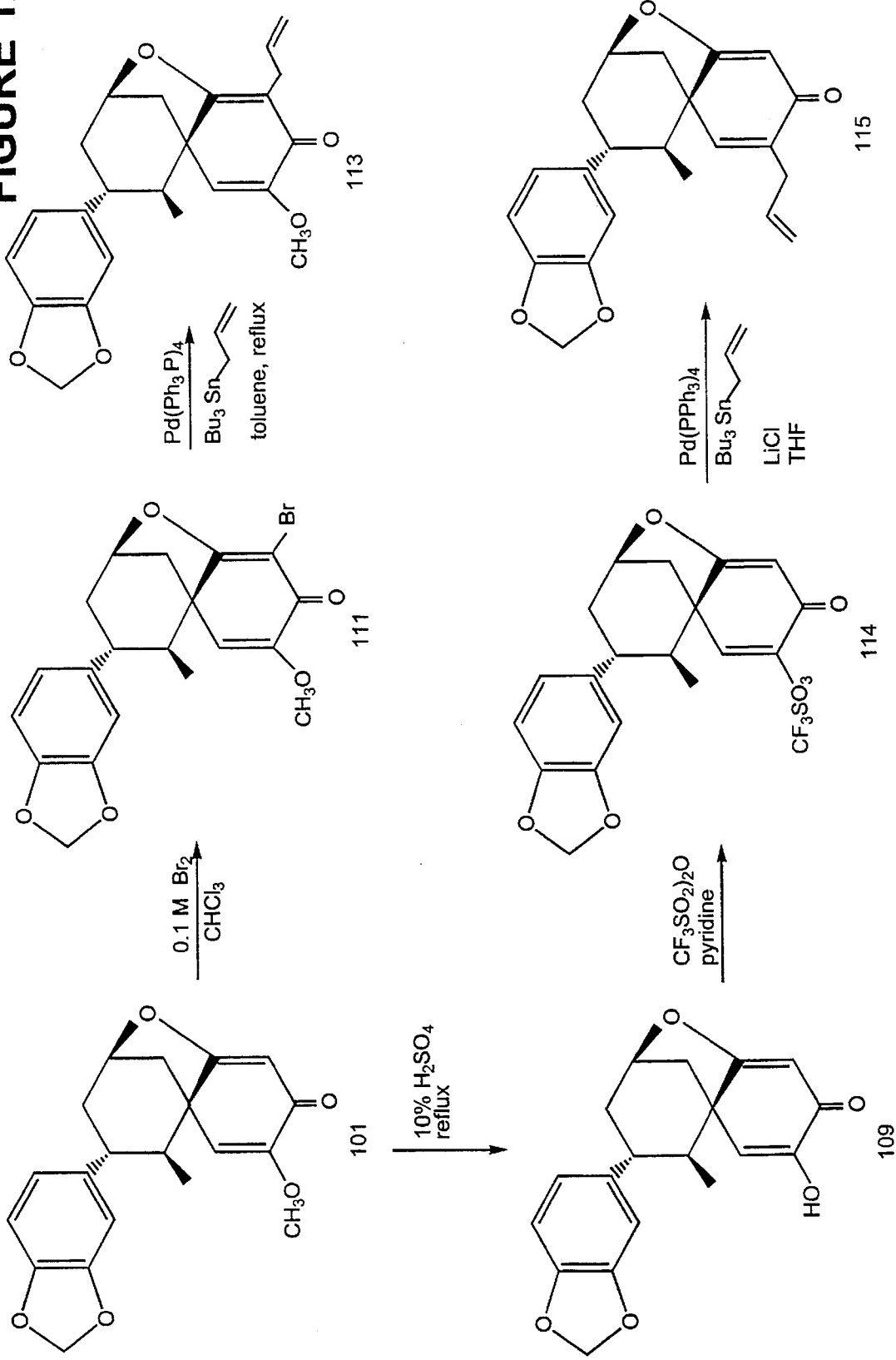

4-(1,3-benzodioxol-5-yl)-2,3,4,5-tetrahydro-7-methoxy-5-methyl-8H-2,5a-methano-9-allyl-1-benzoxepin-8-one (113, FIG. 12)

Tetrakis (triphenylphosphine)palladium (o) (14.9 mg, 0.013 mmoles) and allyltributyltin (88 Ul, 0.28 mmoles) are added to a stirred solution of 4-(1,3-benzodioxol-5-yl)-2,3, 4,5-tetrahydro-7-methoxy-5-methyl-8H-2,5a-methano-9-bromo-1-benzoxepin-8-one (111, prepared according to Example 20) in 4 ml of toluene. The reaction is heated to reflux for four and half hours after which the formation of reaction product is detectable by TLC using ethyl acetate. The reaction is then concentrated in vacuo and purified by MPLC using ethyl acetate. The product is a pale yellow foam (80.6 mg, 38%). M+(CI)=381. $^1$NMR ppm: 0.55 (3H, d), 1.70 (1H, t), 2.0 (1H, m), 2.15 (1H, d), 2.31 (21H, m), 2.49 (1H, m), 3.16 (2H, dd), 3.64 (3H, s), 5.0 (3H, m), 5.44 (1H, s), 5.93 (3H, m), 6.66 (3H, m).

EXAMPLE 59

4-(1,3-benzodioxol-5-yl)-2,3,4,5-tetrahydro-7-trifluoro-acetyl-5-methyl-8H-2,5a-methano-1-benzoxepin-8-one (114, FIG. 12)

Trifluoroacetic anhydride (85.4 Ul, 0.51 mmoles) in pyridine (3.5 ml) is added at −40° C. to a stirred solution of 4-(1,3-benzodioxol-5-yl)-2,3,4,5-tetrahydro-7-hydroxy-5-methyl-8H-2,5a-methano-1-benzoxepin-8-one (109, as prepared in Example 54)(110.3 mg, 0.34 mmoles). The reaction is stirred at −40° to 0° C. over a three hour period and is then washed with saturated sodium bicarbonate and dried over sodium sulfate. The reaction mixture is filtered, concentrated in vacuo, and purified using MPLC with ethyl acetate. A reddish oil (135.9 mg, 87.6%) is isolated and characterized by mass spec. and $^1$H NMR. N+(CI)=405. $^1$H NMR ppm: 0.65 (3H, d), 1.75 (1H, t), 2.20 (3H, m), 2.53 (2H, m), 5.1 (1H, t), 5.85 (1H, s), 5.93 (2H, s), 6.68 (4H, m).

EXAMPLE 60

4-(1,3-benzodioxol-5-yl)-2,3,4,5-tetrahydro-7-allyl-5-methyl-8H-2,5-methano-1-benzoxepin-8-one (115, FIG. 12)

Tetrakis (triphenylphosphine)palladium (o) (1.4 mg, 0.002 mmols), lithium chloride (24.2 mg, 0.57 mmols) and 2 ml of THF are added to a solution of 4-(1,3-benzodioxol-5-yl)-2,3,4,5-tetrahydro-7-trifluoro-acetyl-5-methyl-8H-2, 5a-methano-1-benzoxepin-8-one (114, prepared according to Example 23) (37.5 mg, 0.079 mmols) and allyltributylin (24.5 µl,0.079 mmols) in 1.5 ml THF. The reaction is heated to reflux in an oil bath for five hours. The yellow reaction mixture is diluted with pentane and washed with 10% ammonium hydroxide. The extract is dried over sodium sulfate, filtered and concentrated in vacuo. The reaction is purified by MPLC on silica gel using 1:1 hexane-ethyl acetate as the eluant. The fractions corresponding to the product are combined and concentrated in vacuo to form a pale yellow foam (19 mg, 68.7%). M+(CI)=367. $^1$H NMR ppm: 0.52 (3H, d), 1.70 (1H, dd), 2.02 (1H, m), 2.07 (1H, d), 2.30 (2H, m), 3.09 (2H, td), 4.98 (1H, t), 5.08 (2H, dd), 5.74 (1H, s), 5.83 (1H, m), 5.93 (2H, s), 6.36 (1H, s), 6.67 (3H, m).

EXAMPLE 61

4-(1,3-benzodioxol-5-yl)-2,3,4,5-tetrahydro-7-methoxy-5-methyl-8H-2,5a-methano-1-benzoxepin-8-thione (102, FIG. 9)

Lawesson's reagent (119.3 mg, 0.3 mmoles) is added to a stirred solution of futoenone (200 mg, 0.59 mmoles) in toluene (4 ml). The reaction is heated to 60° C. in an oil bath for 2–3 h. TLC of the reaction mixture shows almost complete conversion of starting material. The reaction turns from a green to violet upon heating. The reaction is concentrated in vacuo and purified by MPLC on silica gel using ethyl acetate. A purple foam (154.2 mg, 73.5%) forms upon drying in vacuo. M+(CI)=357. $^1$H NMR ppm: 0.59 (3H, d), 1.72 (1H, t), 2.07 (1H, m), 2.21 (1H, d), 2.30 (1H, m), 2.43 (1H, m), 2.58 (1H, m), 3.71 (3H, s), 5.08 (1H, t), 5.46 (1H, s), 5.92 (2H, s), 6.65 (4H, m).

EXAMPLE 62

2-[3-hydroxy-2-(1,3-benzodioxol-5-yl)butane]-6-methoxy-7-thioacetyldihydrobenzofuran (104, FIG. 9)

Boron trifluoride- etherate (42.6 µl, 0.35 mmoles) is added to a stirred solution of 4-(1,3-benzodioxol-5-yl)-2,3, 4,5-tetrahydro-7-methoxy-5-methyl-8H-2,5a-methano-1-benzoxepin-8-thione (102, prepared according to Example 61) (81.2 mg, 0.23 mmoles) in acetic at anhydride at 0° C. under argon. The reaction changes color from purple to orange then to an orange-yellow color. After stirring at 0° C. for two hours, the reaction is washed with saturated sodium bicarbonate. The extract is dried over sodium sulfate, filtered, and concentrated in vacuo. M+(CI)=459. $^1$H NMR ppm: 1.05 (3H, d), 1.76 (1H, td), 2.05 (3H, s), 2.21 (1H, td), 2.38 (3H, s), 2.74 (1H, dd), 2.98 (1H, td), 3.10 (1H, dd), 3.75 (3H, s), 4.42 (1H, q), 5.02 (1H, m), 5.94 (3H, s), 6.71 (5H, m). Anal. Calcd. for $C_{24}H_{22}O_4S$: C, 62.87; H, 5.72; S, 7.0. Found: C, 62.80; H, 5.75; S, 7.06. (Analytical data C=carbon, H=hydrogen, and S=sulfur).

EXAMPLE 63

2-[3-hydroxy-2-(1,3-benzodioxol-5-yl)butane]-6-methoxy-7-thioldihydrobenzofuran (106a, FIG. 9)

Methanolic HCl is added to a stirred solution of 2-[3-hydroxy-2-(1,3-benzodioxol-5-yl) butane]-6-methoxy-7-thioacetyldihydrobenzofuran (104, prepared as described in Example 62) (33.1 mg, 0.072 mmoles) in 0.25 ml chloroform at 0° C. under argon. Methanolic HCl is generated by addition of acetyl chloride to methanol at 0° C. The reaction is stirred an 0° C. for one hour and is then allowed warm to room temperature overnight. The reaction is monitored by TLC and after 48 hours is stopped. The mixture is washed with saturated sodium bicarbonate, followed by water and dried over sodium sulfate. The product (21.9 mg, 81%) is purified by MPLC on silica gel using ethyl acetate. M+(CI) =374. $^1$H NMR ppm: 1.05 (3H, d), 1.81 (1H, td), 2.39 (1H, td), 2.71 (1H, dd), 2.82 (1H, m), 3.05 (1H, dd), 3.76 (1H, s), 3.79 (3H, s), 4.49 (1H, q), 5.98 (2H, s), 6.71 (5H, m).

EXAMPLE 64

2-[3-hydroxy-2-(1,3-benzodioxol-5-yl)butane]-6-methoxy-7-thiomethyldihydrobenzofuran (106b)

Iodomethane (11.3 mg, 0.08 mmols) and potassium carbonate (21.9 mg, 0.159 mmols) with a small amount of 18-crown-6 ether are added to a stirred solution of 2-[3-hydroxy-2-(1,3-benzodioxol-5-yl)butane]-6-methoxy-7-thioldihydrobenzofuran (106a, prepared as described in Example 63) (20 mg, 0.053 mmols) in THF (1.5 ml). The reaction is stirred an room temperature for six hours under argon, afterwhich the reaction is washed with sodium bicarbonate followed by water. The extract is dried over sodium sulfate, filtered, and concentrated in vacuo. The reaction is purified by MPLC using 1:1 hexane-ethyl acetate, and an oil is isolated (48.3%). M+(CI)=390.

EXAMPLE 65

Figure 13:
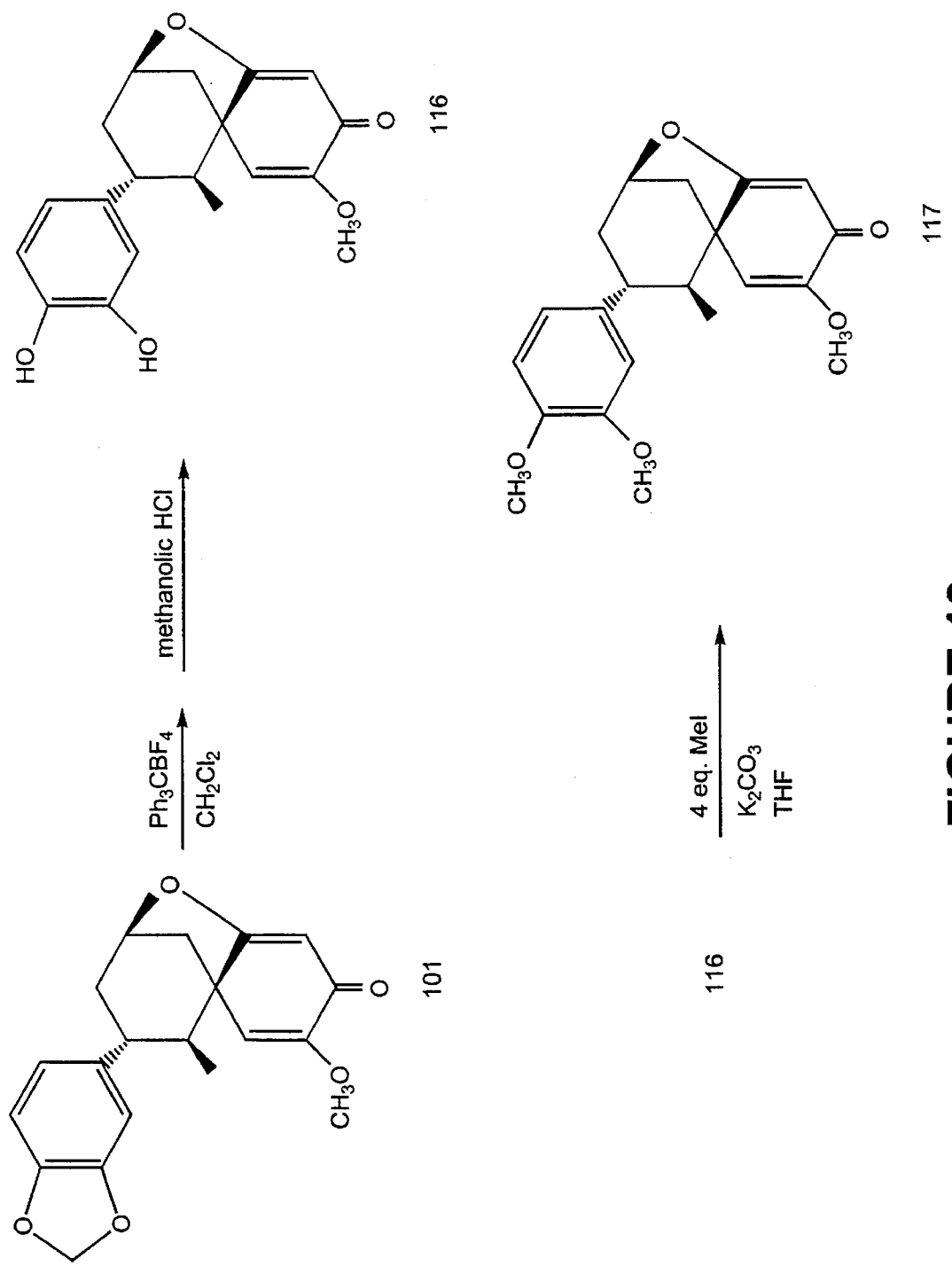

4-(1,3-dihydroxyphenyl)-2,3,4,5-tetrahydro-7-methoxy-5-methyl-8H-2,5a-methano-1-benzoxepin-8-one (116, FIG. 13)

Triphenylcarbenium tetrafluoroborate (359 mg, 1.09 mmols) is added to a stirred solution of futoenone (101) (200 mg, 0.588 mmols) in 2 ml distilled dichloromethane. The reaction is stirred for one hour an 0° C. The flask is then warmed no room temperature and stirred for an additional 24 hours. The reaction is monitored with TLC. After the starting material was completely consumec (approximately 24 h), the solvent is removed :n vacuo and the reaction mixture purified using flash column chromatography on silica (50 g, ethyl acetate) to produce a mixture as a product (0.1871 g, 97%)(as determined by 1H NMR). The reaction mixture is dissolved in 2 ml chloroform and a solution of methanolic HCl is added dropwise to the flask. After stirring for 1 h at 0° C., the mixture is warmed to room temperature overnight. No change is seen in the mixture by TLC after 12 h. The reaction is washed using sodium bicarbonate followed by water. The extract is concentrated in vacuo and triturated with methylene chloride to form white crystals 0.12 g (70%). M+(CI)=329. $^1$H NMR ppm: 0.39 (3H, d), 1.72 (1H, t), 2.1–2.3 (5H, m), 3.62 (3H, s), 5.03 (1H, t), 5.53 (1H, s), 5.68 (1H, s), 6.60 (1H, dd), 6.70 (1H, d), 6.81 (1H, d).

EXAMPLE 66

4-(1,3-dimethoxyphenyl)-2,3,4,5-tetrahydro-7-methoxy-5-methyl-8H-2,5a-methano-1-benzoxepin-8-one (117, FIG. 13)

Potassium hydroxide (71.8 mg, 1.28 mmols) and 18-crown-6 ether (45.6 mg, 0.17 mmols) are added to a stirred solution of 4-(1,3-dihydroxyphenyl)-2,3,4,5-tetrahydro-7-methoxy-5-methyl-8H-2,5a-methano-1-benzoxepin-8-one (116, prepared according to Example 65) (70 mg, 0.21 mmols) in 1 ml distilled THF. The reaction mixture turns blue. Upon addition of iodomethane (53 µl, 0.85 mmols), the reaction turns purple. After 30 minutes, the reaction is washed with 10% HCl followed by water. The reaction mixture turns yellow and is dried over sodium sulfate. The reaction is purified using MPLC on silica gel (15 g, 1:1 hexane-ethyl acetate), 53.3 mg (79%). M+(CI)=357. $^1$H NMR ppm: 0.58 (3H, d), 1.74 (1H, t), 2.04 (1H, m), 2.20 (1H, d), 2.3 (2H, m), 2.55 (1H, m), 3.676 (3H, s), 3.87 (6H, d), 5.04 (1H, t), 5.49 (1H, s), 5.79 (1H, s), 6.69 (1H, s), 6.72 (1H, d), 6.82 (1H, d).

Figures 16A, 16B:
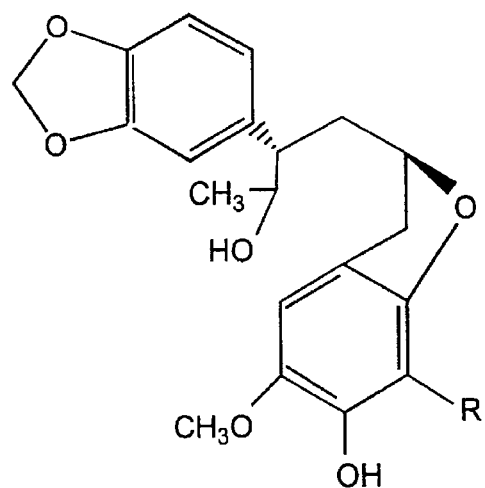
FIGS. 16a and 16b are respectively a chemical structure of a substituted futoenone derivative compound and a table showing the 5-lipoxygenase inhibitory activity of particular futoenone derivative compounds.

Referring now to FIGS. 14a, 14b, 15a, 15b, 16a, and 16b, many futoenone derivative compounds have been synthesized according to the schemes shown in FIGS. 9–13 and discussed in Examples 12 to 30 and many other futoenone derivative compounds are readily synthesizable via the same or similar schemes. Several of these compounds have been tested for their antagonist activity for PAF induced platelet aggregation and for their inhibition of the production of leukotrienes via the 5-lipoxygenase pathway in PMN leukocytes or monocytes according to the procedures described above. FIGS. 14b and 15b show that small concentrations of futoenone and futoenone derivative compounds exhibit potent PAF antagonist activity and FIG. 16b shows that small concentrations of futoenone derivative compounds exhibit potent 5-lipoxygenase inhibition. Therefore, these compounds would be beneficial for the treatment of the large number of diseases and disorders that are mediated by leukotrienes and PAF.

Figure 17:
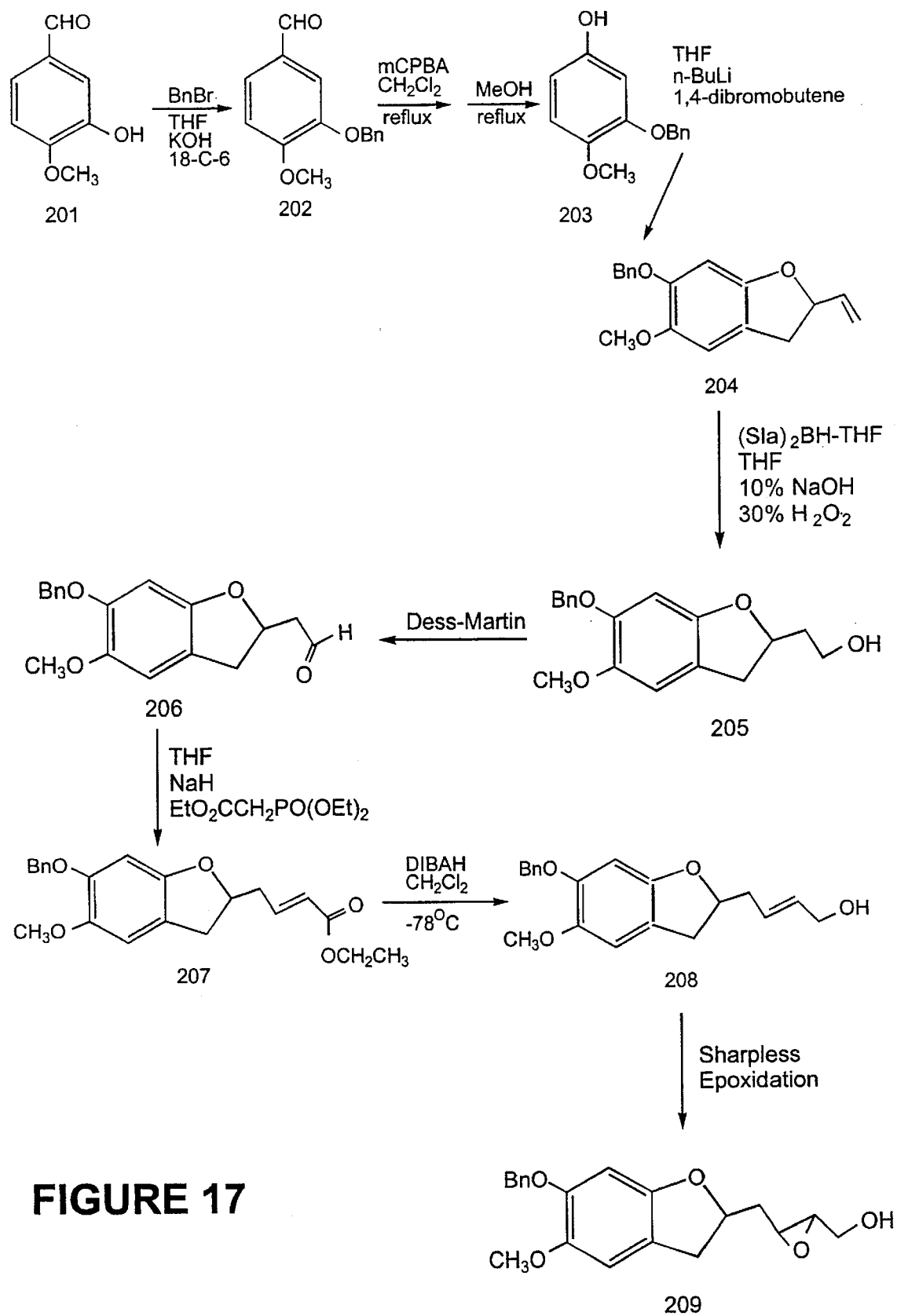
FIGS. 17 and 18 are schematic drawings showing a synthetic pathway for producing futoenone and futoenone derivative compounds.
Figure 18:
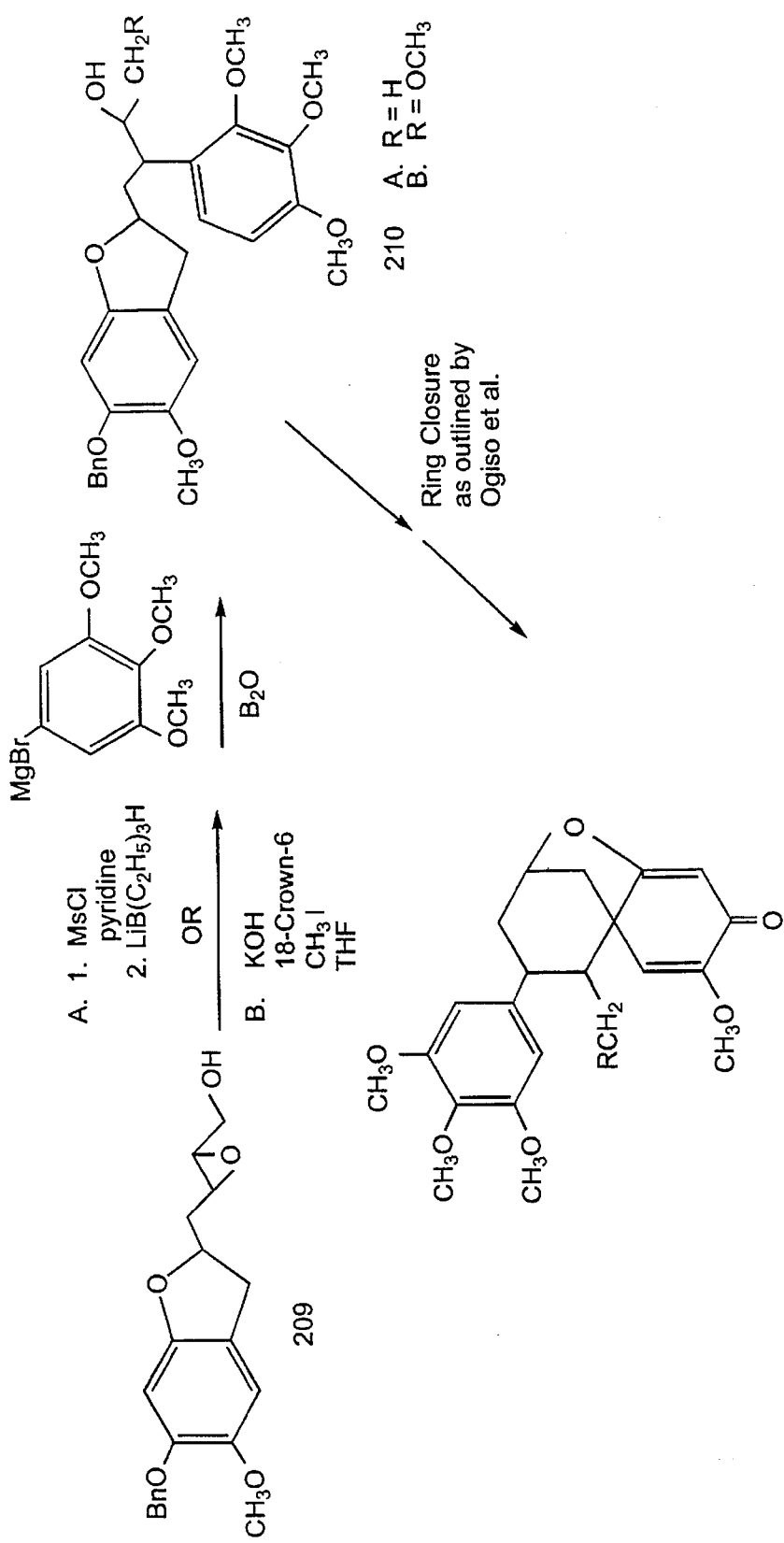

FIGS. 17 and 18 disclose a procedure for synthesizing futoenone and futoenone derivative compounds. Benzyl bromide (BnBr) is used to protect isovanillin (201) by reaction using phase transfer conditions to yield 3-benzyloxy-4-methoxybenzaldehyde (202). Oxidation of 3-benzyloxy-4-methoxybenzaldehyde (202) with m-chloroperbenzoic acid followed by hydrolysis in refluxing methanol yields 3-benzyloxy-4-methoxyphenol (203). The phenol is placed in toluene and the suspension is treated with n-butyl-lithium to form a precipitate. 1,4-dibromobutene is then added to the reaction and the contents are heated to reflux overnight to form vinylbenzofuran (206). An ester (207) is formed using a Horner-Emmons modified Wittig reaction and is subsequently reduced to the allylic alcohol (208) using diisobutylaluminum hydride. The allylic alcohol can then be epoxidized in a Sharpless epoxidation to form 2-(2,3'-epoxybutanol)-7-benzyloxy-6-methoxydihydrobenzofuran (209).

The use of the Sharpless epoxidation provides the benefit of enantiomeric selectively at the chiral center indicated by the star. FIG. 18 shows the epoxide (209) can then be opened using a substituted aryl or heteroaryl Grignard or Lewis acid to form, for example, the trimethyoxyphenyl derivative 2-[3-hydroxy-3-methoxy-2-(1,3-benzodioxol-5-yl)propane]-7-hydroxy-6-methoxydihydrobenzofuran (210) (this is reaction scheme B in FIG. 18). Alternatively, the primary alcohol formed from epoxide opening of (209) can be removed by conversion to a good leaving group followed by treatment with lithium superoxide, or alkylated with various groups such as methyl iodide, to form (210) (this is reaction scheme A in FIG. 18 which involves the use of lithium triethylborohydride). To prepare derivatives of futoenone from 2-[3-hydroxy-3-methoxy-2-(1,3-benzodioxol-5-yl)propane]-7-hydroxy-6-methoxydihydrobenzofuran (210) would simply involve ring closure following the procedure of Ogisa.

Formation of the epoxide (209) in FIG. 17 should provide an easy way to modify the top aromatic ring on the futoenone skeleton. The 3,4,5-trimethoxyphenyl magnesium bromide can be replaced by other substituted aryl or heteroaryl (such as furyl, thienyl, pyridyl, or indolyl) Grignard reagents to prepare the corresponding aryl substituted futoenone derivatives. The top aromatic ring of the futoenone skeleton could be substituted with hydrogen, lower alkyl, lower alkenyl, lower alkynyl, lower alkoxy, methylene dioxy, lower alkylthio, hydroxy, lower alkyl sulfonyl, hydroxy lower alkyl sulfonyl, lower alkyl sulfinyl, hydroxy lower alkylsulfinyl, aminoalkylsulfonyl, acyloxyalkylsulfonyl, acylamidoalkylsulfonyl, halogen, haloalkyl, alkoxyalkyl, alkylthioalkyl, or the like. Additionally, as shown in FIG. 18, the hydroxy at the end of 2-(2,3'-epoxybutanol)-7-benzyloxy-6-methoxydihydrobenzofuran (209) provides a handle by which the R group can be selectively modified. While FIG. 18 shows the formation of futoenone derivative compounds with the R group denoted as a hydrogen or methoxy it should be understood that the R group can be replaced with other alkoxy groups as well as alkylthio groups.

The following Examples provide further discussion related to the synthetic pathway for producing futoenone analogs which is shown in FIGS. 17 and 18.

EXAMPLE 67

3-benzyloxy-4-methoxybenzaldehyde (202, FIG. 17)

18—Crown-6 ether (0.14 g, 0.00052 mols) and potassium hydroxide (1.35 g, 0.024 mols) is added to a stirred solution of isovanillin (201) (2.0 g, 0.013 mols) in THF (20 ml) at 0° C. The reacton becomes cloudy and turns bright yellow. Benzyl bromide (1.69 ml, 0.0143 mols) is added dropwise to the reaction at 0° C. After one hour, the ice bath is removed and the reaction is stirred at room temperature overnight. The reaction is diluted with ethyl acetate and washed with water and 10% HCl followed by brine solution. The organic extract is dried over sodium sulfate, filtered, concentrated and dried in vacuo no a yellow crystalline solid (3.0471 g, 96.9%).

EXAMPLE 68

3-benzyloxy-4-methoxyphenol (203, FIG. 17)

3-chloroperoxybenzoic acid (9.9 g, 0.0343 mols), in small portions, is added to a stirred solution of 3-benzyloxy-4-methoxybenzaldehyde (201, prepared as described in Example 66) (7.57 g, 0.0313 mols) in dicloromethane (100 ml) over a thirty minute period With vigorous shirring. The reaction flask is fitted with a condensor and the contents is heated to reflux for six hours and monitored by TLC using 2:1 hexane-ethyl acetate as eluant. The reaction is filtered off the 3-chlorobenzoic acid (which precipitates out of solution) and the filtrate is washed with saturated sodium bicarbonate followed by water and dried in vacuo to an oil which eventually solidifies. The solid is subsequently dissolved in distilled methanol (80 ml) and heated to reflux under nitrogen. TLC using hexane-ethyl acetate as the eluant shows almost complete conversion after two hours and forty five minutes. The solvent is removed in vacuo no produce a dark oil which is redissolved in a small amount of ethyl acetate and purified by column chromatography on silica gel (2:1 hexane-ethyl acetate as eluant). The major fraction from the column is combined and concentrated in vacuo to a solid (4.68 g, 64.9%).

EXAMPLE 69

2-vinyl-7-benzyloxy-6-methoxydihydrobenzofuran (204, FIG. 17)

Using the procedure of Bigi et al, Tetrahedron, 39, 169 (1983), the benzofuran system is constructed. N-butyl lithium (3.95 ml of a 2.2M solution) is added to a solution of 3-benzyloxy-4-methoxyphenol (203, prepared as described in Example 32)(2.0 g, 0.0087 mols) in dry toluene. Upon addition of the n-butyl lithium, a precipitate falls out of solution. After all the n-butyl lithium is added, the reaction is starred for 15–20 minutes at room temperature. Subsequently, the reaction is heated to reflux for twenty one hours. The reaction is then diluted with ethyl acetate and washed with 10% HCl and water. The extract is dried over sodium sulfate. The crude reaction mixture is purified by flash column chromatography using 2:1 hexane-ethyl acetate as eluant to obtain two major products which are (1) unreacted starting material and (2) product (0.979 g, 37.6%)

EXAMPLE 70

2-(2'-hydroxyethane)-7-benzyloxy-6-methoxydihydrobenzofuran (205, FIG. 17)

BH$_3$.THF complex (4.8 ml, 0.0048 mols) is added to a stirred solution of 2-methyl-2-butene (1.02 ml, 0.0096 mmols) in distilled THF (4 ml) at 4° C. under nitrogen. The reaction is stirred at 4° C. for one hour. 2-vinyl-7-benzyloxy-6-methoxydihydro benzofuran (204,described above in Example 69) (0.896 g, 0.0032 mols) in distilled THF (4 ml) is added rapidly dropwised no the shirred reaction. After five minutes, the reaction is removed from the ice bath and sniffed at room temperature for three and one half hours while being monitored every half hour by TLC using 1:1 hexane-ethyl acetate as eluant). The reaction is then cooled no 4° C. and 10% sodium hydroxide (2.8 ml) is added slowly dropwise to the reaction while keeping the intenal temperature below 20° C. The cooling bath is removed after one hour and the reaction is diluted with ethyl acetate and washed with water and 10% HCl. The extract is dried over sodium sulfate and purified by column chromatography on silica gel using 1:1 hexane-ethyl acetate as eluant to produce an off-white solid (0.4942 g, 5.15%).

EXAMPLE 71

2-(acetaldehyde)-7-benzyloxy-6-methoxydihydro benzofuran (206, FIG. 17)

The following oxidationis performed using Dess-Martin conditions (see, Dess et al, *J. Org. Chem.*, 48, 4156 (1983)). A solution of 2-(2'-hydroxyethane)-7-benzyloxy-6-methoxydihydrobenzofuran (205,described in Example 70) (166.8 mg, 0.56 mmols) in dichloromethane (2 ml) is added to a stirred solution of periodinane (259.3 mg, 0.612 mmols) in dichloromethane (4 ml). The reaction is shirred forty five minutes while being monitored every fifteen minutes by TLC using 1:1 hexane-ethyl acetate as eluant. The reaction is then diluted with aqueous sodium bicarbonate and sodium thiosulfate. The extract is dried over sodium sulfate and the reaction is purified using column chromatography on silica gel (1:1 hexane-ethyl acetate) to a colorless oil (90.6 mg, 54.3%).

EXAMPLE 72

2-(ethyl crotonate)-7-benzyloxy-6-methoxydihydrobenzofuran (207, FIG. 17)

Triethylamine (53.1 µl, 0.268 mmols) is added to a stirred solution of sodium hydride (6.44 mg, 0.268 mmols) in THF (4 ml) at room temperature under nitrogen. The mixture is stirred for fifteen minutes before a solution of 2-(acetaldehyde)-7-benzyloxy-6-methoxydihydrobenzofuran (206, prepared as described in Example 71) (80 mg, 0.268 mmols) in THF (2 ml) is added dropwise slowly to the reaction. The reaction turns dark upon addition of the aldehyde and is stirred for an additional ten minutes at room temperature after which TLC with 1:1 hexane-ethyl acetate shows no additional aldehyde present. Several drops of ethanol are added no react with any unreacted sodium hydride. The reaction is subsequently diluted with ethyl acetate, washed with water, and dried over sodium sulfate. The extract is filtered and concentrated in vacuo with crude $^1$H NMR showing the desired product. Further purification is performed by column chromatography on silica gel (1:1 hexane-ethyl acetate) to yield a colorless oil (85.8 mg, 87%).

EXAMPLE 73

2-(2'-buten-4'-ol)-7-benzyloxy-6-methoxydihydrobenzofuran (208, FIG. 17)

Diisobutylaluminum hydride (DIBAH) (0.2 ml, 0.2 mmol) is added to a stirred solution of 2-(ethylcrotonate)-

7-benzyloxy-6-methoxydihydrobenzofuran (207, prepared as described in Example 72) (66.9 mg, 0.182 mmols) in distilled dichloromethane (4 ml) at −78° C. under nitrogen. The reaction is stirred thirty minutes, quenched by the addition of ethyl acetate (2 ml), and allowed to warm to room temperature. The reaction is diluted with diethyl ether (4 ml) and extracted with an aqueous solution of sodium potassium tartrate and brine. The extract is dried over sodium sulfate and filtered through celite. The reaction mixture is purified by column chromatography on silica gel using 1:1 hexane-ethyl acetate as eluant to produce a yellow oil (43.7 mg, 73.7%).

EXAMPLE 74

2-(2',3'-epoxybutanol)-7-benzyloxy-6-methoxydihydrobenzofuran (209, FIG. 17)

This compound has not been prepared but can be prepared by Sharpless epoxidation methodology (see, Katsuki et al., *J. Amer. Chem. Soc.*, 102, 5974 (1980). Dichloromethane should be placed in a round bottom flask and cooled to −23° C. in a dry ice/carbontetrachloride bath. The following are then added sequentially by syringe with vigorous stirring: titanium tetraisopropoxide and L(+)-diethyl tartrate. This mixture would then be stirred for five minutes followed by the addition of 2-(2'-buten-4'-ol)-7-benzyloxy-6-methoxydihydro benzofuran (208, prepared as described in Example 37) and a solution of dichloromethane and t-butylhydroperoxide. The reaction can be stored overnight in the freezer at −20° C. in a sealed reaction vessel. The flask would then be cooled to −23° C. and 10% aqueous tartaric acid solution would be added. After thirty minutes, the bath would be removed and the reaction would be stirred for one hour. The organic layer would be washed with water and dried over sodium sulfate.

EXAMPLE 75

2-(2',3'-epoxy-4-methoxybutane)-7-benzyloxy-6-methoxydihydrobenzofuran

Potassium hydroxide, 18-crown-6 ether followed by iodomethane would be added to a stirred solution of 2-(2',3'-epoxy-4-methoxybutane)-7-benzyloxy-6-methoxydihydrobenzofuran (209, prepared as described in Example 74) in THF. The reaction would be monitored by TLC until the starting materials are consumed. The reaction would then be washed with water, 10% HCl and brine. The organic extract would then be dried over sodium sulfate and purification would be performed using column chromatography on silica gel using hexane-ethyl acetate as the eluant.

EXAMPLE 76

2-[3-hydroxy-3-methoxy-2-(1,3-benzodioxol-5-yl) propane-7-hydroxy-6-methoxydihydrobenzofuran (210, FIG. 18)

Ring opening of 2-(2',3'-epoxy-4-methoxybutane)-7-benzyloxy-6-methoxydihydrobenzofuran (209, prepared as described in Example 74) would be performed by reaction with a Grignard reagent of 4-bromo-1,2-(methylenedioxy) benzene in anhydrous ether. The reaction would be acidified, washed with additional ether and dried over sodium sulfate. Purification would involve column chromatography on silica gel using a hexane-ethyl acetate solvent system.

EXAMPLE 77

Futoenone Analogs

The cyclization of 2-[3-hydroxy-3-methoxy-2-(1,3-benzodioxol-5-yl)propane)-7-hydroxy-6-methoxydihydrobenzofuran (210) would involve using the methodology previously performed by Ogiso et al., *Chem. Pharm. Bull.*, 18, 105 (1970), that article being herein incorporated by reference.

It is anticipated that the compounds of the present invention can be provided to human and animal patients in pharmaceutical doses for the purpose of inhibiting PAF and 5-lipoxygenase activity and, thereby, provide treatment or prevention of PAF and leukotriene disorders and diseases. The dose level will depend on a variety of factors including the activity of the specific compound employed and the age, sex, and physical condition of the subject being treated. It is anticipated that the dose level will be on the order of 0.1–30 mg/kg of body weight per day; however, larger and smaller amounts are anticipated. The compounds of the present invention can be administered orally, by injection, by suppository, or by any other pharmaceutically acceptable route. As is well understood in the art, the compounds can be administered as salts or the like and can be administered in conjunction with suitable inert binders, excipients, elixirs, emulsions, oils, suspensions, microencapsules, intradermal devices, ointments (topical administration), lubricating agents, and the like.

While the invention has been described in terms of its preferred embodiments wherein synthetic neolignan derivative compounds have been produced and used as PAF and 5-lipoxygenase antagonists, those skilled in the art will recognize that the invention can be practiced with modification within the spirit and scope of the appended claims.

We claim:

1. A compound of the formula:

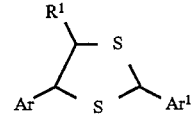

wherein $R^1$ is selected from the group consisting of hydrogen, haloloweralkyl, loweralkenyl, loweralkynyl, —$CONR^2R^3$ —$COR^2$, —$CO_2R^2$, —$CH_2OR^2$, —$CH_2NR^2R^3$, —$CH_2Sr^2$, and wherein Ar and $Ar^1$ are the same or different from each other and are substituted phenyl of the formula:

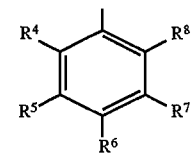

where $R^4$–$R^8$ independently are selected from the group consisting of —$NO_2$, —$NR^2R^3$, —$NR^2COR^3$, —N(OH) $COR^2$, —$NR^2CONR^2R^3$, —$NR^2CON(OH)R^2$, —$CO_2R^2$, —OC(O)$R^2$, —$R^2N(OH)CONR^2R^3$, —$CONR^2R^3$, —CON(OH)$R^2$, —$OR^2$, —$SR^2$, —$R^9$, —$R^9NR^2CON(OH)R^2$, —$R^9N(OH)CONR^2R^3$, —($C_5H_4N$), —$OR^9O(CO)N(COR^9)$ $R^9$, —($C_5H_4N)R^9R^{10}$, —$OR^9O(CO)N(CO_2R^9)R^9$, —$OR^9OH$, —$SR^9OH$, —$OR^9$, —$SR^9$, —X, —hydrogen, —$R^2$, —CN, —$R^9NR^2R^3$, —$SOR^9$, —$SO_2R^9$, —$SOR^9OH$, —$SO_2R^9OH$, —$OR^9OR^2$, and —$O_2CNR^2R^3$, and wherein $R^2$ and $R^3$ independently represent $C_{1-10}$ alkyl, alkenyl, alkynyl, aryl, aralkyl, and hydrogen, wherein $R^9$ is selected from the group consisting of haloalkyl, loweralkyl, loweralkenyl, lower alkynyl, aralkyl, and aryl, and wherein $R^{10}$ is an organic or inorganic anion and X is halogen, wherein a hyphen preceding $R^2$ or $R^9$ indicates that the $R^2$ or $R^9$ substituent is attached to the substituted phenyl, and wherein a N, O or S adjacent to $R^2$ or $R^9$ indicates that the N, O, or S is bonded directly to the $R^2$ or $R^9$ substituent.

2. The compound of claim 1 wherein $R^1$ is H.

3. The compound of claim 1 wherein $R^4$-$R^8$ are selected from the group consisting of —CON(OH)$R^2$, —N(OH)COR$^2$, and —NR$^2$CON(OH)R$^2$.

4. The compound of claim 1 wherein $R^4$-$R^8$ are —R$^9$N(OH)CONR$^2$R$^3$.

5. The compound of claim 1 wherein $R^4$-$R^8$ are —R$^9$NR$^2$CON(OH)R$^2$.

6. The compound of claim 1 wherein $R^4$-$R^8$ are —R$^2$N(OH)CONR$^2$R$^3$.

7. The compound of claim 1 wherein $R^4$-$R^8$ are selected from the group consisting of —OR$^9$, —SR$^9$, —OR$^2$, —SR$^2$, and —OR$^9$OR$^2$.

8. The compound of claim 1 wherein $R^4$-$R^8$ are selected from the group consisting of hydrogen, —SO$_2$R$^9$, —NR$^2$R$^3$ and —R$^9$NR$^2$R$^3$.

9. The compound of claim 1 wherein $R^2$ and $R^3$ are independently selected from the group consisting of hydrogen and $C_{1-10}$ alkyl.

10. The compound of claim 1 wherein $R^2$ and $R^3$ are independently selected from the group consisting of $C_{1-10}$ alkenyl and alkynyl.

11. The compound of claim 1 wherein $R^9$ is lower alkyl.

12. The compound of claim 1 wherein $R^9$ is lower alkenyl or lower alkynyl.

13. The compound of claim 1 wherein $R^{10}$ is an organic anion.

14. The compound of claim 1 wherein $R^{10}$ is an inorganic anion.

15. A method of inhibiting PAF induced platelet aggregation in a patient wherein said method comprises administering to the patient an effective amount of a compound of the formula:

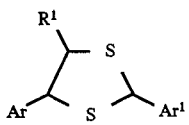

wherein $R^1$ is selected from the group consisting of hydrogen, haloloweralkyl, loweralkenyl, loweralkynyl, —CONR$^2$R$^3$ —COR$^2$, —CO$_2$R$^2$, —CH$_2$OR$^2$, —CH$_2$NR$^2$R$^3$, —CH$_2$SR$^2$, and wherein Ar and Ar$^1$ are the same or different from each other and are substituted phenyl of the formula:

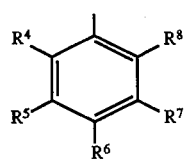

where $R^4$-$R^8$ independently are selected from the group consisting of —NO$_2$, —NR$^2$R$^3$, —NR$^2$COR$^3$, —N(OH)COR$^2$, —NR$^2$CONR$^2$R$^3$, —NR$^2$CON(OH)R$^2$, —CO$_2$R$^2$, —OC(O)R$^2$, —R$^2$N(OH)CONR$^2$R$^3$, —CONR$^2$R$^3$, —CON(OH)R$^2$, —OR$^2$, —SR$^2$, —R$^9$, —R$^9$NR$^2$CON(OH)R$^2$, —R$^9$N(OH)CONR$^2$R$^3$, —(C$_5$H$_4$N), —OR$^9$O(CO)N(COR$^9$)R$^9$, —(C$_5$H$_4$N)R$^9$R$^{10}$, —OR$^9$O(CO)N(CO$_2$R$^9$)R$^9$, —OR$^9$OH, —SR$^9$OH, —OR$^9$, —SR$^9$, —X, —hydrogen, —R$^2$, —CN, —R$^9$NR$^2$R$^3$, —SOR$^9$, —SO$_2$R$^9$, —SOR$^9$OH, —SO$_2$R$^9$OH, —OR$^9$OR$^2$, and —O$_2$CNR$^2$R$^3$, and wherein $R^2$ and $R^3$ independently represent $C_{1-10}$ alkyl, alkenyl, alkynyl, aryl, aralkyl, and hydrogen, wherein $R^9$ is selected from the group consisting of haloalkyl, loweralkyl, loweralkenyl, lower alkynyl, aralkyl, and aryl, and wherein $R^{10}$ is an organic or inorganic anion and where X is halogen, wherein a hyphen preceding $R^2$ or $R^9$ indicates that the $R^2$ or $R^9$ substituent is attached to the substituted phenyl, and wherein a N, O or S adjacent to $R^2$ or $R^9$ indicates that the N, O, or S is bonded directly to the $R^2$ or $R^9$ substituent.

16. A method of inhibiting the production of leukotrienes in a patient wherein said method comprises administering to the patient an effective amount of a compound of the formula:

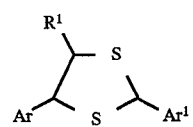

wherein $R^1$ is selected from the group consisting of hydrogen, haloloweralkyl, loweralkenyl, loweralkynyl, —CONR$^2$R$^3$ —COR$^2$, —CO$_2$R$^2$, —CH$_2$OR$^2$, —CH$_2$NR$^2$R$^3$, —CH$_2$SR$^2$, and wherein Ar and Ar$^1$ are the same or different from each other and are substituted phenyl of the formula:

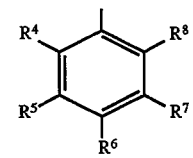

where $R^4$-$R^8$ independently are selected from the group consisting of —NO$_2$, —NR$^2$R$^3$, —NR$^2$COR$^3$, —N(OH)COR$^2$, —NR$^2$CONR$^2$R$^3$, —NR$^2$CON(OH)R$^2$, —CO$_2$R$^2$, —OC(O)R$^2$, —R$^2$N(OH)CONR$^2$R$^3$, —CONR$^2$R$^3$, —CON(OH)R$^2$, —OR$^2$, —SR$^2$, —R$^9$, —R$^9$NR$^2$CON(OH)R$^2$, —R$^9$N(OH)CONR$^2$R$^3$, —(C$_5$H$_4$N), —OR$^9$O(CO)N(COR$^9$)R$^9$, —(C$_5$H$_4$N)R$^9$R$^{10}$, —OR$^9$O(CO)N(CO$_2$R$^9$)R$^9$, —OR$^9$OH, —SR$^9$OH, —OR$^9$, —SR$^9$, —X, —hydrogen, —R$^2$, —CN, —R$^9$NR$^2$R$^3$, —SOR$^9$, —SO$_2$R$^9$, —SOR$^9$OH, —SO$_2$R$^9$OH, —OR$^9$OR$^2$, and —O$_2$CNR$^2$R$^3$, and wherein $R^2$ and $R^3$ independently represent $C_{1-10}$ alkyl, alkenyl, alkynyl, aryl, aralkyl, and hydrogen, wherein $R^9$ is selected from the group consisting of haloalkyl, loweralkyl, loweralkenyl, lower alkynyl, aralkyl, and aryl, and wherein $R^{10}$ is an organic or inorganic where X is halogen, wherein a hyphen preceding $R^2$ or $R^9$ indicates that the $R^2$ or $R^9$ substituent is attached to the substituted phenyl, and wherein a N, O or S adjacent to $R^2$ or $R^9$ indicates that the N, O, or S is bonded directly to the $R^2$ or $R^9$ substituent.

17. A method of inhibiting the production of both PAF induced platelet aggregation and the production of leukotrienes in a patient wherein said method comprises administering to the patient an effective amount of a compound of the formula:

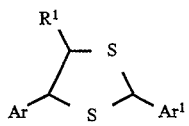

wherein $R^1$ is selected from the group consisting of hydrogen haloloweralkyl, loweralkenyl, loweralkynyl, —$CONR^2R^3$ —$COR^2$, —$CO_2R^2$, —$CH_2OR^2$, —$CH_2NR^2R^3$, —$CH_2SR^2$, and wherein Ar and $Ar^1$ are the same or different from each other and are substituted phenyl of the formula:

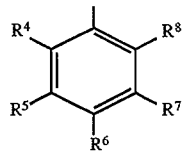

where $R^4$–$R^8$ independently are selected from the group consisting of —$NO_2$, —$NR^2R^3$, —$NR^2COR^3$, —$N(OH)COR^2$, —$NR^2CONR^2R^3$, —$NR^2CON(OH)R^2$, —$CO_2R^2$, —$OC(O)R^2$, —$R^2N(OH)CONR^2R^3$, —$CONR^2R^3$, —$CON(OH)R^2$, —$OR^2$, —$SR^2$, —$R^9$, —$R^9NR^2CON(OH)R^2$, —$R^9N(OH)CONR^2R^3$, —$(C_5H_4N)$, —$OR^9O(CO)N(COR^9)R^9$, —$(C_5H_4N)R^9R^{10}$, —$OR^9O(CO)N(CO_2R^9)R^9$, —$OR^9OH$, —$SR^9OH$, —$OR^9$, —$SR^9$, —X, —hydrogen, —$R^2$, —CN, —$R^9NR^2R^3$, —$SOR^9$, —$SO_2R^9$, —$SOR^9OH$, —$SO_2R^9OH$, —$OR^9OR^2$, and —$O_2CNR^2R^3$, and wherein $R^2$ and $R^3$ independently represent $C_{1-10}$ alkyl, alkenyl, alkynyl, aryl, aralkyl, and hydrogen, wherein $R^9$ is selected from the group consisting of haloalkyl, loweralkyl, loweralkenyl, lower alkynyl, aralkyl, and aryl, and wherein $R^{10}$ is an organic or inorganic anion and where X is halogen, wherein a hyphen preceding $R^2$ or $R^9$ indicates that the $R^2$ or $R^9$ substituent is attached to the substituted phenyl, and wherein a N, O or S adjacent to $R^2$ or $R^9$ indicates that the N, O, or S is bonded directly to the $R^2$ or $R^9$ substituent.

18. The method of claims 15, 16, or 17, wherein $R^1$ is H.

19. The method of claims 15, 16, or 17, wherein $R^4$–$R^8$ are selected from the group consisting of —$CON(OH)R^2$, —$N(OH)COR^2$, and —$NR^2CON(OH)R^2$.

20. The method of claims 15, 16, or 17, wherein $R^4$–$R^8$ are —$R^9N(OH)CONR^2R^3$.

21. The method of claims 15, 16, or 17, wherein $R^4$–$R^8$ are —$R^9NR^2CON(OH)R^2$.

22. The method of claims 15, 16, or 17, wherein $R^4$–$R^8$ are —$R^2N(OH)CONR^2R^3$.

23. The method of claims 15, 16, or 17, wherein $R^4$–$R^8$ are selected from the group consisting of —$OR^9$, —$SR^9$, —$OR^2$, —$SR^2$, and —$OR^9OR^2$.

24. The method of claims 15, 16, or 17, wherein $R^4$–$R^8$ are selected from the group consisting of hydrogen, —$SO_2R^9$, —$NR^2R^3$ and —$R^9NR^2R^3$.

25. The method of claims 15, 16, or 17, wherein $R^2$ and $R^3$ are independently selected from the group consisting of hydrogen and $C_{1-10}$ alkyl.

26. The method of claims 15, 16, or 17, wherein $R^2$ and $R^3$ are independently selected from the group consisting of $C_{1-10}$ alkenyl and alkynyl.

27. The method of claims 15, 16, or 17, wherein $R^9$ is lower alkyl.

28. The method of claims 15, 16, or 17, wherein $R^9$ is lower alkenyl or lower alkynyl.

29. The method of claims 15, 16, or 17, wherein $R^{10}$ is an organic anion.

30. The method of claims 15, 16, or 17, wherein $R^{10}$ is an inorganic anion.

* * * * *